(12) United States Patent
Verschoor et al.

(10) Patent No.: US 6,433,013 B1
(45) Date of Patent: Aug. 13, 2002

(54) COMPOSITION COMPRISING A CARRIER AND A PURIFIED MYCOBACTERIAL LIPID CELL-WALL COMPONENT AND ITS USE IN THE PREVENTION, TREATMENT AND DIAGNOSIS OF DISEASE

(75) Inventors: Jan Adrianus Verschoor, Pretoria (ZA); Anne Lenaerts, Genk (BE); Elzbieta Johannsen, Pretoria (ZA)

(73) Assignee: Adcock Ingram Limited, Bryanston (ZA)

( * ) Notice: Subject to any disclaimer, the term of this patent is extended or adjusted under 35 U.S.C. 154(b) by 0 days.

(21) Appl. No.: 09/388,725

(22) Filed: Sep. 2, 1999

Related U.S. Application Data

(63) Continuation-in-part of application No. PCT/GB98/00681, filed on Mar. 13, 1998.

(30) Foreign Application Priority Data

Mar. 3, 1997 (ZA) .............................................. 97/1817
Nov. 14, 1997 (ZA) ............................................. 97/10300

(51) Int. Cl.$^7$ ............................................... A61K 31/19
(52) U.S. Cl. ....................................... 514/557; 514/924
(58) Field of Search .................................. 514/557, 924

(56) References Cited

U.S. PATENT DOCUMENTS 5,573,915 A * 11/1996 Barry, III et al. ................ 435/6

FOREIGN PATENT DOCUMENTS

| EP | 0261248 | 3/1988 |
| WO | 9500163 | 1/1995 |
| WO | 9528642 | 10/1995 |

\* cited by examiner

*Primary Examiner*—Kevin E. Weddington
(74) *Attorney, Agent, or Firm*—Ladas & Parry

(57) ABSTRACT

A composition comprising a purified lipid cell-wall component or analog or derivative thereof and a suitable pharmaceutical carrier, medium, excipient or adjuvant is described. The composition is useful in prophylactic and therapeutic methods of treating a microbial infection in a subject, typically a mycobacterial infection such as tuberculosis, and immune disorders, inflammatory conditions and allergies in a subject, typically autoimmune diseases. It is also useful in diagnostic methods. The purified lipid cell-wall component is typically a purified mycolic acid or a mixture of purified mycolic acids from a bacterium which produces mycolic acids. The bacterium is from Mycobacterium, Corynebacterium, Nocardia or Rhodococcus.

10 Claims, 41 Drawing Sheets

COMPOSITION COMPRISING A CARRIER AND A PURIFIED MYCOBACTERIAL LIPID CELL-WALL COMPONENT AND ITS USE IN THE PREVENTION, TREATMENT AND DIAGNOSIS OF DISEASE

This application is a continuation-in-part of PCT/GB98/00681 filed Mar. 13 1998.

BACKGROUND OF THE INVENTION

This invention relates to a composition comprising a purified mycobacterial lipid cell-wall component or log or derivative thereof and a pharmaceutically acceptable excipient, medium, carrier or adjuvant and the use of the purified mycobacterial lipid cell-wall component or analog or derivative thereof and the composition containing it in the prevention, treatment and diagnosis of disease.

It has been known for a long time that BCG*) vaccination leads to the induction of a positive tuberculin skin test, resulting in delayed type hypersensitivity (DTH). This delayed hypersensitivity in turn has been considered to be indicative of the successful induction of protective immunity against tuberculosis and has led to the almost world-wide BCG immunization in the 1950s–1970s. This convenient test is in fact the only immunological criterion/parameter on which epidemiological assessments of the effectiveness of the immunization have been based.

BCG: (Bacillus of Calmette and Guerin) Calmette and Guerin attenuated a strain of *M. bovis* by passaging it 231 times over a period of 13 years through a medium containing glycerine and ox-bile.

This view is no longer generally accepted and many immunologists are of the opinion that i) the induction of DTH is not directly related to the degree of protective immunity;

ii) the protective efficacy obtained in vaccination with BCG varies between 0 to 80% (Snider, 1994) and in addition iii) BCG vaccination has detrimental side-effects being partially responsible for tissue destruction in patients, without offering sufficient protection (Fine, 1994).

The unsatisfactory results observed and reported in a number of countries with the BCG vaccine currently used for the prevention of the spread of tuberculosis (Dolin, Raviglione and Koch, 1994; Snider, 1994) could be explained by:

i) variations between BCG vaccines, which could be caused by strain variation or by differences between manufacturing processes;

ii) differences in pathogenesis of *Mycobacterium tuberculosis;* iii) differences in the exposure to the environmental mycobacteria. The environmental mycobacteria may act antagonistically or synergistically with BCG;

iv) genetic differences between population groups subjected to vaccination with BCG;

v) differences in nutrition and exposure to sunlight between various population groups;

vi) differences between designs of various studies;

vii) inadequacies of the criteria used for the evaluation of protective effects of vaccination with BCG.

Efforts directed at finding an effective vaccine capable of inducing long-lasting immunity have centered over the last decade on three main approaches:

i) identifying "protective" antigens and epitopes of *M. tuberculosis* presented by macrophages and recognized by human lymphocytes;

ii) developing a DNA-based vaccine with protective antigen and interleukin genes (Lowrie et al., 1994);

iii) identifying which types of cells of the immune system and which types of cytokines are involved in tuberculosis in order to manipulate their activity towards offering a cure or protection against tuberculosis.

SUMMARY OF THE INVENTION

According to one aspect of the invention there is provided a conjugate comprising an organic carrier and a purified lipid cell-wall component associated therewith, provided that if the organic carrier is a protein, it is not bovine serum albumin (BSA), gelatin, keyhole limpets haemocyanin or the $CD_1$ molecule.

The organic carrier may be a protein excluding bovine serum albumin (BSA), gelatin, keyhole limpets haemocyanin and the $CD_1$ molecule.

The protein may be a microbial protein. More specifically, it may be a modified bacterial protein and may be derived from a bacterium from the genus Mycobacterium, Corynebacterium, Nocardia or Rhodococcus. It may be a heat-shock protein, such as heat-shock protein 60 (HSP60) or heat-shock protein 65 (HSP65), or it may be a serum protein from an animal. The animal may have a mycobacterial infection, such as a *Mycobacterium tuberculosis* infection. The animal may be a mammal, typically a human.

Alternatively, the protein may be derived from a mammal, particularly a human, and is preferably a protein which mimics the structure of collagen or a collagen-derived protein or a plasma protein, such as the collagen-like segment of human serum component $C1_q$.

Alternatively, the carrier may be a carbohydrate such as galactomannan or arabinogalactan or a lipopolysaccharide.

Further alternatively, the organic carrier may be a micelle, such as a liposome.

According to another aspect of the invention there is provided a diagnostic kit comprising a support containing a conjugate as described above immobilised thereon.

According to another aspect of the invention there is provided a pharmaceutical composition which comprises a therapeutic, prophylactic or tolerogenic amount of a conjugate as described above or a conjugate comprising any organic carrier and a purified lipid cell-wall component or analog or derivative thereof associated therewith or a biologically active purified lipid cell-wall component or analog or derivative thereof and a pharmaceutically acceptable or compatible pharmaceutical excipient, medium, carrier or adjuvant.

The organic carrier may be a protein including bovine serum albumin (BSA), gelatin, keyhole limpets haemocyanin and the CD1 molecule, or may be a carbohydrate or may be a micelle.

The pharmaceutical composition may also contain at least one immunomodulator. The immunomodulator may be a cytokine. The cytokine may be an interleukin, such as interleukin 4 (IL4), interleukin 10 (IL10) or interleukin 12 (IL12), or may be an interferon.

The suitable pharmaceutical carrier or adjuvant which may also be suitable for veterinary applications may be a solid, such as polymer dust, a liquid, such as an oil, typically Marcol 52, or a water-in-oil emulsion, typically Freund's Incomplete Adjuvant (FIA), or a solution, typically a saline solution or PBS, in which case the composition may be in the form of a suspension or a vapourised liquid, typically a neubulisable physiological saline solution, or a gas, or a transdermal delivery system.

The composition may comprise a therapeutic, prophylactic or tolerogenic amount of the purified lipid cell-wall component.

The pharmaceutical composition may comprise about 5 $\mu$g or less, typically 1 $\mu$g, of the purified lipid cell-wall component per ml of the composition.

A unit dose of the pharmaceutical composition for administration to a human subject preferably comprises from about 5 to 10 mg of the purified lipid cell-wall component.

According to another aspect of the invention there is provided a vaccine containing a purified lipid cell-wall component or analog or derivative thereof or a conjugate or a pharmaceutical composition as described above or a conjugate comprising any organic carrier and a purified lipid cell-wall component associated therewith for use in preventing an immune disorder or an inflammatory condition in a subject.

According to another aspect of the invention there is provided a vaccine containing a purified lipid cell-wall component or analog or derivative thereof or a conjugate or a pharmaceutical composition as described above or a conjugate comprising any organic carrier, except bovine serum albumin (BSA) and a purified lipid cell-wall component associated therewith, for use in preventing a microbial infection in a subject.

The organic carrier may be a protein including bovine serum albumin (BSA), gelatin, keyhole limpets haemocyanin and the CD1 molecule, or may be a carbohydrate or may be a micelle.

According to another aspect of the invention there is provided an isolated antibody which is capable of forming, separately, an antigen/antibody complex with any two or more of the following antigens: a purified lipid cell-wall component derived from a microorganism: a protein derived from a bacterial species or from a mammal; a conjugate as described above; and a conjugate comprising any organic carrier and a purified mycobacterial lipid cell-wall component associated therewith.

The organic carrier may be a protein including bovine serum albumin (BSA), gelatin, keyhole limpets haemocyanin and the CD1 molecule, or may be a carbohydrate or may be a micelle.

According to another aspect of the invention there is provided a method of diagnosing a microbial infection in a subject comprising the step of contacting a sample from the subject with a conjugate as described above or with a support containing a conjugate as described above; and detecting any reaction between the conjugate and the sample.

More preferably, the method of diagnosis may comprise the step of detecting the binding of an antibody present in the sample to the conjugate.

According to another aspect of the invention there is provided a conjugate or a pharmaceutical composition as described above for use in a method of diagnosis of a microbial infection in a subject.

According to another aspect of the invention there is provided the use of a conjugate or a pharmaceutical composition as described above in a method of making a medicament for use in a method of diagnosis of a microbial infection in a subject.

According to another aspect of the invention there is provided a purified lipid cell-wall component or analog or derivative thereof or a conjugate or a pharmaceutical composition as described above or a conjugate comprising any organic carrier and a purified lipid cell-wall component associated therewith for use as a tolerogen to enhance resistance and/or reduce susceptibility to a microbial infection in a subject.

According to another aspect of the invention there is provided the use of a purified lipid cell-wall component or analog or derivative thereof or a conjugate or a pharmaceutical composition as described above or a conjugate comprising any organic carrier and purified lipid cell-wall component associated therewith in a method of making a medicament for use as a tolerogen to enhance resistance and/or reduce susceptibility to a microbial infection in a subject.

According to another aspect of the invention there is provided a purified lipid cell-wall component or analog or derivative thereof or a conjugate or a pharmaceutical composition as described above or a conjugate comprising any organic carrier and a purified lipid cell-wall component associated therewith for use in a method of enhancing resistance or lowering susceptibility to microbial infections in a subject.

According to another aspect of the invention there is provided use of a purified lipid cell-wall component or analog or derivative thereof or a conjugate or pharmaceutical composition as described above or a conjugate comprising any organic carrier and a purified lipid cell-wall component associated therewith in a method of making a medicament for use in enhancing resistance or lowering susceptibility to microbial infections in a subject.

According to another aspect of the invention there is provided a method of treatment of a microbial infection in a subject comprising the step of administering to the subject a purified bacterial lipid cell-wall component or analog or derivative thereof or a pharmaceutical composition of the invention to the subject.

According to another aspect of the invention there is provided a conjugate or a pharmaceutical composition as described above or a conjugate comprising any organic carrier and a purified lipid cell-wall component associated therewith or a purified lipid cell-wall component or analog or derivative thereof for use in a method of treatment of a microbial infection in a subject.

According to another aspect of the invention there is provided the use of a conjugate or pharmaceutical composition as described above or a conjugate comprising any organic carrier and a purified lipid cell-wall component associated therewith or a purified lipid cell-wall component or analog or derivative thereof in a method of making a medicament for use in a method of treatment of a microbial infection in a subject.

The organic carrier may be a protein including bovine serum albumin (BSA), gelatin, keyhole limpets haemocyanin and the CD1 molecule, or may be a carbohydrate or may be a micelle.

The method of treatment may be a prophylactic and/or therapeutic method and may be a high zone tolerance treatment or may be a low zone tolerance treatment or a treatment aiming at an idiotypic regulation involving the conjugate or the antibody.

The method may be an immunoregulatory method.

The method of treatment may be a prophylactic method which enhances resistance or reduces susceptibility to a microbial infection in a subject. The prophylactic method may promote an inflammatory response in an infected organ, typically the lungs, kidney and/or liver of the subject. The infected organ is usually the lungs.

According to another aspect of the invention there is provided a method of treatment of an immune disorder in a subject comprising the step of administering to the subject a purified bacterial lipid cell-wall component or analog or derivative thereof or a pharmaceutical composition as described above.

According to another aspect of the invention there is provided a purified lipid cell-wall component or analog or derivative thereof or a conjugate or pharmaceutical composition as described above or a conjugate comprising any organic carrier and a purified lipid cell-wall component associated therewith for use in a method of treatment and/or diagnosis of an immune disorder in a subject.

According to another aspect of the invention there is provided the use of purified lipid cell-wall component or analog or derivative thereof or a conjugate or pharmaceutical composition as described above or a conjugate comprising any organic carrier and a purified lipid cell-wall component associated therewith in a method of making a medicament for use in a method of treatment and/or diagnosis of an autoimmune disease in a subject.

The organic carrier may be a protein including bovine serum albumin (BSA), gelatin, keyhole limpets haemocyanin and the CD1 molecule, or may be a carbohydrate or may be a micelle.

According to another aspect of the invention there is provided a purified lipid cell-wall component or analog or derivative thereof or a conjugate or pharmaceutical composition as described above or a conjugate comprising any organic carrier and a purified lipid cell-wall component associated therewith for use in a method of treatment and/or diagnosis of an inflammatory condition in a subject.

According to another aspect of the invention there is provided the use of a purified lipid cell-wall component or analog or derivative thereof or a conjugate or pharmaceutical composition as described above or a conjugate comprising any organic carrier and a purified lipid cell-wall component associated therewith in a method of making a medicament for use in a method of treatment and/or diagnosis of an inflammatory condition in a subject.

The organic carrier may be a protein including bovine serum albumin (BSA), gelatin, keyhole limpets haemocyanin and the CD1 molecule, or may be a carbohydrate or may be a micelle.

According to another aspect of the invention there is provided a method of diagnosing an immune disorder in a subject comprising the step of contacting a sample from the subject with a purified lipid cell-wall component or analog or derivative thereof or with a pharmaceutical composition as described above or with a conjugate as described above or with a conjugate comprising any organic carrier and a purified lipid cell-wall component associated therewith or with a support containing either conjugate; and detecting any reaction between the purified lipid cell-wall component or conjugate and the sample.

More preferably, the method of diagnosis may comprise the step of detecting the binding of an antibody present in the sample to the purified lipid cell-wall component or the conjugate.

The organic carrier may be a protein including bovine serum albumin (BSA), gelatin, keyhole limpets haemocyanin and the CD1 molecule, or may be a carbohydrate or may be a micelle.

According to another aspect of the invention there is provided a purified lipid cell-wall component or analog or derivative thereof or a conjugate or a pharmaceutical composition as described above or a conjugate comprising any organic carrier and a purified lipid cell-wall component associated therewith for use as a toleragen to enhance resistance and/or reduce susceptibility to an immune disorder or an inflammatory condition in a subject.

According to another aspect of the invention there is provided the use of a purified lipid cell-wall component or analog or derivative thereof or a conjugate or a pharmaceutical composition as described above or a conjugate comprising any organic carrier and a purified lipid cell-wall component associated therewith for use in a method of making a medicament as a tolerogen to enhance resistance and/or reduce susceptibility to an immune disorder or an inflammatory condition in a subject.

The organic carrier may be a protein including bovine serum albumin (BSA), gelatins keyhole limpets haemocyanin and the CD1 molecule, or may be a carbohydrate or may be a micelle.

According to another aspect of the invention there is provided a purified lipid cell-wall component or analog or derivative thereof or a conjugate or a pharmaceutical composition as described above or a conjugate comprising any organic carrier, except bovine serum albumin (BSA), and a purified lipid cell-wall component associated therewith for use in a method of modulating or manipulating the humoral immune system in a subject for the treatment or prophylaxis of a microbial infection, an immune disorder or an inflammatory condition in a subject.

According to another aspect of the invention there is provided the use of a conjugate or a pharmaceutical composition as described above or a conjugate comprising any organic carrier, except bovine serum albumin (BSA), and a purified lipid cell-wall component associated therewith in a method of making a medicament for use in a method of modulating or manipulating the humoral immune system in a subject for the treatment or prophylaxis of a microbial infection, an immune disorder or an inflammatory condition in a subject.

The organic carrier may be a protein including gelatin, keyhole limpets haemocyanin and the CD1 molecule, or may be a carbohydrate or may be a micelle.

According to another aspect of the invention there is provided a purified lipid cell-wall component or analog or derivative thereof or a conjugate or pharmaceutical composition as described above or a conjugate comprising any organic carrier and a purified lipid cell-wall component associated therewith for use in a method of enhancing resistance or lowering susceptibility to inflammatory conditions or allergies in a subject.

According to another aspect of the invention there is provided use of a purified lipid cell-wall component or analog or derivative thereof or a conjugate or pharmaceutical composition as described above or a conjugate comprising any organic carrier and a purified lipid cell-wall component associated therewith in a method of making a medicament for use in enhancing resistance or lowering susceptibility to inflammatory conditions and/or allergies in a subject.

The organic carrier may be a protein including bovine serum albumin (BSA), gelatin, keyhole limpets haemocyanin, the CD1 molecule and a serum protein, or may be a carbohydrate or may be a micelle.

The method of treatment may be a prophylactic and/or therapeutic method and may be a high zone tolerance treatment or may be a low zone tolerance treatment or a treatment aiming at an idiotypic regulation involving the conjugate or the antibody.

The method may be an immunoregulatory method.

The method of treatment may be a prophylactic method which enhances resistance or reduces susceptibility to an immune disorder, inflammatory condition or allergy in a subject. The prophylactic method may suppress inflammation in the joints of the subject.

According to another aspect of the invention there is provided a purified lipid cell-wall component or analog or derivative thereof or a conjugate or a pharmaceutical composition as described above or a conjugate comprising any organic carrier and a purified lipid cell-wall component associated therewith for use in the method of modulating or manipulating the cellular immune system in a subject for the treatment or prophylaxis of a microbial infection, an immune disorder or an inflammatory condition in a subject.

According to another aspect of the invention there is provided a purified lipid cell-wall component or analog or derivative thereof or a conjugate or a pharmaceutical composition as described above or a conjugate comprising any organic carrier and a purified lipid cell-wall component associated therewith in a method of making a medicament for use in a method of modulating or manipulating the cellular immune system in a subject for the treatment or prophylaxis of a microbial infection, an immune disorder or an inflammatory condition in a subject.

The organic carrier may be a protein including bovine serum albumin (BSA), gelatin, keyhole limpets haemocyanin and the CD1 molecule, or may be a carbohydrate or may be a micelle.

More particularly, the modulation or manipulation of the immune system may be the modulation or manipulation of T-cell effects, such as $CD4^+$, Th0, Th1 and Th2, $CD8^+$ or $CD4^-CD8^-$ (double negative (DN)) T-cells, natural killer (NK) cells, and/or of macrophages.

According to another aspect of the invention there is provided use of a purified lipid cell-wall component in a method of forming a conjugate comprising any organic carrier and the purified lipid cell-wall component, whether the conjugate is produced in vitro or in vivo.

The purified lipid cell-wall component as referred to herein is preferably a bacterial cell-wall component from a bacterium which produces mycolic acids and it may be derived from the genus Mycobacterium, Corynebacterium, Nocardia or Rhodococcus.

The bacterium is preferably *Mycobacterium tuberculosis*.

More preferably, the purified lipid cell-wall component is a purified mycolic acid, a mixture of purified mycolic acids or a mycolic acids fraction or derivative originating from a single or different species or a synthetic source. Other lipid cell-wall components may be high molecular weight lipids such as cord factors.

The purified lipid cell-wall component may be a biologically active purified mycolic acid, a mixture of biologically active purified mycolic acids or a biologically active purified mycolic acids fraction or derivative originating from a single or different species or a synthetic source.

The purified lipid cell-wall component may be a resaponified biologically active mycolic acid, a mixture of resaponified biologically active mycolic acids or a biologically active mycolic acids fraction or derivative of resaponified mycolic acids.

The derivative of the purified lipid cell-wall component as referred to herein may be an ester of a mycolic acid, a mixture of esters of mycolic acids or a derivative or fraction thereof.

The microbial infection as referred to herein may be a mycobacterial infection, typically tuberculosis or leprosy.

The immune disorder as referred to herein may be an inflammatory condition. It may be an autoimmune disorder, typically arthritis.

The autoimmune disorder may be of mycobacterial origin.

According to yet another aspect of the invention there is provided a method of separating and purifying a specific microbial cell-wall component of a lipid or carbohydrate nature or a derivative or analog thereof from an extracted mixture of the cell-wall component or derivative or analog thereof and contaminants or from a synthetic mixture of the cell-wall component or derivative or analog thereof and contaminants comprising the steps of:

dissolving the extracted mixture or synthetic mixture in a bi-phasic solvent containing sodium chloride to form a solution;

allowing the solution to separate to form an upper phase and a lower phase;

subjecting the phases to countercurrent distribution/separation comprising a required number of cycles to separate the microbial cell-wall component or analog or derivative thereof in the upper phase or the lower phase; and removing the separated microbial cell-wall component or derivative or analog thereof from the upper or lower phase.

The method may also comprise the additional pre-purification steps of:

dissolving the extracted mixture of cell-wall component or derivative or analog thereof and contaminants or the synthetic mixture of the cell-wall component or derivative or analog thereof and contaminants in a first solvent without sodium chloride;

adding thereto a second solvent without sodium chloride;

mixing and allowing the solution to separate to form a first upper phase (second solvent) and a first lower phase (first solvent); and removing the first upper phase and/or the first lower phase for further processing.

Preferably, the lower phase or first lower phase, containing the extracted mixture, is removed and subjected to countercurrent distribution purification, as described above.

The method may also comprise the additional post-purification steps of:

dissolving the extracted microbial cell-wall component or derivative or analog thereof in a suitable solvent; and adding a precipitant to the solution to precipitate out the dissolved further purified microbial cell-wall component or derivative or analog thereof.

The solvent is preferably chloroform.

The precipitant is preferably acetone.

The method may comprise the steps of:

saponifying a microbial culture prior to preparing therefrom an extracted mixture of a cell-wall component or derivative or analog thereof on which to perform the method of the invention; and resaponifying the separated and purified microbial cell-wall component or derivative or analog thereof.

According to yet another aspect of the invention a purified mycolic acid or mixture of purified mycolic acids or a fraction thereof is provided in a particular conformation that renders it biologically active.

The purified mycolic acid or mixture of purified mycolic acids may be in a conformation produced by the purified mycolic acid or mixture of purified mycolic acids being in a methyl ester form or a freshly resaponified form.

According to yet another aspect of the invention there is provided a method of preparing detection means for detecting the presence of anti-mycolic acids antibodies, the detection means comprising a solid phase and mycolic acids in a methyl ester form or in a freshly resaponified form associated therewith.

The solid phase may be an ELISA plate.

DESCRIPTION OF PREFERRED EMBODIMENTS

Figure 1:
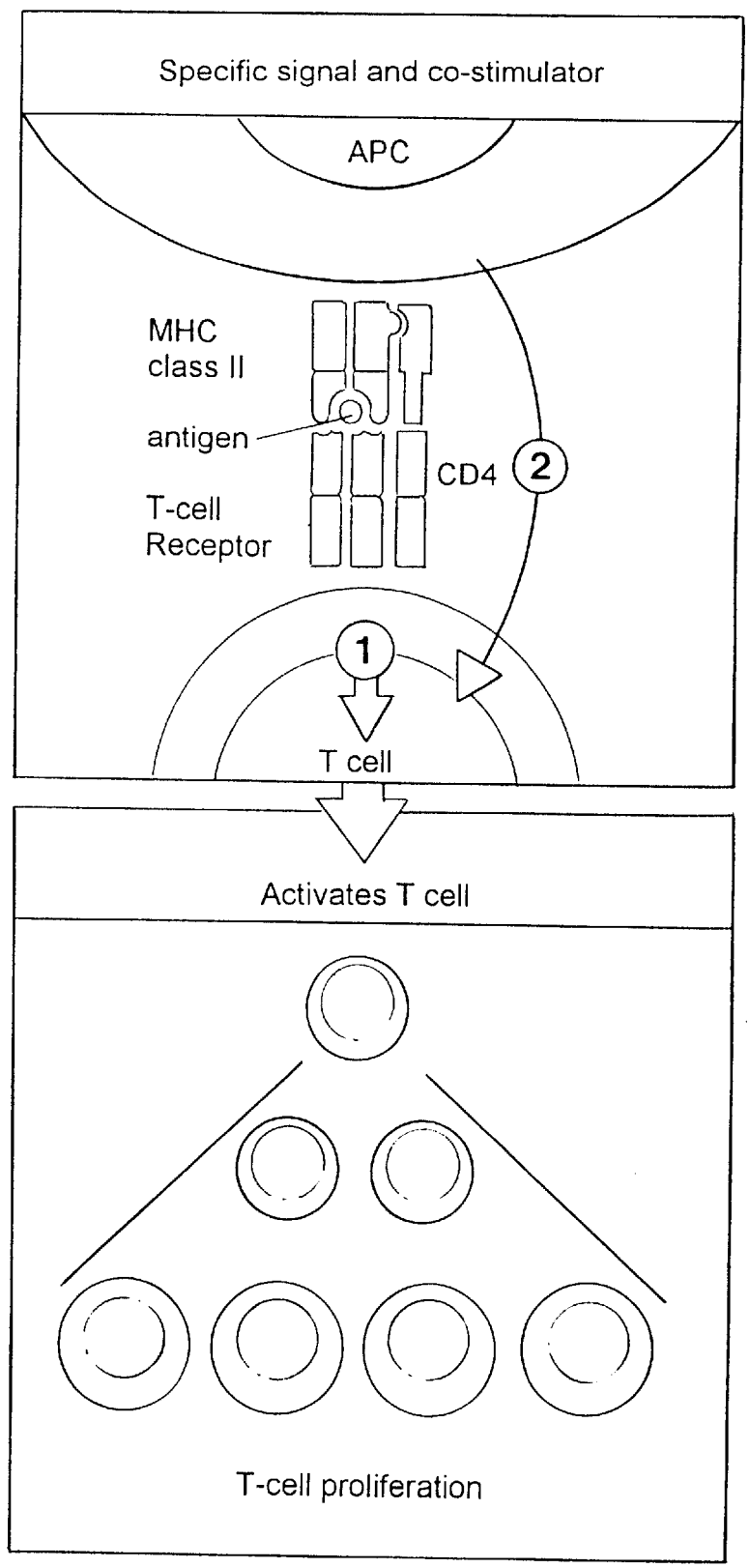
FIG. 1 is a schematic presentation of the activation process of naive T-cells.

This invention is based on the involvement of isolated, purified, biologically active mycobacterial lipid cell-wall components, and more particularly purified, biologically active mycolic acids or analogs or derivatives thereof, in the regulation of the immune response in a subject or host to infection or abnormal activation. These purified mycobacterial lipid cell-wall components originate from bacteria assigned to the genus *M. mycobacterium* and to the genera Corynebacterium, Nocardia and Rhodococcus. In particular, the present invention teaches the application of isolated and purified mycolic acids in:

1. the modulation and immunoregulation of an immune response towards infection with mycobacteria in humans and animals;
2. the development of anti-tuberculosis and other anti-mycobacterial treatment for human and veterinary use. It is envisaged that tolerogenic doses of the purified lipid cell-wall components of *M. tuberculosis* and other Mycobacteria, on their own or presented on carriers such as proteins, liposomes or carbohydrates or in a medium or pharmaceutical carrier or excipient such as liquid (oil, saline, water) gas or vapour, could be used in the modulation of immune responses to mycobacterial infections;
3. the development and production of diagnostic tests (in vitro and/or in vivo tests) for the confirmation of the presence of mycobacterial cells in samples such as blood, cerebrospinal fluid, tears and saliva or tests that would be based on the identification and detection of auto-reactive antibodies and/or T-cells, and antibodies against the purified lipid cell-wall components with or without host carriers;
4. the prevention and immunotherapy and regulation of autoimmune illnesses of mycobacterial and other origin and particularly those associated with infection with mycobacteria. Such a therapy could be achieved by modulating the immune response directed against mycobacterial lipid cell-wall components. It is envisaged that the tolerogenic doses of the purified lipid cell-wall components of *M. tuberculosis* and other Mycobacteria presented in a supportive medium or in a pharmaceutically acceptable carrier or excipient or on carriers such as liposomes or proteins or suspended in an adjuvant, typically a water-in-oil emulsion such as FIA, can be used for the regulation of immune responses to mycobacterial antigens leading to the prevention of tuberculosis and auto-immune diseases such as arthritis, often associated with tuberculosis.

The invention utilises the method of isolation and purification of a mycobacterial lipid cell-wall component described in South African Patent No. 96/1412 and is based on the demonstration of the immunogenicity of mycolic acids described in South African Patent No. 95/3077.

The invention also provides an improvement on the method of isolation and purification of mycobacterial lipid cell-wall components described in South African Patent No. 96/1412. An improvement involves a preliminary purification of crude mycobacterial extract to remove redundant or unnecessary cellular components prior to the countercurrent purification and to reduce the soap content in the crude extract. A further improvement to the method involves the addition of sodium chloride to the solvent. This allows larger amounts of the extracted mycolic acids to be purified per run of the countercurrent separation.

The availability of the isolated and purified required components, particularly mycolic acids, is essential for the development and assessment of the potential applications listed above.

As indicated above, the conventional approaches to the prevention of infection with *M. tuberculosis* by attempting to induce humoral and/or cellular memory leading to a long-term protection against tuberculosis have been unsuccessful. The present invention offers another approach. It is based in part on the use of appropriate tolerogenic doses of mycolic acids in a supportive medium or pharmaceutically acceptable carriers or excipients or on appropriate carriers, with or without appropriate interleukine(s) (Heath and Playfair, 1992), to modulate/regulate the immune response (s) in the human body. Such a treatment would help to prevent or decrease mortality due to tuberculosis and could be used as a potential treatment for the disease.

The presentation of purified mycolic acids in supportive media, conjugates, pharmaceutical compositions comprising pharmaceutically acceptable excipients, carriers and adjuvants, uses and methods of the invention should be considered in the light of what is known about the pathology of tuberculosis as described below.

The encounter between the bacterium *Mycobacterium tuberculosis* and its human host is exceptionally complex and multifaceted and leads to a number of intertwined, interdependent and interconnected processes, in which mycolic acids appear to be playing a significant role. For the sake of clarity these processes will be discussed under the following headings:

Outline: Clinical Stages of Tuberculosis

1. Primary pulmonary tuberculosis
2. Post-primary pulmonary/reactivation tuberculosis
3. Immunology/immunopathology in tuberculosis
   - 3.1 Overview
   - 3.2 Synthesis of cytokines
   - 3.3 Activation of macrophages and the intracellular fate of *M. tuberculosis*
   - 3.4 Delayed-Type Hypersensitivity (DI)

3.5 Activation of T cells and their functions
3.6 Cytokine circuits in tuberculosis
3.7 Cytokine induction by *M. tuberculosis*
3.8 Cytokine profiles in tuberculosis patients
3.9 Involvement of other T cells in tuberculosis
4. Proposed approach
5. Immunogenicity of mycolic acids
OUTLINE: Clinical Stages of Tuberculosis
1. Primary Pulmonary Tuberculosis It is generally accepted that the primary infection with *M. tuberculosis* occurs by inhalation of a very small number of bacilli into the respiratory tract. Usually fewer than 10% of the inhaled microorganisms reach the respiratory bronchioles and alveoli, the rest being successfully removed from th upper respiratory epithelium by the nonspecific, external innate immunity, i.e., by mucus and the ciliated epithelium of the upper respiratory tract acting as filters. Mycobacteria that reach alveoli are dealt with by the internal innate immunity mechanism. In the case of the mycobacterial infection, phagocytosis (engulfment and destruction of the pathogens by mononuclear leucocytes) and inflammatory reaction play the decisive part. The age of an individual, general stare of his/her health, conditions of living, nutrition as well as ethnic and geographic differences affect the susceptibility to the disease and its severity (Fine, 1994).

The inhaled cells of *M. tuberculosis* are ingested by alveolar macrophages (see section 3.3 on the activation of macrophages), which have a predilection for this function. Some of the bacilli are destroyed within the phagolysosomes of the macrophages and some remain in the macrophagal vacuoles for undetermined periods of time. In some cases, even replication of the bacilli may occur in the macrophage's vacuoles. Within the period of 2 to 3 weeks some of the surviving bacteria destroy their host macrophages and, after being released, can infect additional macrophages (Fenton and Vermeulen, 1996).

The chemotactic factors released by the destroyed macrophages attract other leucocytes: monocytes, lymphocytes and neutrophils, which are not capable of destroying the released mycobacteria. The accumulation of lymphocytes and the formation of macrophage-derived epitheloid giant cells constitute the beginning of the inflammation process (see section 3.1 and 3.3) and lead to the formation of nodules called granulomas, which in the case of tuberculosis are referred to as tubercles. The degree of success of granuloma formation depends on the initial number of mycobacteria present in the tissue and on the number of macrophages present at the site of infection (Fenton and Vermeulen, 1996).

The formation of granulomas is a result of an interaction between the macrophages and T lymphocytes and the secretion of proteins stimulating cells of both types. It constitutes the beginning of the development of cell-mediated immunity (for a detailed description see section 3.4). Although the cells of ingested *M. tuberculosis* are not always completely destroyed, the formation of granuloma is an effective defense mechanism of "containing"/walling-off the pathogens, which stops the infection from spreading further and retains it in a subclinical state. If, however, the resistance of the infected person is low, the formation of granulomas may not stop the growth and spread of the mycobacteria and the disease progresses further to primary clinical tuberculosis.

During this stage of the disease more tubercles are formed and they become larger. A hypersensitivity reaction (see section 3.4) accompanied by tissue necrosis and fusion of the dead macrophages constitute the characteristic response.

The fusion of macrophages leads to the formation of caseation necrosis within the granulomas. In the majority of cases, in order to seal off the necrotic site, lymphocytes and other cells collect at the site and form a fibrous tissue. The walled-off caseated granulomas frequently heal over time, shrink and calcify. The disease frequently stops at this stage and tile damaged lung tissue, detected by X-ray, remains the proof of the successfully combated disease. In the majority of cases the encounter between mycobacteria and the human immune system stops here and as a result of this exposure, most individuals successfully control the focus of infection and develop some degree of immunity.

If, however, the healing process is impaired, the lesions do not calcify but expand, eroding adjacent bronchi and leading to the formation of cavities, in which live cells of *M. tuberculosis* can multiply freely, sometimes reaching numbers exceeding $10^8$ per cavity (Nardell, 1993). Living mycobacteria can leak from such open cavities directly into bronchia leading to even further spread of the disease and a continuous discharge of these bacilli into the sputum. The leaked bacilli can be inhaled into other parts of the host's lungs resulting in tuberculous bronchopneumonia. As the caseation necrosis develops further and spreads, the patient starts to display the clinical symptoms of tuberculosis such as loss of weight, night sweats, persistent cough, loss of appetite and fatigue. At this stage an intensive therapy is required (Fenton and Vermeulen, 1996).

If mycobacteria spread to the blood, they can localise in any organ forming new tubercles and the disease becomes a generalised form of tuberculosis, referred to as miliary tuberculosis.

2. Post-primary Pulmonary/Reactivation Tuberculosis

Post-primary pulmonary tuberculosis or reactivation tuberculosis can develop following either inhalation of additional mycobacteria or by reactivation of a dormant primary lesion, in which bacilli can survive in a dormant state for decades. The post-primary tuberculosis progresses despite the existing immunity developed during the primary exposure (Fenton and Vermeulen, 1996) and is considered to be the most prevalent form of the disease (Elgert, 1996a). It usually occurs concomitantly with a period of excessive environmental stress, malnutrition or lowering of immune competence of the body.

The pathogen, no longer held in check within the tubercles, multiplies vigorously and leads to the development of symptoms observed in the primary clinical tuberculosis. Generalized clinical tuberculosis causes damage to various vital organs and can result in death of the patient.

3. Immunology/Immunopathology in Tuberculosis 3.1 Overview

Although the breaking down and digestion of mycobacteria by macrophages is considered to be essentially a non-antigen-specific process, it initiates the development of the adaptive, i.e., antigen-specific immune responses, which develop after about 3 weeks since the initial exposure to *M. tuberculosis* and significantly contribute to the combating of the infection. Certain components of the macrophage-digested bacilli, after being released from the phagolysosomes, are transported by specialised proteins referred to as major histocompatibility molecules (MHC molecules) to the surface of the macrophages, where they can be recognised by T lymphocytes (for details see section 3.3). If any of the presented components of *M. tuberculosis* is recognised by a T cell, certain proteins called cytokines*) (see section 3.2) capable of initiating the proliferation of the T cell into a clone of cells recognising this particular antigen, are synthesized and secreted.

*) Small protein molecules via which the communication between various parts and various cells of the immune system is accomplished.

The mycobacterial antigens presented by the infected macrophages attract specific T cells and the process of inflammation leading to the formation of granulomas is initiated. The antigen recognition which takes place is due to the complementarity of the combining sites between the {MHC-*M. tuberculosis* component}-complex presented on the surface of the macrophage and the receptors present on the T cell. The interaction between the T cells and macrophages leads to the stimulation/activation of macrophages (for details see section 3.3) which start secreting various cytokines. One of the cytokines produced by the activated macrophage, interleukin 1 (IL-1), induces the proliferation of neighbouring T cells (inflammatory CD4 T cells), which in turn start secreting interferon γ (IFN-γ). IFN-γ acting as a chemotaxin, attracts monocytes to the site of infection and converts resting monocytes into activated macrophages (Fenton and Vermeulen, 1996; Elgert, 1996b).

The further course of the disease depends to a large degree upon the type of the activated lymphocyte, i.e., whether it is a cytotoxic (CD8) or a helper (CD4) T cell, or whether T-helper cell is a T-helper 1 (Th1) or a T-helper-2 (Th2) type. The stimulation of CD8 or CD4 T cells depends on whether an antigen presenting cell (APC) presented the antigen in association with a major histocompatibility complex (MHC) molecule of class I or MHC class II, respectively. The mechanism of the selection between Th1 or Th2 type T-cell response is less clearly understood.

On the basis of the accumulated evidence it appears that the activated macrophages and Th1 CD4 cells play the most important role in the immune response to tuberculosis, leading to the development of acute phase inflammatory response i.e., the development of delayed-type hypersensitivity (DTH) (see section 3.4) and the formation of granulomas. The Th1 cells are known to secrete, apart from IL-2, interferon γ, in response to IL-12 secretion by activated macrophages. INF-γ as the principal cytokine activating macrophages is of critical importance in combating intracellular mycobacterial infection (Toossi, 1996; Kaufmann, 1995a and 1995b).

The involvement of CD4 cells of the Th2 type, which activate B cells and induce the production of antibodies, has also been confirmed in tuberculosis (Grange, 1984; Fine, 1994). Although a number of various antibodies reactive with different types of mycobacterial antigens have been detected in the sera of tuberculosis patients (Grange, 1984; Dolin, Raviglione and Koch, 1994; Snider, 1994), their protective role has not been demonstrated.

For a long time the activities of Th1 cells in tuberculosis have been associated with the "good" immunity resulting in the "containment" of the mycobacterial infection and leading to an optimistic prognosis, whereas the Th2 cells activities have been held responsible for the development of allergic reactions and consequently were considered to be a "bad" type of immunity in this disease. The current approach considers the activities of Th2 cells as more positive and assigns to them a regulating function, which allows them to terminate the defence reactions initiated by Th1 cells which, if left unchecked, could cause serious tissue damage (Kaufman, 1995a).

Furthermore, the importance of the initial innate immunity and the decisive role it plays in the differentiation of T helper cells (Th0) to Th1 and Th2 cells has become better understood. The balance between macrophage-activating and -deactivating cytokines determines the outcome of the infection (Toossi, 1996; Kaufmann, 1995a and 1995b). Secretion of IL-12 by the infected macrophages and the production of IFN-γ by NK cells leads to the development of Th1 cells which initially offer protection against the pathogen. On the other hand, mycobacteria are potent inducers of IL-10 which inhibits the Th1 response to this pathogen, probably by inhibiting the synthesis of IFN-γ by NK cells, and has a wide range of effects on antigen-presenting cells. IL-10 has suppressive function, downregulates the major histocompatibility complex molecules and inhibits the production of monokines (Gong et al., 1996) The intracellular bacteria within the macrophage also appear to suppress the early production of IL-4 by $CD4^+NK1^+$cells. Therefore if, at the early stage of the infection when innate immunity plays a critical part, the production of IL-10 by macrophages and of IL-4 by $CD4^+NK1^+$takes place, the differentiation of T cells will be biased towards the premature development of Th2 cells with detrimental effects on the prognosis of the illness (Kaufmann, 1995a).

3.2 Synthesis of Cytokines

Cytokines—general

Cytokines are low molecular weight, soluble proteins which are transiently produced by some cells upon their activation and which specifically affect the behaviour of other cells. They act at picomolar to nanomolar concentrations on cytokine receptors inducing significant effects on the proliferation and function of a variety of cells involved in eliciting an adaptive immune response (Elgert, 1996b). Cytokines are regulatory and effector molecules which induce signal transduction, activation of genes responsible for growth, differentiation and cell activity.

Cytokines can act as regulators of cell functions by binding to specific, high-affinity receptors on the cells they affect. Cytokines are produced by T and B lymphocytes, NK cells, macrophages and granulocytes. The term interleukins is used for the molecules secreted by lymphoid cells which allow them to communicate with each other. Currently some 60 cytokines are known. A list of the more important of them, i.e., those involved in the "cytokine cascades" and in the "cytokine regulatory network" in tuberculosis, is given in Table 1.

A large panel of monoclonal antibodies specific for human and mouse cytokines, cytokine receptors and cell-surface differentiation antigens has been established. These antibodies constitute powerful probes for analyzing the roles played by different cytokines as intercellular regulators and effector molecules used by lymphocyte populations to mediate protective natural and specific immune responses to foreign antigens, e.g. bacteria, viruses and neoplasms.

Cytokine production by lymphocytes is restricted due to the instability of their respective mRNA. The mRNA instability is caused by the presence of an "instability sequence" in their 3' untranslated region (Janeway and Travers, 1994a). This allows the strict control of cytokine production and release. The stabilization of mRNA increases the synthesis of the cytokines by 20 to 30-fold.

The production of IL-2 is a decisive factor determining whether a T cell will proliferate and become a functional effector cell. The interaction of IL-2 with its receptor enhances clonal expansion of CD4 memory T cells at the site of active infections. These cells, in contrast to naive CD4 T cells are capable of producing and secreting IFN-γ. The production of IL-2 and other cytokines depends on the induction of several transcription factors (Janeway and Travers, 1994a). The induction of these factors is in turn initiated by the recognition of a specific antigen by the T cell. One of these factors, nuclear factor of activation (NF-AT), activates IL-2 transcription by binding to the promoter region of the IL-2 gene. However, this event on its own will not result in the production of IL-2, for which an additional binding of CD28 (a receptor molecule of Th cells) by B7 protein or APC is required. A signal which stabilizes IL-2 MRNA is passed through CD28. The stabilization of IL-2 MRNA together with the ligand binding of CD28 leads to the increase in the production of IL-2 by 100-fold (Janeway and Travers, 1994a). However, if the recognition of a specific antigen by a T cell is not accompanied by co-stimulation through CD28 molecule, the amount of IL-2 produced is minimal and T cells are not stimulated.

lysosomal enzymes and reactive nitrogen intermediates. Sufficient evidence has been accumulated to support the observation that *M. tuberculosis* bacilli have the ability to block the fusion of mycobacterium-containing phagosomes (acidic phagocytic vacuoles) with lysosomes (organelles containing hydrolytic enzymes) (McDonough, Kress and Bloom, 1993) and the ability to disrupt the normal functioning of phagosomes (Rastogi, Bachelet and Carvalho de Sousa, 1992). It is generally accepted that the ability of *M. tuberculosis* to survive and multiply within the macrophages is linked to the unusual physicochemical properties of the mycobacterial cell wall, attributed mainly to the lipid and lipid-associated components.

TABLE 1

Major cytokines (based on Elgert 1996b)

| Abbreviation | Aliases | Functions |
|---|---|---|
| IL-1($\alpha + \beta$) | Interleukin-1 ($\alpha + \beta$) | Induces thymocytes, T-cell and B-cell proliferation; Acts as a co-factor during antigenic and mitogenic stimulation; Increases secretion of other cytokines, e.g.IL-2, IL-4. CSF; Increases expression of IL-2 receptors; Induces maturation of pre-B-cells |
| IL-2 | Interleukin-2 | Stimulates T-cell growth; Co-stimulates B-cell differentiation |
| IL-3 | Interleukin-3 | Stimulates multipotential haemopoietic cell growth; Stimulates mast cell growth |
| IL-4 | Interleukin-4 | Co-stimulates B-cell differentiation; Stimulates class II MHC molecule expression on B cells and macrophages; Synergizes (with IL-3) in mast cell growth; Enhances IgG, and IgE production; Co-stimulates proliferation of several haemopoietic progenitors |
| IL-8 | Interleukin-8 | Stimulates chemotaxis of neutrophils and T cells; Stimulates granulocytec activity |
| IL-10 | Interleukin-10 | Inhibits cytokine synthesis by Th1 cells and activated macrophages; T-cell growth factor; Cytotoxic T-cells differentiation factor |
| IL-12 | Interleukin-12 | Induces IFN$\gamma$ production by T and NK cells; Augments the cytotoxic activity of NK cells; Stimulates differentiation of $CD_4$ T cells to Th1 cells |
| IFN-$\gamma$ | Interferon-$\gamma$ | A potent immunoregulatory moleule; Cross-regulating factor between Th1 and Th2 T cells; Downregulating factor of Th2 T cells activity; A strong activating factor for macrophages; Increase of MHC I and II class molecule expression; Inhibition of intracellular bacterial and protrozoan growth; Activation of neutrophils, NK cells and vascular endothelial cells; Promotion of B- and T-cell differentiation; Stimulation of antibody production, particularly IgG2a; Stimulation of IL-1 and IL-2 synthesis |
| TNF-$\alpha$ | Tumour necrosis factor-$\alpha$ | Causes lysis of target cells; Activation of endothelial cells |
| GM-CSF | Granulocyte-macrophage colony stimulating factor | Induces localized haematopoiesis of monocytes and neutrophils; |
| TGF-$\beta$ | Transforming growth factor $\beta$ | Regulates the formation of extracellular matrix; Inhibits B-, T- and NK-cell activity |
| CSF | Colony stimulating factor | Induces stimulation of the growth of colonies of granulocytes and macrophages; Activation of mature macrophages |

The central role played by IL-2 in the adaptive immunity is reflected by the number of drugs designed to suppress undesirable immune responses and interfere with the synthesis of this interleukin. The examples of such drugs are: cyclosporin and rapamycin, administered in order to prevent tissue grafts rejection.

Another interleukin having a profound influence on the development of adaptive immunity is interleukin 12 (IL-12). It is a product of mononuclear phagocytes (macrophages) and plays a crucial role in the differentiation of T-helper cells, inducing the development of Th1 cells in vitro and in vivo (Flynn et al., 1995; Toossi, 1996), thus increasing the resistance to several intracellular pathogens in experimental mice (Flynn et al., 1995). IL-12 also enhances the production of IFN-$\gamma$ from T and NK cells (D'Andrea et al., 1992; Kobayashi et al., 1989, Toossi, 1996), increases their proliferation (Flynn et al., 1995) and enhances cytolytic activity of CD8 T and NK cells (Flynn et al., 1995; Kobayashi et al., 1989; Gately et al., 1994). On the other hand, cytokines such as TGF-$\beta$ and IL-10 inhibit the production and activity of IL-12, suppress the Th1 response and stimulate the development of intracellular infections (D'Andrea et al., 1992).

3.3 Activation of Macrophages and the Intracellular Fate of *M. tuberculosis*

Following phagocytosis the intracellular growth of mycobacteria depends on their ability to avoid destruction by Normally, activated macrophages have the ability to process the mycobacterial antigens and to transport them to the cell surface where they are presented in association with major histocompatibility complex (MHC) proteins. In this process, macrophages become antigen presenting cells (APCs).

Macrophage activation i.e., the induction of antibacterial mechanisms in macrophages, is initiated by the contact of the macrophage containing ingested *M. tuberculosis* with an inflammatory T cell.

Macrophages require two signals before becoming activated:

the macrophage-activating cytokine, interferon-$\gamma$ (IFN-$\gamma$) (interferons are cytokines that can induce cells to resist viral replication) and membrane-bound form of tissue necrotic factor $\alpha$ (TNF-$\alpha$) or a small amount of bacterial lipopolysacharide (Janeway and Travers, 1994a).

The first signal, which sensitizes the macrophage to the second signal, is delivered by inflammatory CD4 T cells. The second signal is delivered by membrane-bound molecules induced on effector CD4 T cells. As the process of cytokine synthesis and of the synthesis of cell-surface molecules mediating their effects requires several hours, the inflammatory CD4 T cells must adhere to their target macrophages for this period. The newly synthesised cytokines are transferred through the microvesicles to the site of contact between the CD4 T cell and the macrophage.

The activation of a macrophage through the stimulation with IFN-γ and the contact with CD4 T cell results in a series of biochemical responses, which enable the macrophage to become highly bactericidal. The activated macrophages:

i) fuse their lysosomes more efficiently to phagosomes, which leads to the exposure of the intracellular bacteria to a variety of destructive/bactericidal enzymes;

ii) secrete IL-12 (activating Th1 cells), IL-6, Il-8 and TNF-α;

iii) produce oxygen radicals—antibacterial agents;

iv) produce nitric oxide—an antibacterial agent;

v) produce antibacterial peptides;

vi) amplify the immune response by increasing the number of major histocompatibility molecules class II (MCH class II) and of TNF-α receptors on their surface;

vii) recruit other immune cells to the site of infection (Janeway and Travers, 1994a and 1994b; Tizard, 1995a; Fenton and Vermeulen, 1996).

The TNF-α further contributes to the INF-γ-activation of the macrophage particularly in the induction of nitric oxide. These functions aim at the destruction of the mycobacteria. However, if antigenic stimulation persists, the macrophages become chronically activated and produce additional cytokines, growth factors and lysosomal enzymes. The latter can attack and destroy the surrounding tissue (Janeway and Travers, 1994a) leading to the formation of pulmonary cavities.

The enhancement of the macrophage microbicidal activities can be brought about by T cells, especially CD4 αβ T cells which secrete IFN-γ and IL-2 (Orme, 1993). As the activities of TH1 CD4 cells are antigen specific, their involvement in the activation of macrophages serves as one of the numerous examples of the intertwining between the innate and specific adaptive immunity.

In addition, the activated macrophages produce and secrete other interleukins such as IL-6, Il-8, and tumour necrosis factor a (TNF-α). Il-8 attracts T cells and neutrophils, while IL-6 and IL-8 initiate the acute phase inflammatory response. TNF-α plays a particularly prominent part in the immune response to mycobacteria. The production of TNF-α is induced by the presence of lipoarabinomannan, a constituent of the mycobacterial cell wall (Toossi, 1996). By attracting monocytes to the site of infection, TNF-α is aiding the formation of granulomas, in which, owing to the anaerobic environment, the bacilli eventually die. Therefore, IL-8, IL-6 and TNF-α participate in the protection of the patient's tissues against the disease and lead to the "containment" of the disease.

3.4 Delayed-Type Hypersensitivity (DTH)

The cell-mediated immune reaction occurring in *M. tuberculosis* infection, in which the main effector cells are activated macrophages, is called delayed-type hypersensitivity (DTH) or type IV hypersensitivity. The tuberculin skin reaction (subcutaneous or intradermal contact with the concentrated derivatives of *M. tuberculosis*) is a classic example of the DTH reaction mediated through T cells (and cytokines produced by them) via activated macrophages (Elgert, 1996a).

The conversion from tuberculin-negative to tuberculin-positive skin reaction develops within six to eight weeks of infection (Boom, 1996) and frequently constitutes the first sign of the infection with *M. tuberculosis*. The second example of the DTH is the systemic granuloma formation resulting from the inflammatory reaction in tuberculosis.

The DTH reaction constitutes a part of the immune response to many intracellular infectious microorganisms, particularly those causing chronic diseases such as tuberculosis or leprosy. Although the development of DTH in tuberculosis involves sensitization rather than immunization of the infected person, nevertheless it results in a certain degree of protection.

With effective cellular immunity, the infection should be arrested permanently at this stage, with healed granulomas leaving small fibrous and calcified lesions and memory CD4 cells. If die cellular immune response is insufficient, macrophages containing viable cells of *M. tuberculosis* may escape via the intrapulmonary lymphatic vessels which may lead to the rapid spread of infection (Elgert, 1996a; Fenton and Vermeulen, 1996).

Although the precise mechanism for the development of the initiated DTH response remains not fully understood, the following has been established:

i) the interaction between the macrophage-processed and macrophage-presented antigen and the specific receptors present on CD4 T cells leads to the formation of sensitized inflammatory T helper cells, referred to as Th1 cells;

ii) a portion of Th1 cells become memory cells;

iii) on reactivation/restimulation Th1 cells produce a number of cytokines, the most important being:

1. IL-2, which causes the proliferation of antigen-primed Th1 cells;

2. GM-CSF, which induces localized haematopoiesis of monocytes and neutrophils;

3. TNF-α and -β which participate in endothelial cell binding and activation of leucocytes;

4. IFN-γ which is responsible for the enhanced expression of MHC proteins class II molecules on macrophages and endothelial cells as well as for the activation of macrophages (Elgert, 1996a; Fenton and Vermeulen, 1996).

In addition, chemotaxic factors (chemokines) such as interleukins of the IL-8 group may attract monocytes to the sites of antigen deposition and the TNF-β together with the macrophage-secreted TNF-α and IL-1 as well as IFN-γ induce and control the movement of leucocytes within the area of inflammation.

3.5 Activation of T Cells and Their Functions

Lymphocytes which have left the primary lymphoid organs, e.g. the thymus, and have never encountered their specific antigen and therefore have not responded to it, are referred to as naive T cells. The critical point in their development and in the development of the adaptive immune response is their activation. The activation is brought about by their contact with "professional" antigen-presenting cells (APC: macrophages, dendritic cells and B cells) and requires the concomitant presence of two independent signals (Janeway and Travers, 1994a and 1994 b). FIG. 1 presents a graphic illustration of this process.

The first signal is delivered by the binding of MHC-antigen complex to the T-cell antigen specific receptor and its co-receptor (either CD4 or CD8). This signal is transmitted by the T-cell co-receptor, indicating that the antigen has been recognised. The second co-stimulatory signal is delivered to the T cell by the same antigen-presenting cell, APC. The best characterised co-stimulatory molecules on APC are molecules called B7 and B7.2. The molecule on the surface of the T cell acting as a receptor for B7 is CD28 and the ligation of these two molecules will stimulate the proliferation of the particular clone of T cells. Subsequently, an additional receptor called CTLA-4 is expressed on the surface of the activated T cell and binds the B7 molecule with a higher affinity.

Naive T cells will respond to a particular antigen only when one APC cell presents both stimulatory signals: antigen specific to the. Tell receptor and a co-stimulating signal (B7, B7.2). Only APC possess the ability to express both classes of MHC molecules as well as to deliver a co-stimulatory signal and therefore to perform the so called "priming" of the naive T cells.

It is important to know that the T cells recognising the specific antigen in the absence of co-stimulatory signal, fail to produce IL-2, do not multiply and become anergic, i.e., unable to respond to a given antigen. This dual requirement for the proliferation of T cells is a preventative measure aimed at inhibiting the response of T cells to self tissues, which would be detrimental to the host. The phenomenon of anergy is frequently encountered in tuberculosis.

The interaction of T cells with APCs is influenced to a varying degree by a range of adhesion molecules such as selectins, integrins, some mucin-like molecules and CD44 molecule.

The activation of T cells by APCs results in their clonal proliferation leading to the production of large numbers of antigen-specific lymphocytes and the differentiation of their progeny into armed effector cells. The production of IL-2 is a decisive factor which determines whether a T cell will proliferate and differentiate into effector cells.

The antigen presentation takes place with the help of two classes of major histocompatibility molecules (MHC). MHC class I molecules present to CD8 T-cells antigens originating from the pathogens multiplying in the cytosol of the macrophages, thus initiating cellular or cell-mediated immune response. MHC molecules class II present antigens derived from ingested extracellular bacteria and toxins. These antigens are presented to CD4 inflammatory cells referred to as Th1 cells and to CD4 helper cells, referred to as Th2 cells. The Th2 cells activate the specific B cells, thus initiating the humoral immune response.

Once the T cells are activated and start the clonal expansion, they can act on any target cell which displays the specific antigen on its surface. Effector T cells can perform a number of functions such as:
i) killing of infected cells by CD8 cytotoxic T cells;
ii) activation of macrophages and peripheral mononuclear cells by CD4 inflammatory cells (an essential activity in tuberculosis leading to the destruction of the phagocytosed mycobacterial cells);
iii) activation of B cells to produce antibodies.

The first two activities constitute elements of cell-mediated immunity, whereas the third one represents the humoral immunity (Janeway and Travers, 1994a, 1994b and 1994c; Elgert, 1996c).

3.6 Cytokine Circuits in Tuberculosis

Experimental evidence accumulated so far indicates that the protective immune response against M tuberculosis in man is mediated primarily by CD4 Th1 cells and mononuclear phagocytes (Kaufmann, 1995a and 1995b, Fenton and Vermeulen, 1996, Boom, 1996). Among the cytokines secreted in the process of mounting host anti-mycobacterial responses, IL-12, IL-2 and IFN-γ appear to be playing the most prominent parts. The treatment of the M. tuberculosis-infected Balb/c mice with IL-12 effectively increased their survival and reduced 10 to 50-fold the number of viable bacilli in their organs (Flynn et al., 1995).

As there exists a distinct possibility of T-cell hyper-responsiveness at sites of active infection, the production of other cytokines which can inhibit the anti-mycobacterial immune responses such as transforming growth factor β (TGF-β) also takes place. The intricate interplay between various cytokine circuits which are activated by M. tuberculosis and its constituents may be amplified and contribute to pathology at the site of the infection (Toossi, 1996).

The overall outcome of the host immune response/host defence and the course of the disease will be determined by the balance between macrophage-activating and -deactivating cytokines. Some cytokines e.g. tumour necrosis factor Ca (TNF-α) and transforming growth factor β (TGF-β) may contribute to symptoms of tuberculosis such as tissue destruction, fibrosis formation, fever and weight loss. In addition, in the HIV-infected tuberculosis patients, cytokines may promote viral replication and in this way contribute to the progression of the disease.

The well documented role of IFN-γ in the infection with M. tuberculosis, becomes closer to be understood. The administration of IFN-γ to mice deficient in this cytokine prolongs their survival after the challenge with M. tuberculosis (Cooper et al., 1993; Flynn et al., 1993). The protective effects of IFN-γ appear to be due to the enhancement of macrophage activity towards M. tuberculosis, namely due to the upregulation of TNF-α and 1,25-hydroxy vitamin D (Bermudez and Young, 1988; Rook et al., 1987).

Both, IFN-γ and TNF-α increase anti-mycobacterial activity of human (Denis, 1991; Hirsch et al., 1994) and murine macrophages (Bermudez and Young, 1988). Both, IFN-γ and TNF-α counteract the effects of TGF-β. These effects interfere with the production of anti-mycobacterial nitrogen intermediaries within the infected macrophage and down-regulate IFN-γ and TNF-α. The balance between these three macrophage-activating and -deactivating cytokines, i.e., IFN-γ, TNF-α and TGF-β influences the final outcome of the infection (Chantry et al., 1989; Ding, Nathan and Srimal, 1990; Espevik et al., 1987; Tsunawki, Sporn and Nathan, 1988; Toossi, 1996).

3.7 Induction of Cytokines by M. tuberculosis' Antigens or Components

The currently available information concerning the involvement of M. tuberculosis' antigens or components on the induction of cytokines secretion (Toossi, 1996), can be summarized as follows:
i) both, partially purified and completely purified mycobacterial proteins were found to induce the production of Il -1, IL-2, IL-12, TGF-β and of TNF-α;
ii) the 38 kDa antigen was reported to induce the secretion of IL-12 and IFN-γ (Agrewala and Mishra, 1995) whereas the 58 kD antigen (present in the culture filtrate) was found to induce the production of TNF-α (Wallis, Paranjape and Phillips, 1993);
iii) two purified protein derivatives PPD1 and PPD2 were found to induce the production of IL-5 and IFN-γ, respectively (Ebtekar and Khanasri, 1996);
iv) the 30 kD antigen (a major secretory protein and cell-wall component) was found to induce cytokines in monocytes as well as the production of TGF-β (Toossi, 1996);
v) lipo-arabinomannan was found to be associated with the induction of TGF-β but not TNF-α, IL-1 or IL-10 (Toossi, 1996);
vi) heat-shock proteins studied, i.e., 10 kD, 65 kD and 71 kD molecules were found to induce proliferative responses in human $CD4^+$ T cells, with the 65-kDa molecule apparently playing part in human autoimmune responses (Boom, 1996; Beagly et al., 1993);

vii) some components of *M. tuberculosis*' cell walls were reported to induce potent immunosuppressive agents such as TGF-β (Toossi, 1996).

3.8 Cytokine Profiles in Tuberculosis Patients

Whereas in mice there exists a sequential production of Th1 and Th2 cytokines in response to live mycobacteria (Sander et al., 1995), in human tuberculosis there is an absence of a prominent Th2 cytokine response (Lin et al., 1996). Depressed Th1 cytokines responses, however, are characteristic of the advanced human tuberculosis, as illustrated by the following observations:

1. Several studies confirmed that tuberculosis sufferers display a defect in the production of IFN-γ when challenged with various mycobacterial antigens (Vilcek et al., 1986; Hirsch et al., 1996; Huygen et al., 1988; Onwubalili, Scott and Robinson, 1985);
2. The results observed in in vitro experiments indicate that CD4 lymphocytes originating from tuberculosis patients have a limited capacity to synthesise IL-2 and IFN-γ, when challenged with *M. tuberculosis* antigens (Toossi, 1996);
3. Lower peripheral blood mononuclear cell responses were reported and are thought to be caused by a functional suppression of T-cell production of IL-2 and expression of IL-2 receptors. The relative numbers of the two main populations/groups of T cells, namely CD4 and CD8, remain unchanged (Toossi, Kleinhenz and Ellner, 1986; Kleinhenz and Ellner, 1987; Vanham et al., 1996);
4. A dominant role played by monocytes in suppression of T-cell responses resulting in the lowering of the synthesis of IL-2 is well established (Ellner, 1978; Kleinhenz and Ellner, 1987; Toossi et al., 1989) and high numbers of these cells are frequently encountered in cases of active tuberculosis (Toossi, 1996). The molecular mechanisms by which monocytes suppress T-cell responses in patients with tuberculosis have been to a large degree elucidated and were discussed in a recent review by Toossi (1996);
5. Cytokines produced by CD4 cells belonging to Th2 subpopulations such as IL-4 and IL-10 are reported by some groups of researchers to be higher in patients with tuberculosis than in a control group (Sucrel et al., 1994; Toossi, 1996). However, there exists a certain degree of controversy on this subject (Hirsch et al., 1996, Toossi, 1996). As both of these cytokines have been associated with the ability to de-activate macrophages, their presence could adversely affect the course of the disease;
6. Transforming growth factor β (TGF-β) is a potent immunosuppressor that inhibits the clonal expansion of T cells by interfering with the proliferative signal of IL-2 and suppresses the production of INF-γ and IL-2 (even at femtomolar concentrations). TGF-β is known for its auto-induction, through which it can significantly increase its levels at sites of active tuberculosis infection. Through this action TGF-β can have a direct influence on several cytokines and seriously interfere with the host immune defense mechanisms.
7. Granulocyte-macrophage colony stimulating factor (GM-CSF) is secreted by macrophages and some T cells. GM-CSF, by acting directly on bone marrow cells, stimulates the expansion of granulocytes and macrophages. It influences, therefore, both humoral and cell-mediated immune responses (Boom, 1996).

3.9 Involvement of Other T Cells in Tuberculosis

Apart from the immune processes dependent on CD4 cells, CD8 T cells are also involved in the immune response to the infection with *M. tuberculosis*. As CD8 cells can be directly cytotoxic and have the ability to kill the macrophages harbouring mycobacteria, they play a part in the destruction of *M. tuberculosis*, either by lysis of the macrophages or by releasing of *M. tuberculosis* to the extracellular environment where they can be phagocytosed by other activated macrophages.

Recently carried out investigations indicate that additional subsets of T cells are involved in the immune reaction to tuberculosis. These T cells produced large amounts of IFN-γ and varying amounts of IL-2, IL4, IL-5 and IL-10, and cannot be assigned to the clearly defined Th1 or Th2 groups. They are classified as Th0 subset of CD4 cells (Boom, 1996).

Another subset of T cells which may have an important role in the cellular response to the infection with *M. tuberculosis* are the T cells expressing γδ T-cell receptor (Haanen et al., 1991; Boom, 1996; Kaufmann, 1995a). They have been reported to recognise phosphate-containing non-proteinaceous components of mycobacteria and, on stimulation with these components, have been shown to display a Th1 cytokine pattern (Kaufmann, 1995a). It has been postulated (Kaufmann, 1995a) that the rapid activation of γ/δ T cells, preceding that of α/β T cells could attribute to them a function of a link between innate immunity by NK cells and the specific adaptive immunity effected by α/β T cells. The γ/δ T cells appear to control the local tissue response at the site of bacterial replication and the TCRδ (T-cell receptor δ) gene deletion mice mutants were found to be more susceptible to death when challenged by *M. tuberculosis* inocula tolerated by immunocompetent mice (Kaufmann, 1995a).

The CD1b-restricted α/β T cells produce IFN-γ and express cytolytic activity, in which they resemble Th1 cells (Kaufmann, 1995a).

4. Proposed Approach to the Prevention of Infection with *M. Tuberculosis* and Proposed Approach to the Prevention of Rheumatoid Arthritis Associated with Tuberculosis Accepting that mycolic acids possess inumunoregulatory properties in spite of their simple, long chain fatty acid structure, it is proposed that the prevention of infection with *M. tuberculosis* could be achieved by a successful induction of humoral and/or cellular memory against mycolic acids leading to a long-term protection against the disease. Another approach is based on the assumption that by using appropriate tolerogenic doses of purified, biologically active mycolic acids used alone, in a supportive medium or pharmaceutical carrier or excipient or on appropriate carriers, with or without the simultaneous introduction of appropriate cytokines (Heath and Playfair, 1992), it should be possible to successfully modulate the immune response(s) in the human body. Such a treatment could potentially help to prevent or decrease mortality due to tuberculosis and be used as a potential treatment of the disease.

On the other hand, vaccination with mycolic acids used with or without the appropriate carriers, may regulate the immune system upon the infection with *M. tuberculosis*, by modulating the induced response of the recipient.

Prevention of rheumatoid arthritis associated with tuberculosis could be achieved by preventing the generation of auto-immune antibodies directed against collagen. Recently published results of the immunomodulatory properties of a synthetic 10-kD heat shock protein (hsp10) from *M. tuberculosis*, in relation to adjuvant-induced arthritis in rats, indicate that the administration of this compound could indeed lead to the delayed onset of the disease and the development of less severe symptoms (Ragno et al., 1996).

Accepting once again that mycolic acids possess immunoregulatory properties, the proposed approach is based on the assumption that by using appropriate tolerogenic doses of mycolic acids, possibly on suitable carriers, either on their own or, simultaneously with appropriate interleukin(s) (Heath and Playfair., 1992), it should be possible to successfully manipulate or regulate the immune response(s) in the human body. Such a treatment could potentially help to prevent or delay the onset of rheumatoid arthritis associated with tuberculosis, or decrease the severity of this disease.

In order to investigate this approach, adjuvant arthritis was induced in rats, which were treated with mycolic acids either prior to or after the induction of the disease. The induction of this form of arthritis, using a suspension of heat-killed and freeze-dried cells of an avirulent strain of $M.$ $tuberculosis$ H37 Ra was achieved following the method of Wauben, Wagenaar-Hilber and Van Eden (1994). Investigations into this approach are set out below in Example 2.

5. Immunogenicity of Mycolic Acids

Immunogenicity of a molecule, i.e., its ability to induce an immune reaction depends on the chemical structure and properties of the molecule and on the ability of a particular immune system to recognise it. Many compounds such as proteins, peptides, nucleic acids and polysaccharides are naturally highly immunogenic and capable of eliciting strong immune reactions when recognised as "foreign" by the immune system. On the other hand, the majority of lipid compounds, with the exception of some glycolipids, has until recently not been considered to be immunogenic.

Mycolic acids are the major lipids of the cell wall of Mycobacteria and constitute approximately 40% of the dry weight of these bacteria. Mycolic acids are high molecular weight &hydroxy fatty acids ($C_{60}$ to $C_{90}$), which have moderately long aliphatic chains in the $\alpha$-position and are characterised by a highly restricted solubility. Their aliphatic structure and absence of aromaticity suggest that, similarly to other lipid compounds, they should have very weak/limited immunogenic properties (Savelkoul, Claassen and Benner, 1997). In addition, the mechanism by which lipids could elicit immune responses in a host and the manner in which they could be presented to the immune system, have, until recently, been unknown.

However, the evidence for immunogenicity of mycolic acids, i.e., for their ability to induce an immune reaction, has been accumulated over the last three/four years on the basis of the results reported by various research centers.

It was observed by the present inventors in 1994 that mycolic acids adsorbed to proteins and administered to mice elicit an antibody response (South African Patent Application No. 95/3077 and International Patent Application No. 95/00856 relating to the induction of antibodies to mycolic acids upon immunization of mice with mycolic acids adsorbed to proteins). The response appears to be specific for mycolic acids on two accounts. It was elicited by bovine serum albumin conjugates but could be detected on ELISA wells coated with mycolic acids-gelatin conjugate in the immunoassay and the response measured on mycolic acids-gelatin conjugate as antigen could be partly inhibited by co-incubating the antisera with bovine serum albumin-mycolic acids conjugate.

The immunogenicity of mycolic acids and their immunoregulatory properties have been supported by evidence which has recently became available from other sources:

i) The discovery of Beckman et al., (1994) that mycolic acids activate DN T-cells upon presentation on antigen presenting cells While investigating presentation of non-peptide microbial antigens, Beckman et al., (1994) discovered that mycolic acids originating from $M.$ $tuberculosis$ stimulated the proliferation of a rare subset of human T cells. The group of stimulated human T cells was identified as double negative, i.e., neither $CD4^+$ (helper function) nor $CD8^+$ (cytotoxic function), T-cell clones.

Similarly, Rosat et al., (1995) reported stimulation and subsequent expansion of a human T-ell line (OGD1) upon exposure to unique cell-wall lipids isolated by organic extraction from $M.$ $tuberculosis$ and presented on CD1b molecules.

Additional observations concerning the presentation of lipoarabinomannan originating from the cell-wall fractions of $M.$ $leprae$ by CD1 molecules were reported by Sieling et al., (1995), who isolated two T-cell lines responding to the stimulation with lipoarabinomannan.

On the basis of these reports and results it appears that:
  i) mycolic acids are in fact immunogenic at least in terms of eliciting some kind of cellular and humoral immune response;
  ii) mycolic acids are presented by one of a group of five CD1 glycoproteins in humans, of which CD1b plays the major role in presentation of mycolic acids.

ii) The role of CD1 presented molecules in the presentation of mycolic acids and other mycobacterial lipids CD1 molecules constitute a group of glycoproteins occurring on antigen presenting cells. They appear to perform a novel and unique function, by presenting mycobacterial antigens originating from the lipid fraction of bacterial lysates to the immune system. CD1 molecules appear to be homologous in their function to peptide-presenting MHC (Major Histocompatibility Complex) proteins (Beckman et al., 1994; 1995) but specialized in presenting antigens of lipid or hydrophobic nature.

The compounds presented by CD1 molecules are recognised by human T cells displaying on their surface receptor chains $\alpha$ and $\beta^{*)}$ (Beckman et al., 1994, 1995) as well as $\gamma$ and $\delta$ chains$^{**)}$ (Rosat et al., 1995). The subset of $\gamma\delta$ T cells was found to express only receptors coded by $V\delta 1^+$ gene and to proliferate on exposure to unique cell-wall lipids isolated by organic extraction from $M.$ $tuberculosis,$ presented on CD1b molecules.

*) $\alpha$ and $\beta$ chains—transmembrane glycoprotein receptor chains are responsible for the recognition of antigens on antigen presenting cells (APC) after processing and presentation on MHC or other professional antigen presenting molecules such as CD1.

**) $\gamma$ and $\delta$ chains—polypeptide receptor chains are homologous to $\alpha$ and $\beta$, appearing at an early stage of thymocytes differentiation, with a very limited variability and poorly understood functions. They can recognise antigens without the requirement of prior processing and presentation by APC, even recognising antigen in solution as long as it is multivalent (Schild et al., 1994).

Both subsets of these T cells were activated on exposure to the antigens of mycobacterial origin and showed enhanced proliferation (Beckman et al., 1994, 1995; Rosat et al., 1995).

Experiments described by Tangri et al., (1995), carried out with the mouse CD1 molecules, established peptide sequences binding to this type of antigen-presenting molecules and found such peptides to be highly hydrophobic. This observation confirms the distinct role which CD1 molecules appear to be playing in the presentation of lipid or other hydrophobic compounds in a non MHC restricted manner.

iii) The anticipated role of double negative (DN) T cells in auto-immunity and immunoregulation Double negative (DN) T cells form a small, highly heterogenous group of cells residing in the thymus, comprising several early stages in T-ell development. A small percentage of these cells expresses genes coding for $\gamma\delta$ while the remaining DN express genes for $\alpha\beta$ receptor chains. They precede the appearance of the functional receptor chains and the expression of CD4 and CD8 markers (Janeway and Travers, 1994d).

DN T cells constitute less than 2% of human lymphocytes present in peripheral blood (Niehues et al., 1994). They were found to differ from single positive (SP) subsets of T cells in:
- i) proliferating in response to the presence of interleukin 3 (IL-3);
- ii) becoming activated on exposure to non-peptide antigens presented by CD1 molecules;
- iii) not responding to the stimulation with antigens presented by MHC class I and II molecules (Niehues et al., 1994).

Although the main function of this small and poorly defied T cell subset group remains unknown, there is some evidence indicating their involvement in auto-immune reactions and in the regulation of auto-immunity. The studies of von Boehmer, Kirberg and Rocha (1991) and Kisielow et al., (1988) demonstrated that in transgenic mice, the receptors for self antigens were predominantly expressed on DN cells. In humans, levels of DN T-cell populations were found to be elevated in patients with auto-immune disorders such as systemic lupus erythematosus (Shivakumar, Tsokos and Datua, 1989) and systemic sclerosis (Sakamoto et al., 1992).

The involvement of DN T cells in immunoregulation was demonstrated by Niehues et al., (1995a), who reported that the stimulated DN T cells secreted interleukin 10 (IL-10). As IL-10 can downregulate the expression of MHC proteins class II by the antigen presenting cells and, at certain concentrations, can suppress the expression of CD1 molecules (Thomssen, Kahan and Londei, 1995) and inhibit the functions of inflammatory Th1 cells (Janeway and Travers, 1994a), an important role played by DN T cells in regulating and probably suppressing immune functions and in auto-immunity is anticipated.

If it is accepted that mycolic acids are immunogenic and, when presented on CD1 molecules can activate human DN T cells, it can be postulated that two immunological phenomena observed in tuberculosis, namely the occurrence of anergy and the induction of post-tuberculosis rheumatoid arthritis could be associated with mycolic acids.

Anergy, i.e., the inability of the infected person to mount an immune response despite the presence of antigen, is commonly observed during the initial stage of infection with *M. tuberculosis* and *M. leprae*. It is believed that the specific immunocompetent lymphocytes are suppressed as a consequence of either the way in which the molecules are presented to them (Schwartz, 1993) or as the result of the absence of co-stimulatory signals (Janeway and Travers, 1994a).

If the presentation of lipid antigens on CD1 molecules creates the conditions necessary for the initiation of anergy in tuberculosis, it can be hypothesised that mycolic acids could play a direct role in this phenomenon, probably by the activated DN T cells secreting IL-10 (Niehues, et al., 1995a).

Auto-immunity or auto-reactivity is a pathological condition caused by the adaptive immune response directed at self antigens. Such responses can be generally produced by:
- i) a sudden exposure of normally hidden self antigens (as in the case of sympathetic ophthalmia);
- ii) self antigens becoming immunogenic due to chemical, physical or biological changes (as in the case of contact dermatitis);
- iii) coincidental similarity between a foreign antigen (pathogen) and the self tissue antigen, referred to as molecular mimicry (as in the case of streptococcal protein M and human heart muscle) (Merck Manual, 1987; Janeway and Travers, 1994e).

Rheumatoid arthritis, is an auto-immune disease associated with the presence of auto-antibodies and auto-reactive T cells damaging the joints' cartilage (Laycock et al, 1995). The mycobacterial antigens could be implicated in this pathological state in two ways. Either heat-shock proteins of *M. tuberculosis* (HSP 60, HSP 65) elicit the production of auto-antibodies due to the genuine molecular mimicry between them and the aggrecan i.e., the core protein of host cartilage (Roitt, 1994; Tizard, 1995b; Voet and Voet, 1995) or the production of such auto-immune antibodies is caused by a contamination of heat-shock proteins secreted by mycobacteria with mycolic acids. The latter possibility finds some support in the observation reported by Buzas et al., (1995) who could not detect any cross-reactivity between aggrecan and the mycobacterial HSP 65 produced by genetically manipulated *E. Coli*, therefore not contaminated by mycolic acids. Additional evidence that the HSP 65 may not be directly involved in the induction of adjuvant arthritis, came from Moudgil et al., (1995). These authors worked with two groups of rats, resistant and susceptible to adjuvant arthritis and found that they shared identical MHC. As only peptides can be presented by MHC, this finding implies that compounds other than proteins (e.g. lipids) are probably involved in inducing this form of arthritis.

Further evidence of the lipid nature of the molecules potentially involved in the inaction of rheumatoid arthritis comes from the studies of Beech et al., (1995) and Lemonidis et al., (1995) who studied pristane[*]-induced arthritis in mice. In both instances the response was characterized by the presence of T-lymphocytes and antibodies strongly cross-reacting with mycobacterial HSP 65.

[*] A mineral oil of defined structure, including several methyl branches.

The evidence presented above concerning the role which lipids/oils could play in inducing rheumatoid arthritis supports the hypothesis that in the case of tuberculosis this role could be performed by mycolic acids forming natural conjugates with proteins present in the infected host.

- iv) Our observations concerning cross-reactivity of mice antisera against mycolic acids-BSA with gelatin During our experimental work substantiating Patent No 94/2575, it was observed that the antibodies produced during immunization with mycolic acids-protein conjugates cross-reacted with gelatin, the denatured form of collagen. Without wishing to be bound by theory, we propose a hypothesis to explain this observation, namely that the murine immune system probably does not recognize mycolic acids as such, but rather as modified epitopes on protein molecules.

Similarly, during infection with *M. tuberculosis*, mycolic acids originating from the pathogen may become attached to some proteins present in the host's body, such as heat-shock proteins known to be expressed on the surface of infected macrophages (Grange, Stanford and Rook, 1995) or host protein to create "foreign" epitopes. The presence of such epitopes can lead to the production of auto-antibodies and auto-reactive T cells against collagen (gelatin), which could attack host collagen leading to the development of an auto-immune reaction. The auto-antibodies and auto-reactive T cells thus generated, may significantly influence the degree of severity of the disease and may play a crucial role in TB patient survival.

If it is remembered that:
- i) collagen is the native form of gelatin;
- ii) the mice antibodies generated against mycolic acids-protein conjugates were observed to recognise gelatin;
- iii) arthritis can be produced in experimental animals by injection of collagen, collagen reactive T cells or anti-collagen antibodies (Brand et al., 1995); and iv) collagen is the most abundant protein in higher vertebrates (Sakai, 1995) and that lungs, where the original contact with *M. tuberculosis* usually takes place, comprise large numbers of collagen fibrils (Leeson and Leeson, 1981) the potential of mycolic acids' attachment to the host's major class of fibrous protein and their involvement in the generation of auto-immune antibodies directed against collagen and probably leading to the development of rheumatoid arthritis associated with tuberculosis, becomes evident.

Furthermore, the presence of antibodies recognising collagen/gelatin in a tuberculosis patient could be responsible for impaired resistance against bacterial infection (Bras and Aguas, 1995). Such antibodies could react with the collagen-like region of human serum (segment C1q) thus impairing this serum protein's crucial role in the cytotoxic reaction towards bacteria and infected host cells. The presence of anti-C1q antibodies in patients with systemic lupus erythematosus was associated with persistent hypocomplementaemia and defective ability to opsonise bacteria, which led to the patients' inability to dispose of life-threatening infections (Davies, Norsworthy and Walport, 1995).

IMMUNOREGULATORY AND IMMUNOGENIC PROPERTIES OF COUNTERCURRENT-PURIFIED MYCOLIC ACIDS

The substantiation/evidence for the immunogenic and immunoregulatory properties of countercurrent-purified mycolic acids is illustrated by the three examples described below.

EXAMPLE 1

Protection against tuberculosis in mice provided by the administration of purified mycolic acids. Experiments involving animals injected with *M. tuberculosis* by intravenous administration.

1.1 Materials
1.1.1 Cultures

*Mycobacterium tuberculosis* H37Rv ATCC 27294—a virulent strain, originally isolated from an infected human lung. Type strain of the species.

*Mycobacterium vaccae* ATCC 15483—a strain originally isolated from cow's milk. Type strain of the species.
The cultures were purchased in lyophilized form from the American Type Culture Collection (ATCC), Maryland, USA.

1.1.2 Media
1.1.2.1 Growth media

The following media were used for the cultivation of *M. tuberculosis*:

Löwenstein-Jensen (LJ) medium (slants) and Middlebrook 7H-10 agar medium (plates).

A detailed composition of the ingredients necessary for the preparation of these media as well as the conditions recommended for their sterilization, are given in the Laboratory Manual of Tuberculosis Methods, Tuberculosis Research Institute of the SA Medical Research Council (1980, Chapter 6, pp 83–105; Second Edition, revised by E E Nel, H H Kleeberg and E M S Gatner).

The media were prepared by the National Tuberculosis Institute of the Medical Research Council of South Africa, in Pretoria.

1.1.2.2 Media Used for Washing and Diluting of Mycobacteria

The harvested bacteria were washed in sterile 0.9% m/v NaCl (Saarchem, Chemically Pure, RSA).

Medium used for the preparation of serial dilutions, preceding the determination of viable counts of *M. tuberculosis*, was prepared by dissolving Tween 80 (Merck, Chemically Pure) in 0.9% m/v NaCl (Saarchem, Chemically Pure) to a concentration of 0.01% v/v and distributing it in 9.0 ml aliquots into test-tubes. The autoclaved media were stored at 4° C.

1.1.2.3 Media Used for the Amplification of the Competitive Plasmid pGEM-3Z

Dulbecco's Modified Eagle's Medium (DMEM)—manufactured by Life Technologies Inc., Country LB agar comprising:
10% m/v Tryptone (Biolab Diagnostics, RSA)
5% m/v Yeast extract (Difco Laboratories, Michigan, USA)
10% m/v NaCl (Saarchem, Chemically Pure, RSA) and
1.5% m/v agar (Saarchem, Chemically Pure, RSA).

LB broth comprising:
10% m/v Tryptone (Biolab Diagnostics, RSA)
5% m/v Yeast extract Difco Laboratories, Michigan, USA) and
10% m/v NaCl (Saarchem, Chemically Pure, RSA).

Ampicillin and streptomycin (Life Technologies Inc., Scotland)

Sodium pyruvate (Life Technologies Inc)

Agarose (Promega Corporation, Madison, USA)

1.1.3 Reagents
1.1.3.1

For the preparation of the reagents used for the extraction, derivatization and High-Performance Liquid Chromatography (HPLC) analysis of mycolic acids, HPLC Grade methanol (BDH) and double-distilled deionized water were used.

Reagent A: 25% potassium hydroxide (Saarchem, Analytical Grade) dissolved in methanol-water (1:1), i.e., 62.5 g potassium hydroxide was dissolved in 125 ml water and 125 ml methanol (BDH, HPLC Grade) was added.

Reagent B: Concentrated hydrochloric acid (Saarchem, Analytical Grade) diluted 1:1 with water.

Reagent C: 2% potassium bicarbonate (BDH. Analytical Grade) dissolved in methanol-water (1:1), 10 g potassium bicarbonate was dissolved in 250 ml water and 250 ml methanol was added.

Reagent D: para-bromophenacylbromide dissolved in acetonitrile and crown ether (Pierce Chemical Co, Cat. No 48891) was dispensed in 500 µl quantities into small amber-coloured screw cap vials with Teflon-coated septa. The caps were tightened and the vials were wrapped with Parafilm. Reagent D was stored at 4° C.

Reagent E: Reagent E was prepared by mixing reagent B 1:1 with methanol.

HPLC Standard: High Molecular Weight Internal Standard (C-100) from Ribi ImmunoChem Research Company, Cat No R-50. The standard, 1 mg, was dissolved in 20 ml chloroform (BDH, HPLC Grade) at 4° C. and aliquots of 100 µl were dispensed into 4 ml amber WISP vials, dried, capped with Teflon-coated septa and stored at 4° C.

Chloroform (Saarchem, Analytical Grade, RSA)

Methylene chloride (BDH, UK, HPLC-Grade)

Reagents A, B, C and E were prepared fresh prior to experiments, taking all the necessary safety precautions.

1.1.3.2 The following reagents were used for the preliminary purification of crude bacterial extracts ("funnel extraction") and for the countercurrent purification of the extracted mycolic acids:

Chloroform (Saarchem, Chemically Pure)

Methanol (Saarchem, Chemically Pure)

Acetone (Saarchem, Chemically Pure)

Sodium chloride (Saarchem, Analytical Grade)

Double-distilled deionized water was used for the preparation of the required reagent concentrations. i.e.,:
39% v/v methanol
42% v/v chloroform
0.2 M NaCl 1.1.3.3 Reagents used in the Semi-Quantitative Competitive Reverse Transcriptase Polymerase Chain Reaction (QC-RT-PCR):

The following reagents were used:

Ethidium bromide (Boehringer Mannheim, Germany)

Formamide and formaldehyde (BDH, UK)

Tris(Hydroxymethyl)-aminomethane (Merck, Germany)

EDTA (Ethylenediaminetetra-acetic acid) (Merck)

Sodium acetate (Merck)

TRI-reagent (Molecular Research Centre Inc, USA)

Formazol (Molecular Research Centre Inc)

MOPS (3-(N-morpholino) propanesulfonic acid) (Sigma Chemicals, USA)

Diethyl pyrocarbonate (DEPC) (Sigma)

Oligo dT primers (Life Technologies Inc., Scotland)

Superscript RNase H Reverse Transcriptase (Life Technologies Inc.)

Recombinant Taq Polymerase Dynazyme (Finnzymes OY)

Amplitaq Gold (Roche Molecular Systems, USA)

Qiagen mini preparatory column Kit (Qiagen)

Tris EDTA buffer: Tris base 10 mM disodium ethylene diamine tetraacetate.$2H_2O$, pH adjusted to pH 8.3.

1.1.3.4 Reagents used in the purification of $\alpha\beta TCR^+CD4^+$, $\alpha\beta TCR^+CD8^+$ single positive (SP) and $\alpha\beta TCR$, $CD4^-$ and $CD8^-$ double negative (DN) T cells from the human peripheral blood The reagents used in this part of the experimental work were described by Niehues et al., (1994, 1995b).

1.1.4 Experimental Animals

Eight to twelve weeks old female Balb/c (a tuberculosis-susceptible strain) and C57/b1J6 mice (a tuberculosis-resistant strain) were used in the "immunoregulatory" experiments. The mice were inbred for 11 and 9 generations, respectively, by the Animal Centre at the South African Institute for Medical Research in Johannesburg. Male mice of corresponding age were used for the collection of serum necessary for the preparation of mycolic acids/mouse serum conjugates.

Seventeen weeks old Sprague-Dawley female rats were used for the induction of anti-mycolic acids antibodies.

Feed and Water

Mice cubes, manufactured by EPOL and tap, autoclaved water were provided ad libitum.

Sanitation

Bronocide, manufactured by Essential Medicines (Pty) Ltd, was used for sanitation purposes.

1.1.5 Plasticware

The following plasticware was used:

Disposable Petri's dishes (Promex, RSA)

ELISA plates (Sterilin UK)

Sterile, disposable 50 ml centrifuge tubes (Corning, USA)

Disposable tips (Elkay, Denmark)

96-well round bottom microplates (Nunc, Denmark)

1.2 Methods

The following methods were used in the experimental work:

1.2.1 Cultivation of the Bacterial Stains

The bacteria were cultivated at 37° C. using Löwenstein-Jensen (LJ) medium slants and Middlebrook 7H-10 agar medium plates.

The sterility of all the media was confirmed, before they were used in the experiments by incubating them at 37° C. for 24 h.

For routine extractions of mycolic acids approximately 4-week old *M. tuberculosis* and 2-week old cultures of *M. vaccae*, grown on LJ slants, were used. When Middlebrook 7H-10 agar medium plates were used, 2-week old cultures of *M. tuberculosis* were harvested for the extraction of mycolic acids. For the preparation of bacterial suspensions used for the experimental induction of tuberculosis, approximately 2-week old cultures of *M. tuberculosis*, grown on LJ slants were used.

1.2.2 Viable and Total Bacterial Counts

For the viable count determination, serial suspensions of the harvested bacteria were prepared in the diluent medium (as specified under 1.1.2.2) to a density corresponding to a McFarland standard 4 (approximately OD of 1.0; using a Beckman DU 65 spectrophotometer, at 486 nm). Ten fold serial dilutions were prepared using 9 ml aliquots of the diluent medium. From the last three dilutions corresponding to $10^{-3}$, $10^{-4}$ and $10^{-5}$ of the original suspension, aliquots of 0.1 ml (100 µl) were withdrawn and spread over the surface of Middlebrook 7H-10 plates. The plates were incubated at 37° C. and the developed colonies counted after two to three weeks for *M. tuberculosis* and after one week for the plates seeded with *M. vaccae*.

The direct total count was performed using a Neubauer counting chamber and the autoclaved cultures of *M. tuberculosis* and *M. vaccae*, originally adjusted to a density corresponding to a McFarland standard 4 and suitably diluted with the diluent medium.

Statistical analysis of the bacterial counts included the mean values of bacterial counts and standard deviations.

1.2.3 Preparation of Mycolic Acids from Bacterial Samples

The preparation of bacterial samples comprised three steps:

harvesting of the Mycobacteria cells;

saponification and extraction of mycolic acids.

Glassware used for the harvesting, extraction, derivatization and HPLC analyses of mycolic acids was washed in 2% (v/v) Contrad (Merck), rinsed in water, followed by rinsing in chloroform, water, Technical Grade methanol, water and finally rinsed in double distilled deionized water. The washed glassware was dried in a warm air oven.

Harvesting was done by scraping the bacterial growth from the surface of media slants or agar plates (using sterile plastic loops) and by suspending them in Reagent A. Initial bacterial suspensions were prepared in Reagent A, by vortexing the harvested cells with sterile glass beads. Homogenous bacterial suspensions were prepared using sterile tissue homogenizers. Prior to the saponification, the density of the bacterial suspensions was adjusted to a density corresponding to a McFarland standard 4.

The saponification, extraction and derivatization of mycolic acids were carried out as described by Butler, Jost and Kilburn (1991), with minor modifications and are described under the relevant headings.

Saponification of the Mycobacteria in Reagent A was carried out in an autoclave at 121° C., for 30 min.

1.2.4 Extraction of Mycolic Acids

The saponified samples were allowed to cool after autoclaving. Into 2 ml samples containing crude extract, 1.5 ml Reagent B was introduced. After vortexing, the pH of each sample was checked and if necessary, adjusted to pH 1 with Reagent B.

Subsequently, 2.0 ml chloroform was added to each sample and vortexed for 30 seconds. The layers were allowed to separate. The bottom layers were removed with Pasteur pipettes, transferred to amber WISP vials and evaporated to dryness at 85° C. in a heat block-evaporator under a stream of nitrogen. To neutralize traces of acid carried over, 100 µl of reagent C was added to each sample and the fluid evaporated to dryness at 85° C. in a heat block-evaporator under a stream of nitrogen.

1.2.5 Storage of the Crude Extracted Mycolic Acids

The material obtained from the large-scale extraction of mycolic acids originating from *M. tuberculosis* and *M. vaccae*, i.e., the crude bacterial extracts, was stored under acetone, at 4° C. in 4 ml amber WISP vials. To prevent evaporation/drying and the exposure to light, the caps of the WISP vials were covered with Parafilm.

1.2.6 Determination of Mycolic Acids Contents in Crude Extracts

Extracted mycolic acids were derivatized as follows:

To a cooled sample of crude extract (approximately 10 µg in 2.0 ml Reagent A), an aliquot of 1.0 ml chloroform was introduced, followed by the addition of 100 µl of Reagent D (derivatization reagent). The capped samples were vortexed for 30 seconds and heated for 20 minutes at 85° C. in a heat block-evaporator. Subsequently, the samples were cooled and 1.0 ml of Reagent E added. The samples were vortexed for 30 seconds and the layers allowed to separate. The bottom layers were removed with Pasteur pipettes and transferred to WISP-vials. The vials were placed in a heat block-evaporator and their contents evaporated to dryness at 85° C. using a stream of nitrogen.

The residues were resuspended in 0.212 g (which corresponds to 160 µl) methylene chloride, capped and vortexed. Each reconstituted sample was introduced into a WISP vial containing 5 µg of the HPLC internal standard (prepared as described under 1.1.3.1), filtered through a 0.22 µm Millex GV4 filter with a polyethylene housing into another amber-coloured WISP-vial. The recapped vials were stored at 4° C. until ready for HPLC analysis.

1.2.7 HPLC Analysis and Quantification of Mycolic Acids

Repeatability and accuracy of the pipette used for the distribution of the HPLC standard was determined The precision was established to be +/−1% and was confirmed prior to each aliquoting of the internal standard.

For the HPLC analysis 10 µl from each sample (maintained on ice during handling), was analyzed. Control samples, i.e., 10 µl of filtered methylene chloride, were run prior to each set of samples analyzed. If a large number of samples was analyzed, in order to validate the reliability of the HPLC apparatus, control samples were run after every three or four test samples.

The reverse-phase HPLC analyses were carried out using a Waters 600 E System Controller High Performance Liquid Chromatography apparatus consisting of:
 Microsep M741 Data Module;
 Waters 712 WISP Autosampler;
 Detector (Waters 486 Tunable Absorbance Detector);
 Column: Nova-Pak C18 4 µm 3.9×150 mm and an end connector set for steel cartridge columns
 RKC Rex-C 4 Column Temperature regulator.
 Running conditions were:
  Mobile phase:
  Solvent A: HPLC Grade methanol
  Solvent B: HPLC Grade methylene chloride
  Flow Rate: 2.5 ml/min
  Column temperature: 30° C.
  The detector was set at 260 nm.

Prior to use, the solvents were sparged with Instrument Grade helium. High Purity Nitrogen was used to control hydraulics of the WISP vials autosampler.

The HPLC gradient initially comprised 98% (v/v) methanol (Solvent A) and 2% (v/v) methylene chloride (Solvent B). The gradient was increased linearly to 80% A and 20% B at one minute; 35% A and 65% B at ten minutes, held for 30 seconds and then decreased over 10 seconds back to 98% A and 2% B. This ratio was maintained for 4 minutes to allow for stabilization of the system prior to injection of the next sample.

Mathematical quantification of mycolic acids was carried out by comparing the combined peak areas of the tested samples to the peak area of the introduced quantity of the High Molecular Weight Internal HPLC Standard 1.2.8 Preliminary Purification of Crude Mycobacterial Extracts In order to shorten the time required for the countercurrent purification of the crude mycobacterial extracts, an additional preliminary extraction step was introduced. This step had a dual purpose:
 i) to remove unnecessary cellular components from the crude extract prior to the countercurrent purification and
 ii) to reduce soap fraction in the crude bacterial extracts.

A portion of the crude extracted material (approximately 3–4 g) was suspended in a minimum volume of the lower phase solvent (usually 100 ml), transferred into a separation funnel and mixed with an equal volume of the upper phase solvent. The phases were allowed to separate and the upper phase was removed and stored at 4° C. Into the remaining lower phase an equal volume of the upper phase solvent was again introduced and the process of the phase separation was repeated.

The second upper phase was removed and stored at 4° C. and the second lower phase was dried in a Buchi Rotoevaporator RE 120, at 75° C. and its mass recorded.

1.2.9 Countercurrent Purification of Mycolic Acids Originating from *M. tuberculosis* and *M. vaccae*

Countercurrent apparatus

A countercurrent apparatus produced by H O POST, Instrument Company Inc., Middle Village, N.Y. was used during the investigations. The "trains" in this model consisted of 2×250 inter-connected tubes.

Solvent system used in the countercurrent apparatus

The solvent system used for the countercurrent separation consisted of:
 42% v/v chloroform (Saarchem, Chemically Pure Reagent)
 39% v/v methanol (Saarchem, Chemically Pure)
 19% v/v 0.2 M NaCl (Saarchem, Chemically Pure).
 Double-distilled deionized water was used for the preparation of the solvent system.

The components were mixed, equilibrated and the upper and lower phases were collected using a separation funnel.

The composition of the upper phase was established to be: 15% v/v chloroform, 52% v/v methanol and 33% v/v 0.2 M NaCl.

The composition of the lower phase was established to be: 68% v/v chloroform, 27% v/v methanol and 5% v/v 0.2 M NaCl.

The countercurrent purification process was carried out under the following conditions:

A countercurrent distribution tram comprising 55 tubes, numbered 0–54, was used in the experiments. The upper phase solvent, a volume of 600 ml, was introduced into a buffer reservoir. A sample of 125 mg of mycolic acids after the preliminary purification was dissolved in 50 ml of the lower phase solvent, divided into five aliquots and introduced into first five tubes, numbered 0–4. Subsequently, 10 ml of the upper phase solvent was introduced into each of the first five countercurrent tubes. Into the remaining 50 tubes aliquots of 10 ml of the lower phase were introduced Upper phase, in volumes of 10 ml per cycle, was automatically dispensed into tube number 0, repeatedly over 55 cycles resulting in approximately 5 hour operation Thus, fifty five countercurrent cycles were performed, with each cycle consisting of 10 mixing pendula and 3 minutes phase separation time.

| | |
|---|---|
| Initial load of crude extract after the funnel extraction: | 125 mg |
| Number of cycles: | 55 |
| Equilibration time: | 3 min |

1.2.11 Removal of Malachite Green from the Countercurrent-purified Mycolic Acids To remove traces of malachite green derived from bacterial growth media (when *M. tuberculosis* was grown on LJ slants), the countercurrent-purified material was selectively precipitated in the following manner. Countercurrent-purified mycolic acids (92 mg) were placed in a WISP vial into which 1.0 ml chloroform was introduced. The dissolved mycolic acids were transferred into a pre-weighed round-bottom flask. The vial was rinsed twice with 1.0 ml chloroform and the two aliquots of chloroform were added to that already present in the round-bottom flask. Subsequently, acetone was introduced drop-wise in 500 $\mu$l aliquots. In total, 26 ml of acetone was introduced and the white flakes of the precipitated-out mycolic acids were washed twice with 20 ml acetone. The acetone supernatant, with the dissolved malachite green, was removed and the mycolic acids dried by evaporation.

The procedure was carried out at room temperature.

1.2.12 Determination of Mycolic Acids after Countercurrent Purification

In order to increase the accuracy of the HPLC determination of mycolic acids, the High Molecular Weight Internal Standard (C-100) was introduced into the countercurrent-purified mycolic acids before the saponification.

A sample of 0.5 mg of the countercurrent-purified mycolic acids was introduced into a WISP vial containing 5 $\mu$g of the High Molecular Weight Internal Standard (C-100). Saponification of mycolic acids was carried out with 2 ml of Reagent A at room temperature. The WISP vial was vortexed for 30 seconds. The extraction was carried out with 1.5 ml of Reagent B. After vortexing, the pH of the sample was checked and if necessary, adjusted to pH 1 with Reagent B.

Subsequently, 2.0 ml chloroform was added to each sample and vortexed for 30 seconds. The layers were allowed to separate. The bottom layers were removed with Pasteur pipettes, transferred to amber WISP vials and evaporated to dryness at 85° C. in a heat block-evaporator under a stream of nitrogen. To neutralize traces of acid carried over, 100 $\mu$l of reagent C was added to each sample and the fluid evaporated to dryness at 85° C. in the heat block-evaporator under a stream of nitrogen.

Therefore, the main difference between the determination of mycolic acids after countercurrent purification and in the crude extract was the time of introduction of the Internal Standard.

1.2.13 Determination of Yield of the Countercurrent Separation

In order to calculate the approximate yield of purification/separation, the amount of the mycolic acids present in the samples obtained after the countercurrent separation/purification was compared to the amount of these compounds present in the crude cellular extract introduced into the countercurrent apparatus. The calculations were based on the results obtained by the HPLC analysis.

It should be stressed, that it is essential for the calculation of the yield of the countercurrent separation, that the mycolic acids determined by HPLC should be within the tested linear range of the HPLC UV detector.

1.2.14 Infra-red Spectroscopy

Samples of mycolic acids to be analyzed by infra-red spectroscopy were prepared in the following manner. Countercurrent-purified mycolic acids, 1 mg, were dissolved in 1 ml chloroform, introduced into 200 mg KBr and thoroughly mixed. After the evaporation of chloroform, a pellet of mycolic acids in KBr was prepared by using a Shimadzu tablet die and applying a force of approximately 100 kilonewtons on the sample for 10 minutes. A control pellet was prepared using only chloroform, without mycolic acids added to the preparation. The control pellet was used to determine the background infra-red spectrum. The spectra were analyzed on a Perkin Elmer. 1600 series FT-IR system and plotted on a Roland Digital Group X-Y Plotter DXY-1200.

1.2.15 Determination of the Stability of the Countercurrent-purified Mycolic Acids A pooled sample of the countercurrent-purified mycolic acids was prepared by introducing five batches of countercurrent-purified mycolic acids into a container, dissolving them in chloroform and mixing the contents very well. The chloroform was evaporated using a Buchi Rotoevaporator RE 120, at 75° C. and the sample dried under a stream of nitrogen. The pooled sample was divided into two parts which constituted two stock samples. The first stock sample was re-saponified and the second was left as a non-saponified stock sample. From both stock samples individual aliquots were withdrawn and placed at −20° C., 4° C. and 25° C. Three samples were prepared per each time point and HPLC analyses were carried out after 6 weeks, 3, 6, 9 and 12 months of storage.

1.2.16 Methods Used in Handling Experimental Animals in the Immunoregulatory Experiments 1.2.16.1 Environmental Conditions Under Which the Experimental Animal Were Maintained Experimental animals Eight to twelve weeks old female Balb/c (a tuberculosis-susceptible strain) and C57/b1J6 mice (a tuberculosis-resistant strain) were used in the "immunoregulatory" experiments.

Experimental animals were accommodated in cages with a floor area of 450 $cm^2$, with 8 mice per cage.

Environmental conditions: Temperature and humidity in the animal facility were set at 20° C. (+/−1° C.) and 40%

(+/−10%), respectively. Lighting was provided by means of fluorescent tubes. A light-darkness cycle of alternating 12 hour periods was set up.

Cages

Mice were housed in transparent polypropylene cages with tight fitting stainless steel lids. Wooden shavings, after autoclaving, were provided as nestling material.

Sanitation

Animal rooms, mice cages and glass bottles were cleaned and decontaminated once a week using Bronocide. Water bottles after washing were autoclaved once a week.

Glove isolator

Mice infected with *M. tuberculosis* H37Rv were maintained in a glove isolator manufactured by Labotec, South Africa The isolator was inflated by a positive pressure of 4 atm. It was equipped with an air inlet pre-filter (with the pore size of 0.6 $\mu$m) through which the incoming air was filtered and an outlet HEPA (High Efficiency Particulate Air) filter (with a pore size of 0.22 $\mu$m) through which the outgoing air was filtered before leaving the isolator. The air-flow rate was regulated at 7 exchanges per hour.

Sanitation

Animal rooms, mouse cages, the glove isolator and water bottles were cleaned and decontaminated once a week using Bronocide. Water bottles, after washing, were autoclaved once a week.

1.2.16.2 Identification of the Experimental Animals

Individual identification of mice was accomplished by making ear marks.

1.2.16.3 Collection of Blood Samples and Preparation of Mouse Serum

Mice were bled from the tail vein and the blood collected into sterile Eppendorf's tubes. The collected blood was incubated at 37° C. for one hour and then left at 4° C. overnight for the clot to retract. The serum was recovered by centrifugation (in a Beckman J-6 centrifuge, at 1000 g for 15 min), aliquoted in volumes of 1.0 ml and stored frozen at −70° C.

1.2.16.4 Preparation of Mycolic Acids-mouse Serum Conjugates

The required mass of mycolic acids (2.5 mg) was dissolved in 200 $\mu$l chloroform and added to 10.0 ml of mouse serum (see 1.2.19.3), previously filtered through a 0.22 $\mu$m filter. Thus, the volume of dissolved mycolic acids constituted 2% of the volume of mouse serum.

The sample was sonicated using a Branson Sonifier B 30 Cell Disruptor, (at 20% duty cycle, output control of 2, for 50 pulses, at room temperature). The sample was maintained for 1 hour at room temperature, to allow air bubbles formed during sonication to escape. In order to remove chloroform, nitrogen was bubbled through the conjugate until the chloroform odour was removed. The conjugate was prepared immediately before administration to the experimental animals.

1.2.16.5 Preparation of Bacterial Suspensions for the Induction of Tuberculosis in Mice The cells of *M. tuberculosis* H37 Rv, harvested from LJ slants were suspended in the diluting buffer (0.01% v/v Tween 80 in 0.9% m/v NaCl) and homogenized After centrifugation in a Beckman J-6 centrifuge for 20 min at 1 580 g, the cells were washed with a sterile solution of 0.9% m/v of NaCl and adjusted to a concentration corresponding to a McFarland standard No. 4. After the confirmation of the total direct bacterial count, carried out on an autoclaved suspension in a Neubauer counting chamber, the suspension was further diluted in the sterile solution of 0.9% NaCl to obtain concentrations of *M. tuberculosis* corresponding to $10^3$, $10^4$ and $10^5$ cells/ml.

The viable counts of the mycobacteria in the suspensions were confirmed by plating 100 $\mu$l aliquots of the relevant dilutions onto Middlebrook 7H-10 agar medium, incubating the plates at 37° C. for two weeks and counting the number of colony forming units (CFU).

The suspensions were introduced into the experimental animals in aliquots of 100 $\mu$l per animal.

1.2.16.6 Introduction of the *M. tuberculosis* H37 Rv Suspensions, Mycolic Acids-mouse Serum Conjugate and Mouse Serum The introduction of the bacterial suspensions and of the mycolic acids conjugates was carried out via the intravenous route. Prior to injections, mice were heated for 5 min in a heating box until vasodilation of the tail veins could be observed.

The respective bacterial suspensions were introduced in aliquots of 100 $\mu$l per mouse. The mycolic acids-mouse serum conjugate was administered by introducing 25 $\mu$g mycolic acids/100 $\mu$l mouse serum per mouse.

Control animals received 100 $\mu$l of mouse serum introduced in the same manner.

12.16.7 Experimental Set-up

The experimental set-up is presented in Tables 2a–2d.

TABLE 2a

Experimental set-up for the immunoregulatory experiment IR-III

| Description of experiment | Group | Number of mice | Set-up | Number of injections | Time schedule Pretreatment | Infection | Treatment |
|---|---|---|---|---|---|---|---|
| Controls |  |  |  |  |  |  |  |
| Controls were performed to test: | group 1 | 9 | — | — | — | — |  |
| - M tb infection | group 2 | 9 | M tb |  |  | M tb |  |
| - effect of the serum carrier | group 3 | 3 | serum | one | serum |  |  |
| - effect of the way of administration of MA | group 4 | 3 | MA | one | MA 5 $\mu$g |  |  |
| as single or multiple injection | group 5 | 3 | serum | three |  |  | serum |
|  | group 6 | 3 | MA | three |  |  | MA 5 $\mu$g |
| Pre-treatment |  |  |  |  |  |  |  |
| Pretreatment of mice with serum alone or | group 7 | 10 | M tb + serum | one | serum | M tb |  |
| MA adsorbed on mouse serum one week | group 8 | 10 | M tb + MA | one | MA 5 $\mu$g | M tb |  |
| prior to infection | group 9 | 10 | M tb + MA | one | MA 25 $\mu$g | M tb |  |

TABLE 2a-continued

Experimental set-up for the immunoregulatory experiment IR-III

| Description of experiment | Group | Number of mice | Set-up | Number of injections | Time schedule Pretreatment | Infection | Treatment |
|---|---|---|---|---|---|---|---|
| Treatment | | | | | | | |
| Treatment of mice with serum alone or MA adsorbed on mouse serum two weeks after infection in a single or multiple injection | group 10 | 10 | M tb + serum | one | | M tb | serum |
| | group 11 | 10 | M tb + MA | one | | M tb | MA 5 μg |
| | group 12 | 10 | M tb + MA | one | | M tb | MA 25 μg |
| | group 13 | 10 | M tb + seruin | three | | M tb | serum |
| | group 14 | 10 | M tb + MA | three | | M tb | MA 5 μg |
| | group 15 | 10 | M tb + MA | three | | M tb | MA 25 μg |

Abbreviations:
M tb - *Mycobacterium tuberculosis*
MA - Mycolic acids

TABLE 2b

Experimental set-up for the Immunoregulatory experiment IR-IV (Balb/c mice)

| Description of experiment | Group | Number of mice | Set-up | Time schedule Pre-treatment | Infection | Treatment |
|---|---|---|---|---|---|---|
| Controls | | | | | | |
| Controls were performed to test: | group 1 | 16 | — | — | — | |
| - M tb infection | group 2 | 16 | M tb | | M tb | |
| Pre-treatment (single) | | | | | | |
| - effect of the serum carrier | group 3 | 16 | MA + M tb | 12.5 μg MA | M tb | |
| - effect of the way of administration of | group 4 | 16 | MA + M tb | 25.0 μg MA | M tb | |
| MA as single or multiple injection | group 5 | 16 | MA + M tb | 50.0 μg MA | M tb | |
| | group 6 | 16 | serum + M tb | serum | M tb | |
| Treatment (multiple) | | | | | | |
| Treatment of mice with serum alone or | group 7 | 16 | M tb + MA | | M tb | 3 × 8.0 μg MA |
| MA adsorbed on mouse serum | group 8 | 16 | M tb + MA | | M tb | 3 × 16.0 μg MA |
| two weeks after infection in | group 9 | 16 | M tb + serum | | M tb | 3 × serum |
| multiple injections | | | | | | |

Abbreviations:
M tb - *Mycobacterium tuberculosis*
MA - Mycolic acids

TABLE 2c

Experimental set-up for the immunoregulatory experiment IR-IV (C57/b16 mice)

| Description of experiment | Group | Number of mice | Set-up | Time schedule Pre-treatment | Infection | Treatment |
|---|---|---|---|---|---|---|
| Controls | | | | | | |
| Controls were performed to test: | group 1 | 14 | — | — | | |
| - M tb infection | group 2 | 14 | M tb | | M tb | |
| Pre-treatment (single) | | | | | | |
| - effect of the serum carrier | group 3 | 14 | MA + M tb | 12.5 μg MA | M tb | |
| - effect of the way of administration of | group 4 | 14 | MA + M tb | 25.0 μg MA | M tb | |

TABLE 2c-continued

Experimental set-up for the immunoregulatory experiment IR-IV (C57/b16 mice)

| Description of experiment | Group | Number of mice | Set-up | Pre-treatment | Infection | Treatment |
|---|---|---|---|---|---|---|
| MA as single or multiple injection | group 5 | 13 | MA + M tb | 50.0 µg MA | M tb | |
| | group 6 | 13 | serum + M tb | serum | M tb | |
| Treatment (multiple) | | | | | | |
| Treatment of mice with serum alone or | group 7 | 14 | M tb + MA | | M tb | 3 × 8.0 µg MA |
| MA adsorbed on mouse serum two | group 8 | 13 | M tb + MA | | M tb | 3 × 16.0 µg MA |
| weeks after infection in multiple injections | group 9 | 13 | M tb + serum | | M tb | 3 × serum |

Abbreviations:
M tb - *Mycobacterium tuberculosis*
MA - Mycolic acids

TABLE 2d

Experimental set-up for the immunoregulatory experiment No V

| Description of experiments | Group | Number of mice | Set-up | Pre-treatment | Infection | Treatment |
|---|---|---|---|---|---|---|
| Controls | | | | | | |
| Controls were performed to test the effect of: | | | | | | |
| - Untreated uninfected | group 1 | 25 | — | — | — | |
| - M tb infection | group 2 | 25 | M tb | | M tb | |
| - effect of the serum pretreatment | group 3 | 25 | serum pre-treat. | serum | M tb | |
| - effect of the serum treatment 21, 24 and 27 days after infection | group 4 | 25 | serum treatment | | M tb | serum |
| Pretreatment | | | | | | |
| Pretreatment of mice with MA from M tb adsorbed on mouse serum one week prior to infection | group 5 | 25 | MA (M tb) + M tb | MA 25 µg | M tb | |
| Pretreatment of mice with MA from M vac adsorbed on mouse serum one week prior to infection | group 6 | 25 | MA (M vac) + M tb | MA 25 µg | M tb | |
| Treatment | | | | | | |
| Treatment of mice with MA from M tb adsorbed on mouse serum 21, 24 and 27 days after infection | group 7 | 25 | MA (M tb) + M tb × 3 | | M tb | 3 × 8 µg MA (M tb) |
| Treatment of mice with MA from M vac adsorbed on mouse serum 21, 24 and 27 days after infection | group 8 | 25 | MA (M vac) + M tb × 3 | | M tb | 3 × 8 µg MA (M vac) |

Abbreviations:
M tb - *Mycobacterium tuberculosis*;
M vac - *Mycobacterium vaccae*;
MA - Mycolic acids 1.2.16.8 Assessment of Pathology of the Experimental Animals Individual mass measurements of all the experimental animals were carried out at seven-day intervals, at the same time of a particular day. These measurements were carried out using a Sartorius electronic scale (with a range of 0.00–200.00 g and accuracy of 0.01 g) and a plastic beaker to contain the mice.

Post mortem analyses were performed on control and infected mice. Dissection of the diseased mice and histological examination of the appropriate organs were carried out by Dr J H Vorster of the Section of Pathology of the Veterinary Research Institute, Onderstepoort, 0110.

Methods used in histopathological assessments

After dissecting of various organs, i.e., the lungs, spleens and livers, from mice cadavers, they were individually weighed and photographed.

Macroscopic assessment

Macroscopic assessment of the degree of infection in various organs was carried out by comparing individual organs originating from various groups of experimental mice to the control organs. The evaluators were not aware of the treatment to which individual animals were subjected.

Microscopic assessment

Fixation of the organs was carried out by submerging them in 10% v/v formaldehyde solution in PBS buffer. The organs/tissues were subsequently embedded in paraffin-wax and sections of 5 μm thickness prepared by cutting with microtome.

For granuloma counts, organ sections were stained in haematoxylin/eosin solution according to Luna (1968). Lesions observed in the tissues were graded by counting the number of granulomas per field, using 10 fold magnification for the liver and lung tissues and 40 fold magnification for the spleen tissue.

A qualitative grading system for the assessment of the severity of lung lesions was devised as follows:

1—small, well defined granulomas in the lungs;
2—larger, more diffused granulomas which sometimes formed extended focal areas of granulomatous pneumonia, occupying less than a third of the lung tissue. Interstitial pneumonia was slightly more pronounced;
3—mostly fused granulomas which were extensive and affected more than one third of the lung tissue.

For counts of add-fast microorganisms, the sections were stained by Ziehl-Neelsen technique (Heifets and Good, 1994). (Using this technique, acid-fast bacteria stain red, nuclei stain dark blue and other tissue constituents are pale blue).

Ziehl-Neelsen staining was used for qualitative assessment, which was made by comparing the number of organisms and their density within the stained tissue. The level of infection in the lungs, livers and spleens originating from various groups of mice was compared for each specific organ, but could not be compared among different organs, due to the difference in appearance and size of lesions characteristic for individual organ types.

Biochemical assessment

Five to seven weeks after the infection with *M. tuberculosis*, the mice were sacrificed for cytokine profiling, the required organs removed aseptically and snap-frozen in liquid nitrogen. The frozen organs were maintained at −70° C. and analyzed for the expression of various cytokines.

1.2.17 Methods Used in the Semi-Quantitative Competitive Reverse Transcriptase Polymerase Chain Reaction (SQC-RT-PCR) Determination Background information:
RT-PCR—Principle The Polymerase Chain Reaction (PCR) is a technique used for the amplification of DNA and the complementary DNA (cDNA) of specific mRNAs, which was invented by Mullis in the late 1980's (Mullis and Faloona 1987; Saiki et al., 1988) for the amplification of DNA sequences in vitro.

PCR is based on a series of incubation steps carried out at different temperatures. The template DNA (or cDNA) is denatured at a temperature above 90° C. (denaturing step). The oligonucleotide primers are then annealed to the single stranded DNA (ssDNA) at a temperature varying between 50° C. and 60° C., depending on the type of primers used (annealing step). This process is followed by an extension of the primers by incorporating dNTPs, using a heat-resistant DNA polymerase and an incubation temperature of 70–72° C. (extension step). The extension products of one primer provide templates for the other primers in subsequent cycles, so that each successive cycle essentially doubles the amount of DNA synthesised in the previous cycle. The result is the exponential amplification of the target DNA to approximately $2^n$ (n=number of cycles) (Zubay, 1993; Tamarin, 1996).

Taking into consideration a number of variables[*] which may interfere with the quantification of the exact amount of mRNA originally present in the analyzed sample, an improved technique, that of Semi-Quantitative Competitive Reverse Transcriptase Polymerase Chain Reaction, was employed.

[*] The variables include: differences in the stability and purity of polymerase enzyme, dNTP and in buffer preparation in various batches; $Mg^{2+}$ concentration; DNA (template) concentration; primer concentrations; annealing, extension and denaturing temperatures; length and number of cycles; rate of primer-dimer formation; presence of contaminating DNA.

Scanning of gels was done with a densitometer (Apple Mac). The density of the unknown cDNA band was compared to the density of that of β-actin and the concentration of the unknown cDNA could thus be estimated. The relative densitometric measurements were done using a Macintosh NIH Image Program.

This technique can be used to accurately quantify less than 1 fg (femtogram, $10^{-15}$ g) of target cDNA obtained from total RNA after the RT reaction. The accuracy of this method can be improved by using the same master mix for all the samples. The master mix should contain the appropriate primers, PCR buffer, dNTPs, $MgCl_2$ and the polymerase enzyme. The mix should be divided equally between all the tubes used for the PCR.

The competitive plasmid for murine IL-12 p40 (obtained as a gift from K. L. Bost, University of Tulane, New Orleans, La., USA) was a pGEM-3Z derivative with a IL-12 fragment (334 base pairs) cloned into the Xba I site from the multi-cloning site of the vector (Bost and Clements, 1995).

The construction of the plasmid was described by Bost and Clements (1995) and Chong, Bost and Clements (1996).

1.2.17.1 Preparation of the Organs Used for RNA Extraction

The organs originating from both infected and uninfected mice, used for the RNA extraction experiments were lungs, spleens and kidney. Mice were sacrificed by rapid cervical dislocation. The organs were removed from each mouse aseptically, and kept at −70° C. after snap-freezing in liquid nitrogen.

A single-cell suspension of the spleen was made by cutting the spleen into small pieces on a nylon sieve (70 μm mesh) in the presence of ice cold medium (DMEM containing streptomycin and sodium pyruvate). The spleen cells were concentrated by centrifugation and the excess of medium was removed. The erythrocytes present in the preparation were lysed by hypotonic shock, i.e., by treating the cells with a ⅒ dilution of DMEM in sterile distilled water for 15 seconds. The lysis of the cells was stopped by adding excess medium. After centrifugation, the excess medium was removed and the cells were snap-frozen in liquid nitrogen (McCarron, et al., 1984). The cells were maintained as a dry pellet at −70° C.

1.2.17.2 RNA Extraction from Control and Infected Organs

RNA was isolated from all the organs using the TRI-Reagent protocol based on an acid guanidium thiocynate-phenol-chloroform extraction, a method first developed by Chomczynski and Sacchi (1987). The isolated RNA was quantified by a Shimadzu UV-Visible Recording Spectrophotometer model UV-160, at wave-lengths of 260 nm and 280 nm. Pure RNA (absorption ratio at 260/280 nm>/=2.0) was used for PCR.

Integrity of the isolated RNA was determined using a denaturing formaldehyde gel (Maniatis, 1982). These denaturing conditions prevent degradation of the RNA by RNases. The water used in these experiments was diethyl pyro-carbonate (DEPC)-treated.

Ethidium bromide was added to the RNA sample, before it was loaded on the gel, at a concentration of 0.5 ng/ml to enable visualization of the DNA with UV light. Pure, undegraded RNA giving the three rRNA bands (the 28S rRNA, 18S rRNA and the 5S rRNA) on agarose gel electrophoresis, was used for the reverse transcriptase reaction (Maniatis, 1982).

1.2.17.3 The Optimization of the Different Cytokine PCRs and the β-actin PCR

Cytokine PCRs were optimised by using different plasmids containing DNA sequence fragments of the various cytokines to be evaluated/to be tested. These fragments of DNA are deletion mutations of fragments of the wild type cDNA for the individual cytokine. Both the mutated and the wild type cDNA can be amplified by using the same primers.

Three different plasmids were used for this purpose:
i) a plasmid used for the determination of IL-12 was obtained from K Bost (University of Tulane, USA);
ii) a plasmid used for the determination of TNF-α was obtained from R L Tarleton (University of Georgia, USA);
ii) a plasmid used for the determination of IL4, IL-10, IFN-γ and TGF-β was obtained from R M Locksley (University of California, San Francisco USA).

1.2.17.4 The Amplification of the Competitor Plasmids

The competitive plasmids for the determination of IL-12, TNF-α, TGF-β were amplified after transformation in the SURE E. coli strain and isolated with the Qiagen mini preparatory column kit. The recovered plasmids were resuspended in TE buffer (10 mM Tris pH 8, 1 mM EDTA) and stored at −20° C.

A list of the sequence of sense and anti-sense primers, their annealing temperatures and the wild type fragment size is given below in Table 3.

and Clements (1995). The protocol was adjusted due to a different type of PCR apparatus and to a different enzyme used (see Table 3).

The enzymes used in the SQC-RT-PCR during the exploratory phase were Dynazyme (Recombinant Taq Polymerase). Amplitaq Gold (Taq polymerase) was used in the final PCR experiments. Amplitaq Gold is a more sensitive and heat-stable enzyme-antibody complex, which is activated at temperatures above 90° C. The PCR conditions for using these two enzymes differ.

For Dynazyme, a 3 min Hot Start (3 min at 96° C. followed by 1 min at 80° C.) was required before the enzyme was introduced into the reaction mixture. After the enzyme was added, three cycles consisting of:
45 sec at 94° C.
followed by 75 sec at 58° C. and
105 sec at 72° C.
were run to initiate the synthesis of the second cDNA strands.

The subsequent amplification cycle consisted of the following shorter steps:
35 sec at 94° C.,
45 sec at 58° C. and
75 sec at 72° C.
This cycle was repeated 29 times.

Because Amplitaq Gold enzyme is heat stable, the enzyme was added before the PCR cycling was initiated by an incubation step for 10 min at 94° C. At this temperature, the enzyme became activated. The rest of the cycling profile remained the same as for the Dynazyme enzyme.

The optimum concentration of $MgCl_2$ and primer was determined for each enzyme in a series of experiments.

TABLE 3

A list of the sequences of the sense and antisense primers, their annealing temperature and the wild type fragment size

| Type of PCR | Sequence of the primers | Fragment Size | Annealing temperature |
|---|---|---|---|
| 1. β-actin[1] | S:5'CTC CAT CGT GGG CCG CTC TAG3'- AS:5'GTA ACA ATG CCA TGT TCA AT3' | 133 bp | 59°C. |
| 2. IL-12[2] | S:5'CCA CTC ACA TCT GCT GCT CCA CCA G3' AS:5'ACT TCT CAT AGT CCC TTT GGT CCA G3' | 266 bp | 60°C. |
| 3. TNF-α[3] | S:5'GTC TAC TTT AGA GTC ATT GC3' AS:5'GAC ATT CGA GGC TCC AGT G3' | 275 bp | 48 °C. |
| 4. TGF-β[4] | S:5'ACA GGG CTT TCG ATT CAG CGC3' AS:5'CAC CTA GGT GCT CGG CTT CCC3' | 306 bp | 60 °C. |
| 5. IFN-γ[4] | S:5'CAT TGA AAG CCT AGA AAG TCT G3' AS:5'GCT TTT TCC TAC GTA AGT ACT C3' | 267 bp | 60 °C. |
| 6. IL-10[4] | S:5'CCA GTT TTA CCT GGT AGA AGT GAT G3' AS:5'AAC TCA GAC CTG AGG TCC TGG ATC TGT3' | 324 pb | 60 °C. |

1. Ma et al 1994
2. Chong et al, 1996.
3. Benavides et al, 1995.
4. Reiner et al, 1994.

1.2.17.5 Semi-Quantitative Competitive Reverse Transcriptase Polymerase Chain Reaction (SQC-RT-PCR) Determination of IL-12

The primers were individually diluted in TE to a concentration equal to 132–133 pmol). PCR reactions, carried out using the MJ Research Peltier Thermal Cycler (PTC-200), were performed based on the protocol developed by Bost Each PCR reaction mix consisted of 2 mM $MgCl_2$ (for Dynazyme) or 1.5 mM $MgCl_2$ (for Amplitaq Gold), 0.2 mM dNTP, PCR buffer supplied with the enzyme and 2U polymerase enzyme, 500 ng of each primer and plasmid DNA was added to the mixture. The final reaction mixture volume was made up to 50 μl with sterile deionised water.

A first QC-RT-PCR approach protocol was described by Bost and Clements (1995) for interleukin 12. For the QC-RT-PCR both the RT mix and the IL-12 p40 plasmid DNA were added to the reaction mixture. The RT-mix (for the first strand cDNA) had a total volume of 20 µl. This volume was divided into different percentages eg. 60% ; 20% ; 6% ; 3% etc, according to the protocol of Bost and Clements (1995). A constant concentration of plasmid DNA was added to the PCR reaction mix.

A different approach described by Chong, Bost and Clements (1996)was subsequently applied for optimization of PCR conditions. According to this protocol, tile RT-mix was constant at 20% (4 µl of RT-mix were used), and different concentrations of the plasmid DNA were added. Plasmid was added in the following dilution range: 0.5, 0.25, 0.125, 0.062, 0.032, 0.016 and 0.008 pg.

The final PCR product was visualised on a 2% agarose gel containing 0.5 µg/ml ethidium bromide. It was found that the digested plasmid gave better results than the undigested plasmid due to better denaturation of the plasmid material. The digestion was performed with the enzyme Xba I at 37° C. for 3 hours.

1.2.17.6 β-actin PCR

The β-actin PCR was performed as an indication of the amount of intact mRNA. Amplitaq Gold was used as DNA polymerase. The same PCR cycling protocol as that of IL-12 p40 was used, except for the annealing temperature for the β-actin primers which was 59° C. instead of 58° C. The elongation and amplification cycles were the same as that of IL-12 PCR.

The sequences of the primers used are given in Table 3.

Figure 2A:
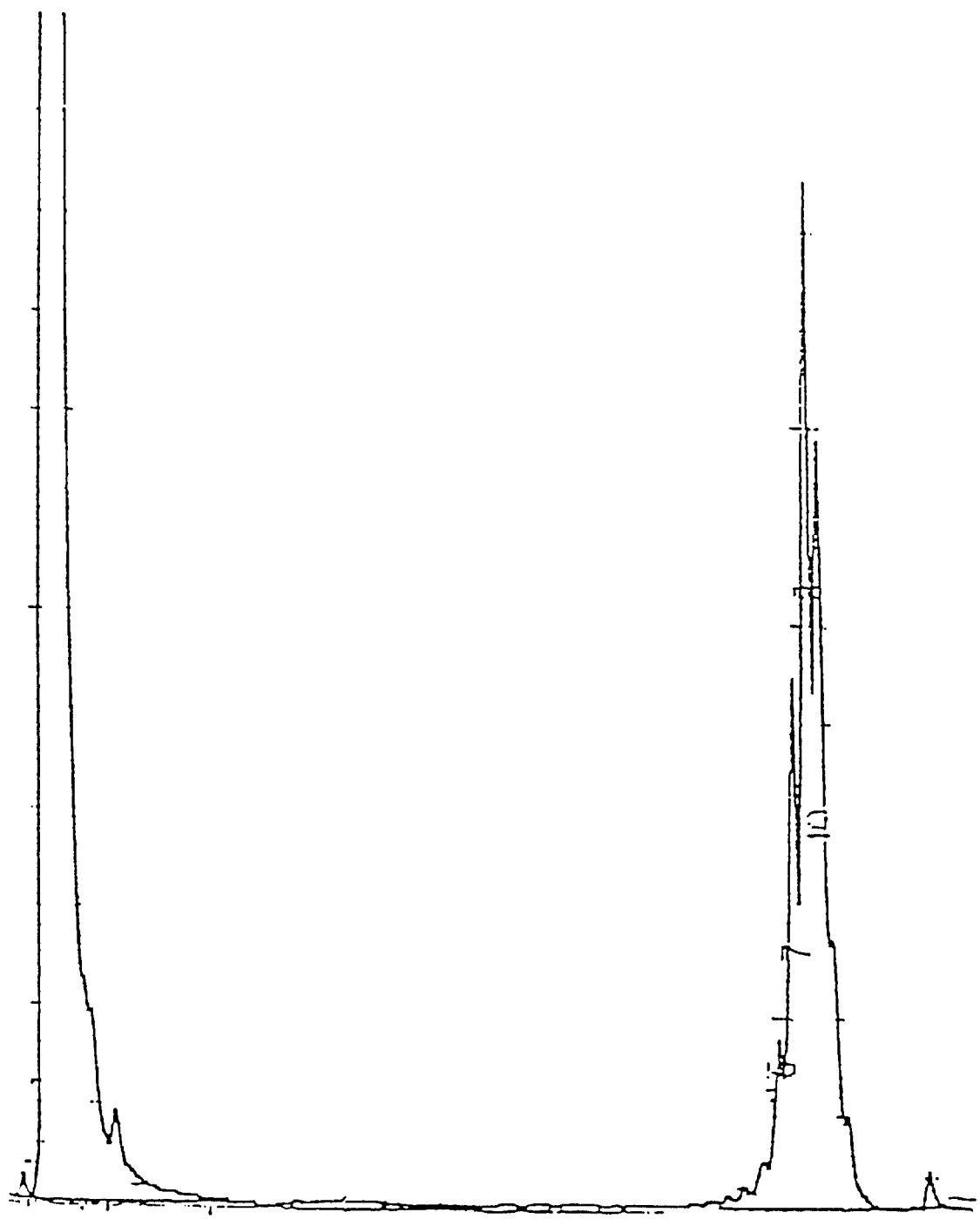
FIG. 2a is an HPLC profile of mycolic acids originating from *M. tuberculosis*, purified using the improved method of countercurrent distribution in a sodium-chloride containing phase system.
Figure 2B:
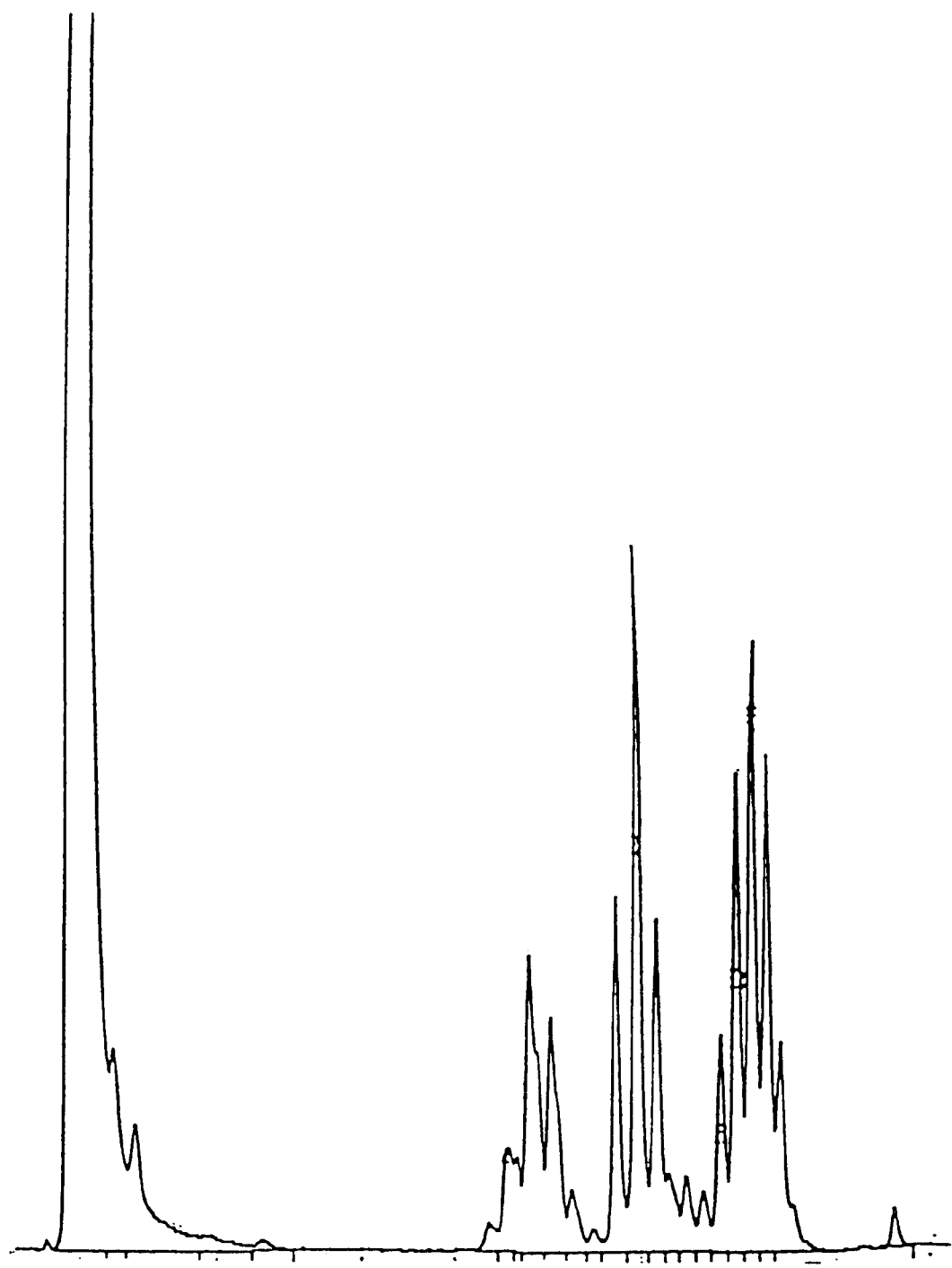
FIG. 2b is an HPLC profile of mycolic acids originating from *M. vaccae*, purified using the improved method of countercurrent distribution in a sodium-chloride containing phase system.

1.3 Results and Discussion 1.3.1 The Influence of the Modified Method of Purification on Yield and Purity of Mycolic Acids By applying modifications to the previously patented purification procedure (SA Patent Applications No 95/1464 and 96/1412), i.e., by using NaCl as described under 1.2.8 and 1.2.9, larger amounts of the extracted mycolic acids could be purified in a single run of countercurrent separation, without impairing the degree of their purity. This is illustrated by the results summarized in Table 4 as well as in FIGS. 2a and 2b, for mycolic acids originating from *M. tuberculosis* and *M. vaccae*, respectively. Although a yield of approximately 10% m/m of the purified mycolic acids was previously reported, it was subsequently established that yields of pure mycolic acids using either method, varied between 3 and 10% m/m depending on the particular batch of bacteria used for extraction

TABLE 4

Yield and purity of the mycolic acids originating from
*M. tuberculosis*, purified using the improved method

| Parameter | Original method | Method with NaCl |
| --- | --- | --- |
| Loaded mass of mycolic acids-crude extract | 31.1 mg | 3760 mg |
| Mass of countercurrent-purified mycolic acids | 3.5 mg | 218 mg |
| Equilibration time | 40 min | 5 min |
| Number of cycles | 24 | 30 |
| Duration of the run | 18 hours | 3.5 hours |
| Yield | 5.3%–10% | 5.8%–7.8% |

1.3.2 Structural Analysis of Mycolic Acids Originating from *M. tuberculosis*, Using Infra-red Spectroscopy In order to evaluate the influence of the process of saponification, freezing and storage on the conformation of purified mycolic acids, the infra-red spectra of a number of samples were analyzed.

Figure 3:
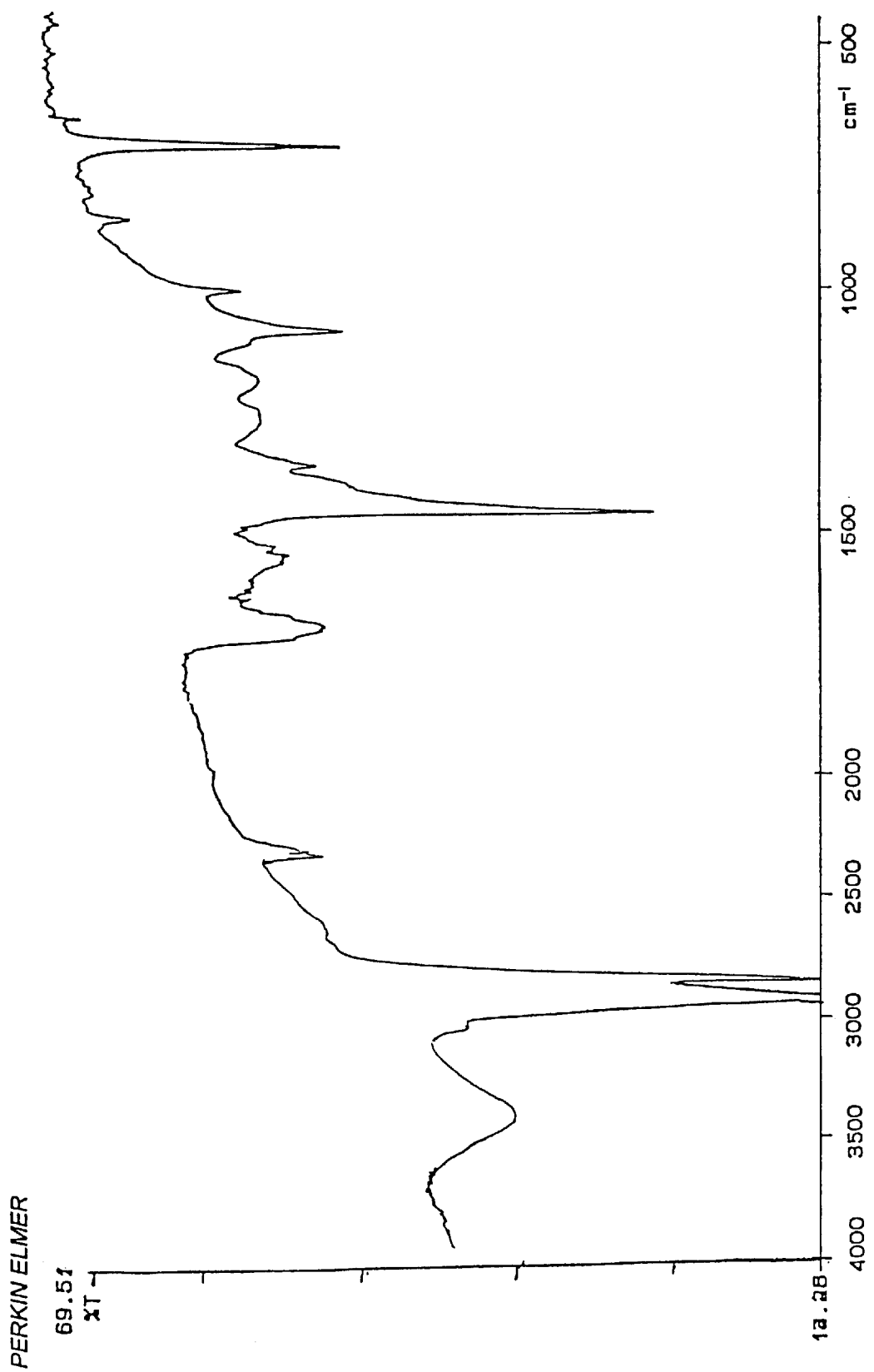
FIG. 3 is an infra-red spectrum of countercurrent purified mycolic acids, originating from *M. tuberculosis*.
Figure 4:
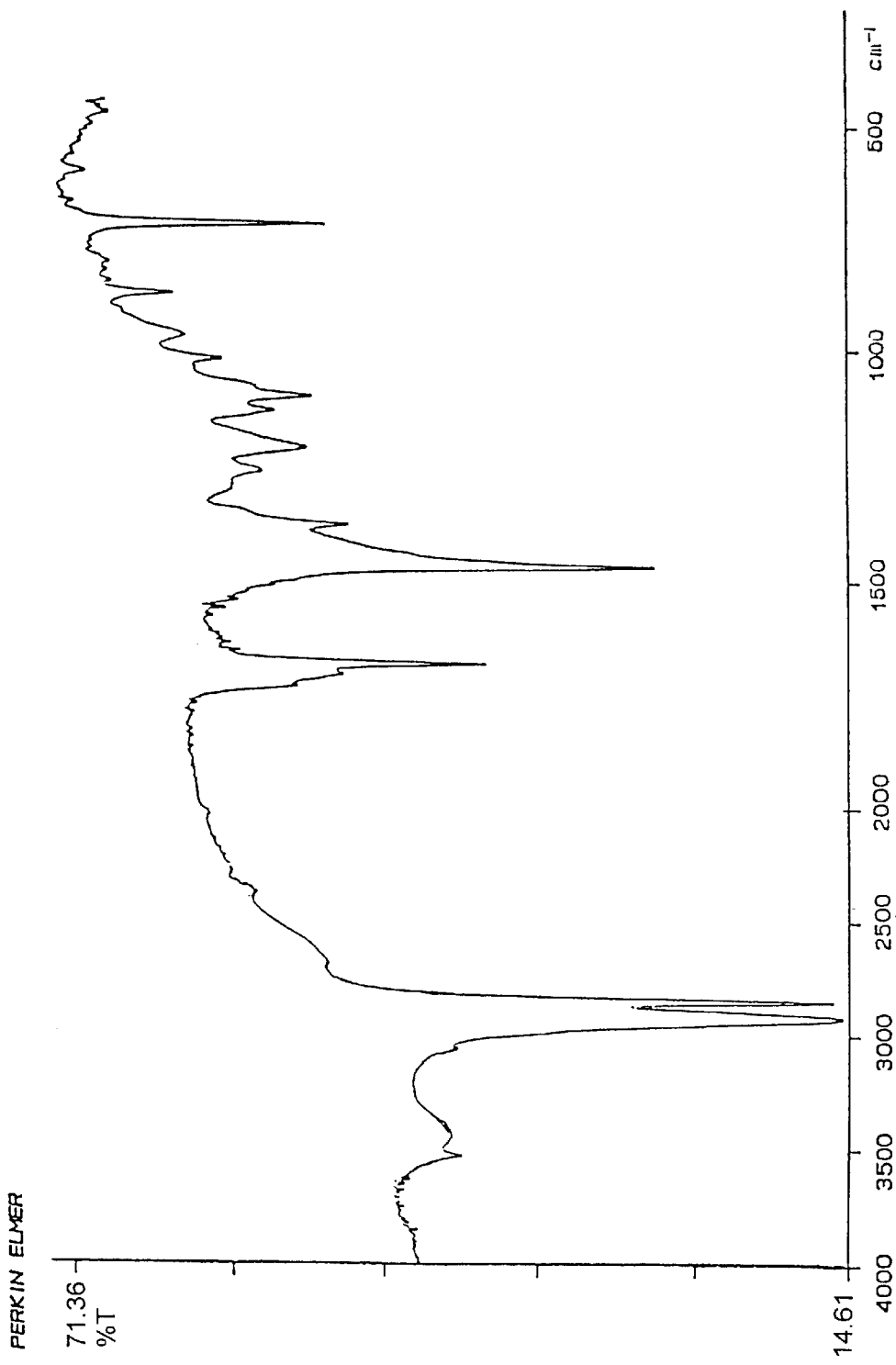
FIG. 4 is an infra-red spectrum of the resaponified countercurrent purified mycolic acids, originating from *M. tuberculosis*.
Figure 5:
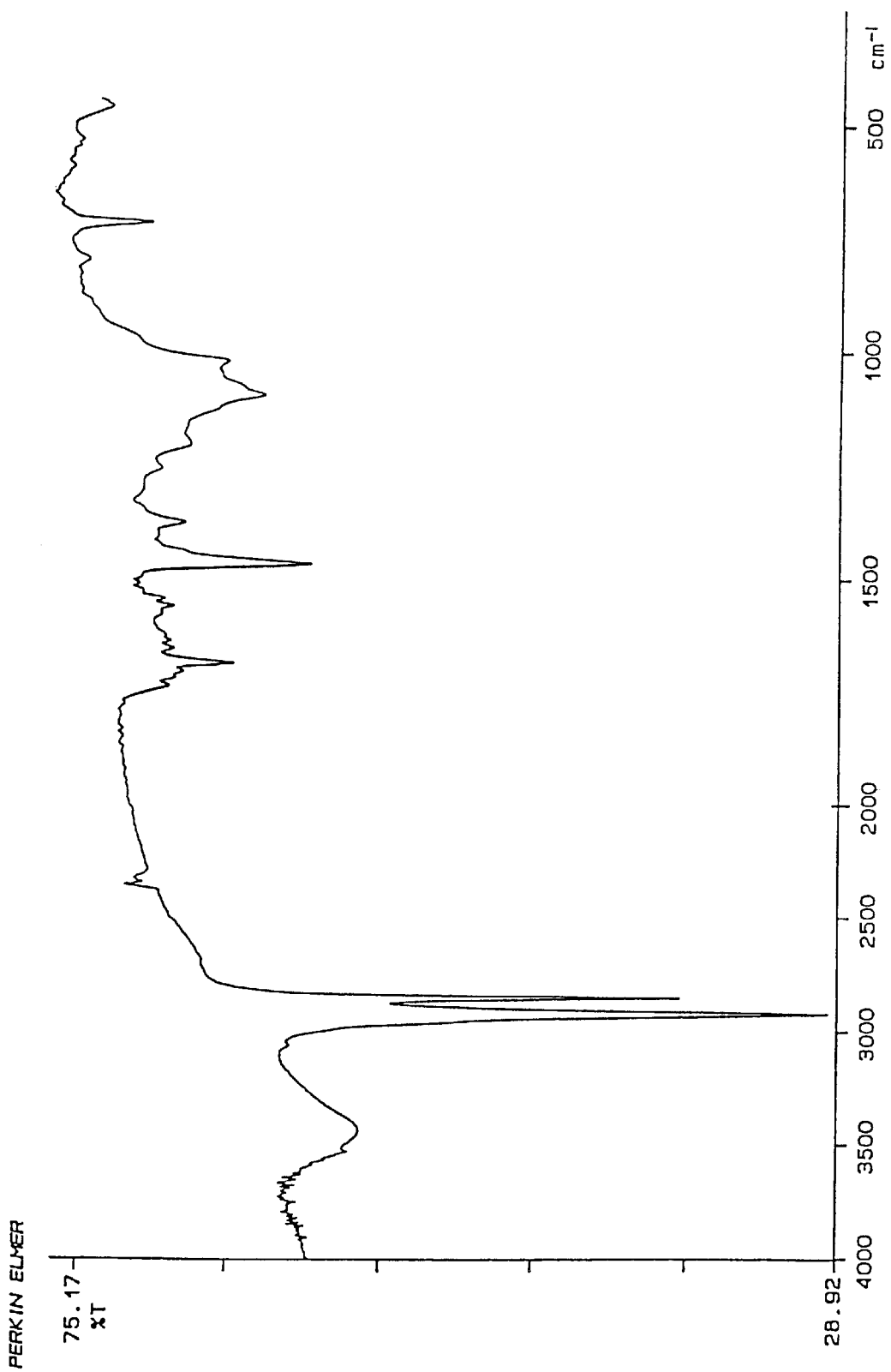
FIG. 5 is an infra-red spectrum of countercurrent-purified and resaponified mycolic acids, originating from *M. tuberculosis*, frozen at −70° C.
Figure 6:
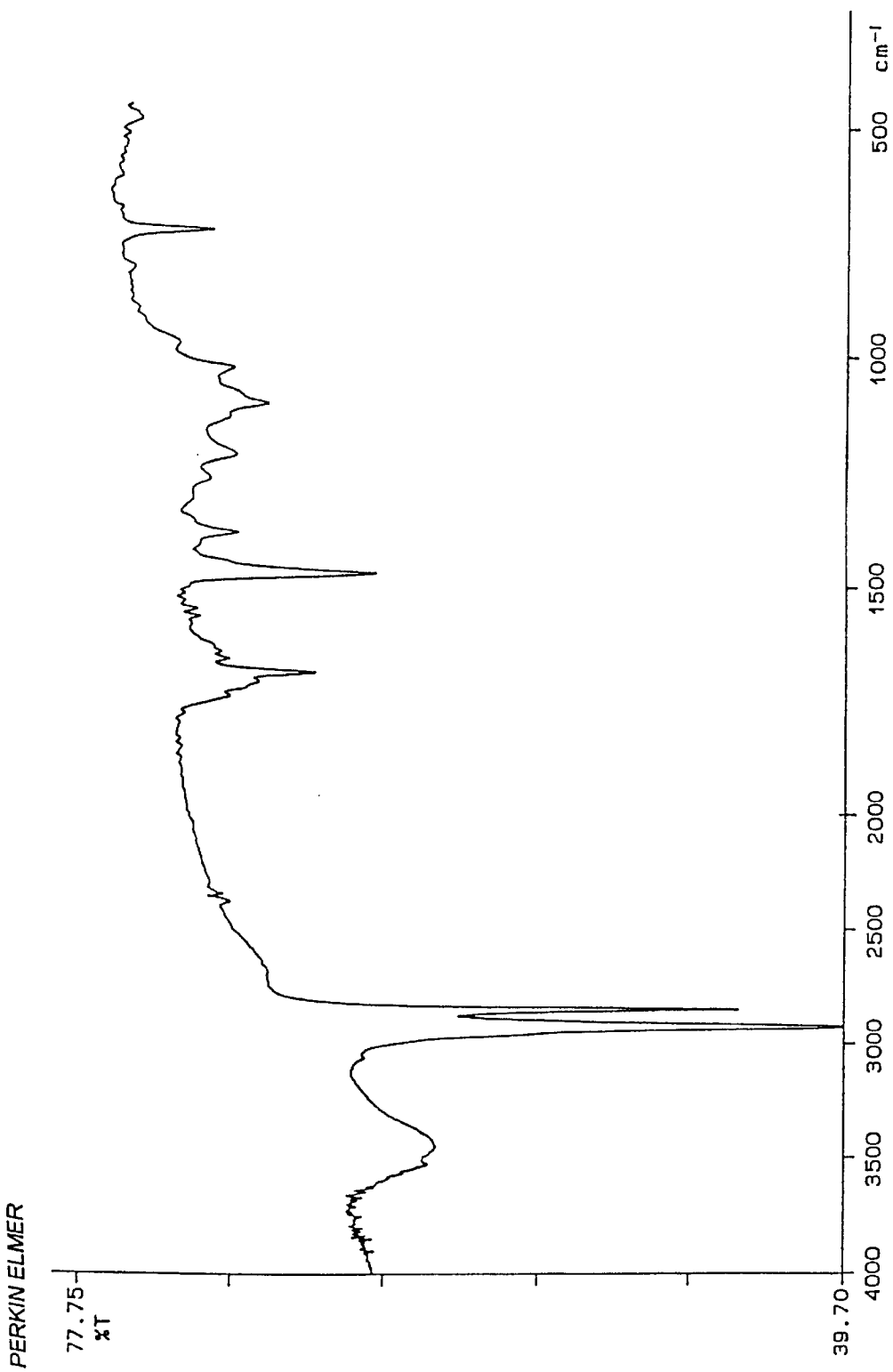
FIG. 6 is an infra-red spectrum of countercurrent-purified and resaponified mycolic acids, originating from *M. tuberculosis*, and maintained at 10° C.
Figure 7:
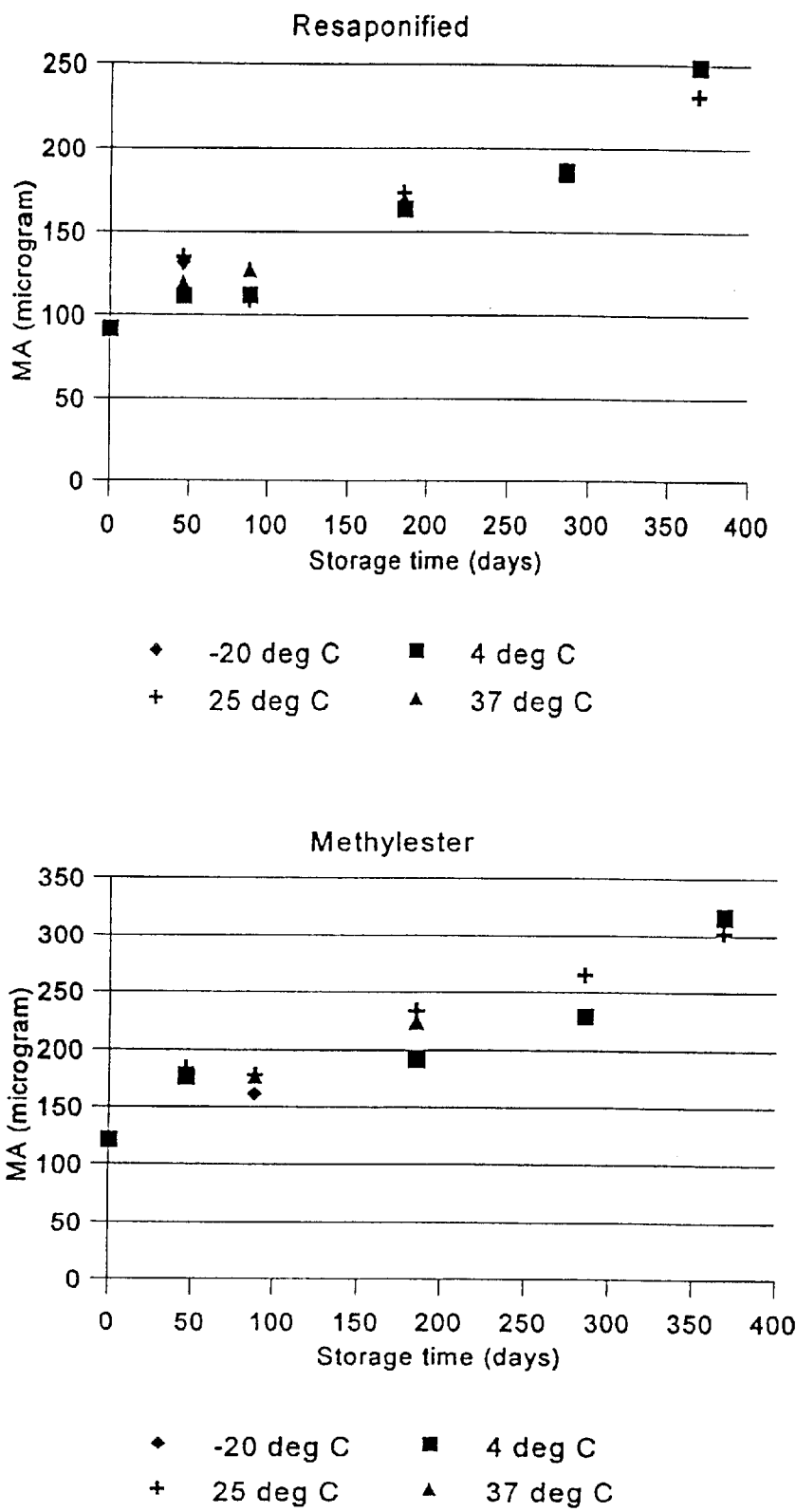
FIG. 7 shows the stability of mycolic acids originating from *M. tuberculosis* (resaponified and methylester form) upon dry storage.

The infra-red spectrum of countercurrent-purified mycolic acids, originating from *M. tuberculosis*, prior to saponification is presented in FIG. 3.

The spectrum in FIG. 3 provides evidence that mycolic acids after countercurrent purification exist in the methyl-ester form. The absence of a broad absorption band spanning the 3000–2000 $cm^{-1}$ frequency range indicates that there are no free carboxylic acids. The intense narrow band at 2800–2950 $cm^{-1}$ indicates aliphatic nature of the compound. In addition, the narrow band of absorption at 1750 $cm^{-1}$ indicates the presence of an ester form.

The infra-red spectrum in FIG. 4 shows the pattern observed after resaponification of the countercurrent-purified mycolic acids. The anticipated presence of free carboxylic acid groups could not be confirmed, which suggests that inter- or intra-molecular interaction of the carboxylic acids with other functional groups took place.

FIG. 4 also shows that this inter- or intra-molecular rearrangement of the carboxylic acids restricts the degree of aliphatic breathing (a decreased absorption in the 1720–1500 $cm^{-1}$ range) in comparison to that of the methyl ester form (FIG. 3), indicating a conformationally rigid structure. This would imply a significant structural alteration caused by the process of resaponification.

The carboxylic acids rearrangement over time did not manifest as changes observed in the infrared spectra. In addition, the influence of freezing at −70° C. and storage at 10° C. on the configuration of mycolic acids was also investigated. The respective infra-red spectra are presented in FIGS. 5 and 6.

Prior to freezing at −70° C. and storage at 10° C., the samples of mycolic acids were freshly resaponified. Freezing at −70° C. appears to loosen up the structure of mycolic acids and lead s to the increase of aliphatic breathing and "out of plane" bending within the molecules. This is probably due to the decrease in the strength of van der Waals' forces caused by the withdrawal of water as ice crystals.

1.3.3 Stability of Mycolic Acids

Stability of mycolic acids was investigated by maintaining equal aliquots of samples of countercurrent-purified mycolic acids in the methylester form as well as saponified mycolic acids, originating from the same batch, at −20° C, 4° C. and 25° C. for 12 months in either the dry form, precipitated under acetone, or dissolved in chloroform.

The results obtained after 12 months are summarized in FIG. 7 for mycolic acids stored in the dry state. Similar results were obtained for mycolic acids stored in the acetone-precipitated and chloroform-dissolved state, but with higher variance.

On the basis of the HPLC analysis of the various samples of mycolic acids stored at −20° C., 4° C. and 25° C., it was concluded that mycolic acids in either methylester or saponified form were stable for at least 12 months. The apparent gradual increase in absorptivity could be an artifact of calibrating the new internal standard with old samples of mycolic acids but is not due to a chemical process, which would have manifested itself by different values for different temperatures of storage.

1.3.4 Immunoregulatory Properties of Countercurrent-purified Mycolic Acids

Investigations of the immunoregulatory properties of countercurrent-purified mycolic acids were centred on two main aspects, i.e.:

i) their ability to extend the survival of the *M. tuberculosis*-infected mice; and ii) their cytokine profile in various organs over short and long term with or without concomitant infection with *M. tuberculosis.*

These investigations were based on the following experiments:

i) The investigation into the influence of pre- and post-treatment of the experimental mice with resaponified mycolic acids on their survival after the infection with M. tuberculosis;

ii) The immunoregulatory effect of mycolic acids on the expression of interleukin 4 (IL4), interleukin 10 (IL-10), interleukin 12 (IL-12), interferon γ (IFN-γ), tumour necrosis factor α: (TNF-α) and transforming growth factor β (TGF-β) in the lungs of M. tuberculosis-infected and non-infected experimental animals.

Figure 9:
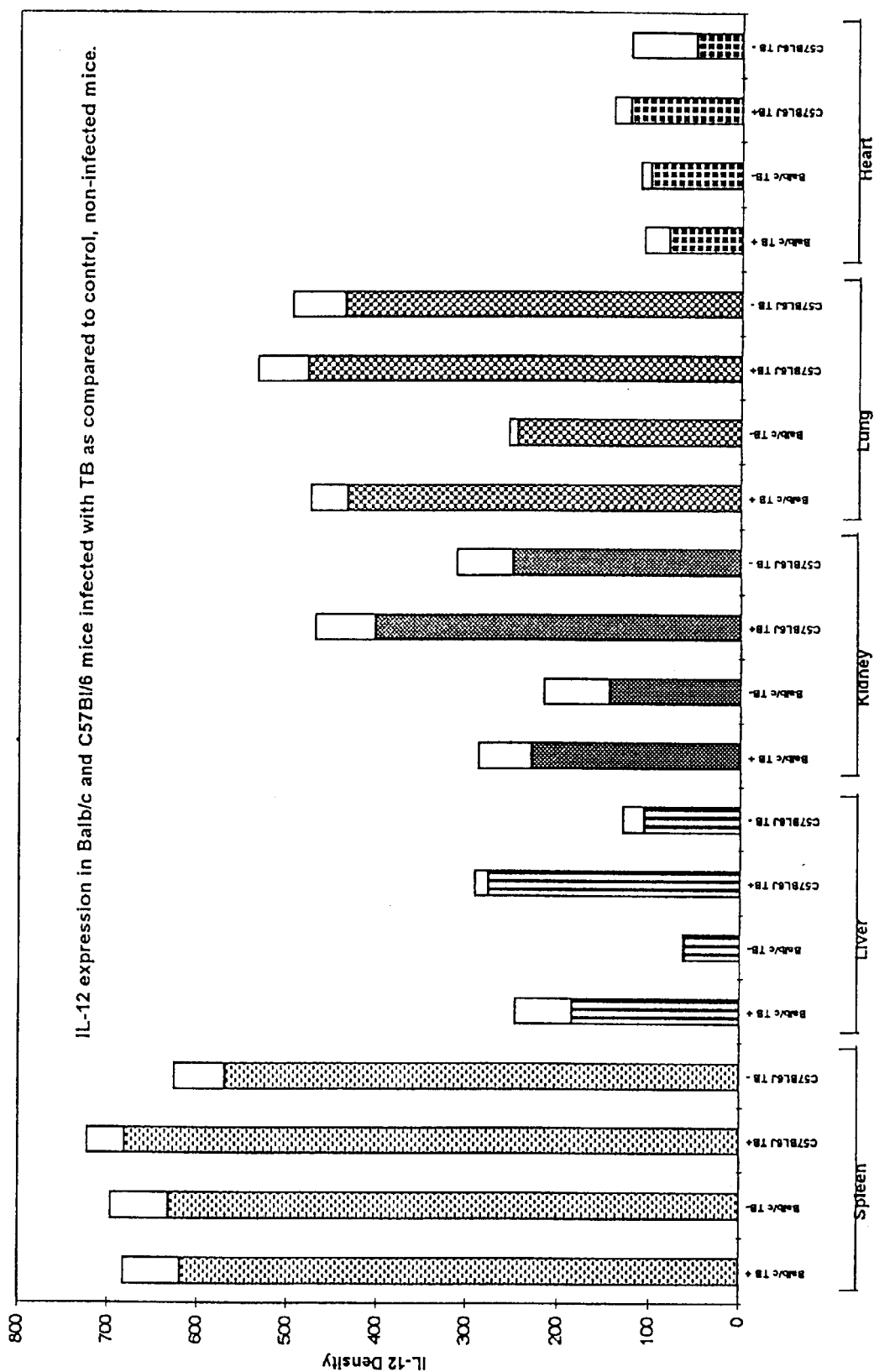
FIG. 9 shows the expression of IL-12 in the spleen, liver, kidney, lung and heart of Balb/c and C57B1/6 mice two weeks after the infection with *M. tuberculosis*.

Before the results obtained in the course of this investigation are presented and discussed, a number of technical aspects having a direct influence on the outcome of the experiments as well as on the repeatability of various immunoregulatory experiments is listed and briefly discussed below:

1. The infection with *M. tuberculosis* was introduced not by inhalation but by intravenous injections. Although the inhalation is a more natural method of infection, it is very difficult to control and consequently to quantify the number of mycobacterial cells introduced. The intravenous injections permitted a more accurate introduction of the intended dose of *M. tuberculosis.*
2. The introduction of the mycolic acids-mouse serum conjugates to the experimental mice was likewise done by intravenous injections. This method is however restricted by procedural difficulties. The difficulties are associated with the introduction of a thick suspension in relatively large volumes into a vein of the mouse tail. Not infrequently this procedure leads to a leakage of the introduced material.
3. The preparation of mycolic acids-mouse serum conjugate involves a random adsorption process which normally does not result in a uniform distribution of mycolic acids over the surface of mouse serum protein.
4. The actual number of live cells of Mycobacterium in the introduced dose is very difficult to establish and can differ from the intended number of bacterial cells. The number of viable bacteria is usually determined on the basis of the number of colonies formed when a suspension of the bacteria to be enumerated, appropriately diluted, is spread on the surface of a solid growth medium and incubated. Ideally, such a suspension should consist of single bacterial cells. The living bacteria, in the presence of required nutrients will multiply, and, within a short period of time (24–48 hours), each living cell should give rise to a single colony. However, in the case of bacteria which form long chains or clusters of cells, or which branch and do not separate easily during the preparation of the suspension, a single colony will frequently originate from a cluster of living cells. In such cases, the number of colonies formed is lower than the actual number of living cells in the enumerated suspension, and is denoted by the term "colony forming units" (cfu)" rather than the viable number of cells.

Mycobacterium cells during multiplication tend to branch and this in turn leads to the formation of cell clusters. Such clusters are difficult to disrupt and convert to a unicellular suspension, despite attempts aimed at homogenising the suspensions. When introduced on to the surface of solid media such clusters, comprising a number of cells will, form colonies. Therefore, an underestimation of the number of viable cells is usually obtained.

5. Variations in the stability of individual interleukin MRNA in various organs (discussed in the Background to the Invention, section 3.2) constitute another source of inaccuracies in the determination of cytokine profiles.
6. The mouse serum, used as a carrier of mycolic acids in some of the experiments, was found not to be a neutral molecule, but to possess non-specific immunoregulatory activity. Therefore, the protective properties of the purified mycolic acids, reported in these investigations, might have been distorted, and to a certain degree even decreased, by the immunological activity of mouse serum.
7. Taking also into account low accuracy, typical of densitometric quantification of electrophoresis bands, the cytokine profiling reported in the work was undertaken as a tentative, qualitative screening only.

Preliminary experiments

The aim of these experiments was to determine the effects of resaponified mycolic acids on healthy, uninfected mice and to confirm the difference in the resistance of Balb/c and C57B1/6 mice to the infection with *M. tuberculosis.* These experiments are discussed in sections 1.3.4.1 and 1.3.4.2.

1.3.4.1 The Influence of Treatment of the Experimental Mice with Resaponified Mycolic Acids Originating from *M. tuberculosis*

In order to investigate the effects of mycolic acids on the experimental animals, Balb/c mice were injected with 250 μg mycolic acids/mouse serum conjugate. After a boost with 25 μg mycolic acids/mouse serum conjugate two weeks later, short (24 and 48 hours) and long term (14 days ) effects of this treatment were measured. The cytokine profiles of IL-12, IFN-γ, TNF-α and TGF-β in the lungs of the mycolic acids-treated mice and the control, serum-treated mice, were determined. No significant response to the mycolic acids/mouse serum conjugate was observed in the spleens of the experimental animals. The cytokine profiles, of IL-12, IFN-γ, TNF-α and TGF-β in the lungs are presented in FIG. 8.

As becomes apparent from FIG. 8, levels of the pro-inflammatory cytokines, IL-12 and of IFN-γ, in the lungs of mice treated with mycolic acids/mouse serum conjugate were higher than those observed for the mice treated with serum only. For the anti-inflammatory. TGF-β, there was no significant difference between the levels observed in the lungs of the mice treated with mycolic acids/mouse serum conjugate and those treated with mouse serum only. The results obtained for the pro-inflammatory TNF-α show that this cytokine appears responsive towards the treatment with mouse serum only.

1.3.4.2 The Resistance of Balb/c and C57B1/6 Mice to the Infection with *M. tuberculosis*

The variable resistance of different mouse strains towards the infection with *M. tuberculosis* has been reported not to be due to genetic differences of the major histocompatibility (MHC) gene complex. Rather, the genetic difference responsible for the extent to which interleukin 12 (IL-12) is synthesized and secreted by various strains of mice appeared to be one of the responsible factors (Flynn et al., 1995). Expression of the inducible IL-12 is lower in spleens from mice susceptible to infection with *M. tuberculosis* compared to the more resistant mouse stains (Kobayashi et al., 1996; Yoshida, Koide and Uchijima, 1995).

This conclusion was corroborated by our experiments using inbred Balb/c susceptible to infection with *M. tuberculosis* and C57B1/6, a more resistant mouse strain. Firstly, the survival studies were carried out to establish the degree of resistance of these mice. The results are presented in Table 5.

Secondly, IL-12 mRNA expression was compared in these two strains of mice. Balb/c and C57B1/6 mice were infected with equal doses of M. tuberculosis (approximately $10^5$ cells/mouse) and sacrificed after 14 days. The results presented in FIG. 9 indicate that the organs that responded in their IL-12 expression toward,; the infection with M. tuberculosis were the liver and kidneys in both strains an the lungs in only the susceptible Balb/c strain. In the lungs of the more resistant C57B1/6 strain, the uninfected organs already expressed a high level of IL-12, which did not change upon infection.

Figure 8:
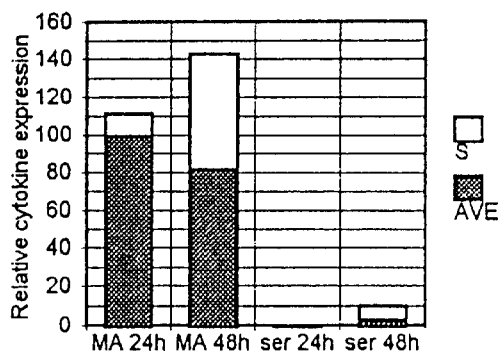
FIG. 8 shows cytokine profiles of IL-12, IFN-τ, TNF-α and TGF-β in the lungs of Balb/c mice treated with 250 μg and boosted with 25 μg mycolic acids from *M. tuberculosis*. The lungs were removed 24 and 48 hours after the boost.
Figure 8:
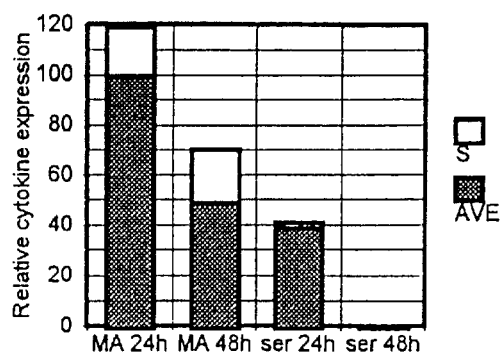
Figure 8:
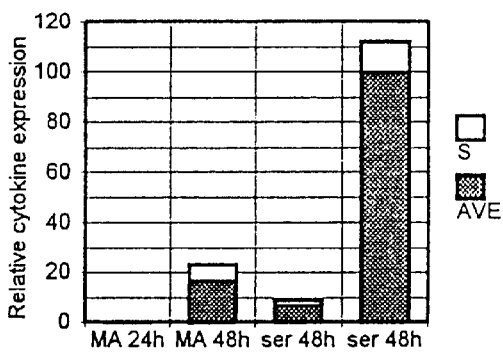
Figure 8:
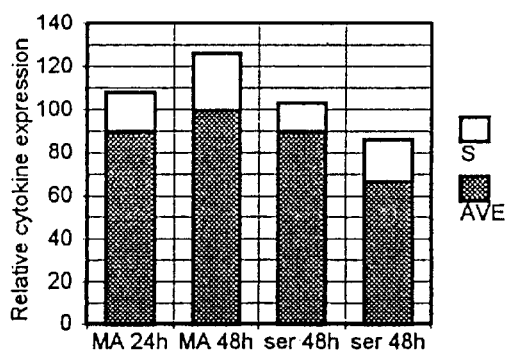

By treatment wit mycolic acids, IL-12 expression in the lungs was enhanced (see: FIG. 8) thus providing the protection typical of the more resistant strain. It is important to realise that the serum carrier on its own appeared to suppress the IL-12 levels in the animal organs (see point 6 in section 1.3.4).

TABLE 5

Survival of Balb/c and C57B1/6 mice upon infection with M. tuberculosis

| | Survival (weeks) | |
|---|---|---|
| Bacterial dose | Balb/c | C57B1/6 |
| $10^6$ | 3■ | 1■ |
| | 3■ | 3■ |
| | 3■ | 3■ |
| | 3■ | 3■ |
| | 3■ | 10■ |
| $10^5$ | 3■ | 15■ |
| | 3■ | 18■ |
| | 11o | 19o |
| | 11o | 20o |
| | 11o | 20o |
| $10^4$ | 6o | alive |
| | 7■ | alive |
| | 8o | alive |
| | 19o | alive |
| | 21o | 22o |

■ = Natural death due to tuberculosis
o = Death by euthanasia after severe TB symptoms have developed Immunoregulatory properties of mycolic acids originating from M. tuberculosis and M. vaccae The aim of these experiments was to establish whether mycolic acids originating from M. tuberculosis and M. vaccae could offer a degree of protection against tuberculosis to the experimental animals and whether such a protection was reflected in the profiles of the selected cytokines.

The results obtained in the treatment with mycolic acids preceding (pre-treatment) and following (post-treatment) the infection with M. tuberculosis are presented in sections 1.3.4.3, 1.3.4.4 and 1.3.4.5.

1.3.4.3 The Influence of Pre-treatment and Post-treatment of the Experimental Mice with Resaponified Mycolic Acids Originating from M. tuberculosis on Their Survival After the Infection with M. tuberculosis In order to establish whether the immunoregulatory properties of mycolic acids could protect against or enhance the susceptibility to the infection with M. tuberculosis, an experiment described in section 1.2.16 was carried out. The expression of IL-4, IL-10, IL-12, IFN-γ, TNF-α and TGF-β was measured by PCR in the tissues originating from the lungs and spleens of the experimental animals.

Figure 10:
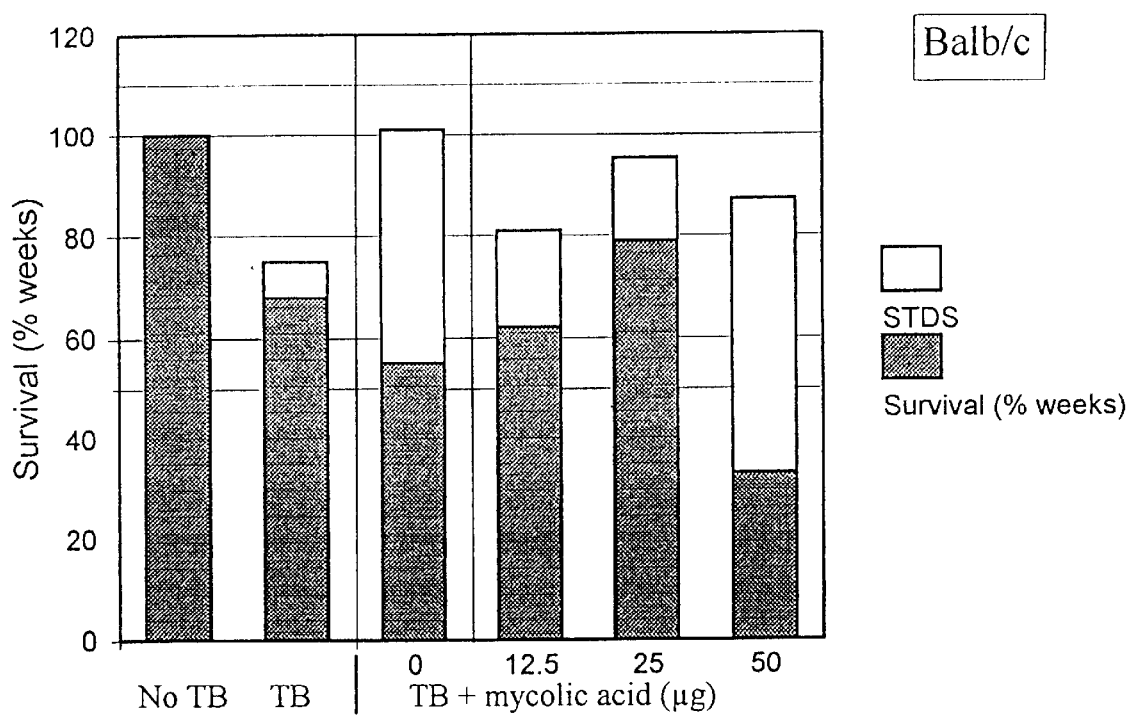
FIG. 10 shows the survival of *M. tuberculosis*-infected Balb/c mice, pre-treated with mycolic acids (from *M. tuberculosis*) one week before the infection, at the indicated doses.
Figure 11:
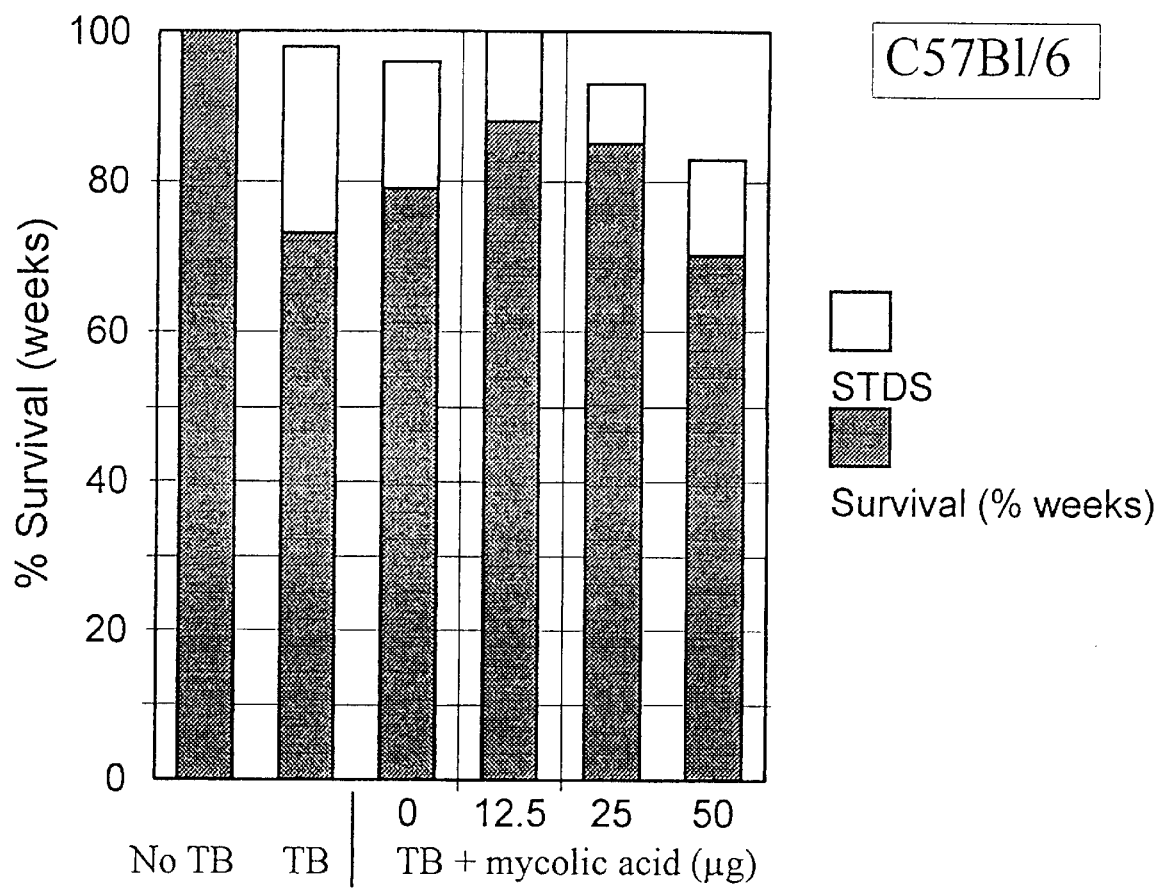
FIG. 11 shows the survival of *M. tuberculosis*-infected C57B1/6 mice, pre-treated with mycolic acids (from *M. tuberculosis*) one week before the infection, at the indicated doses.
Figure 12:
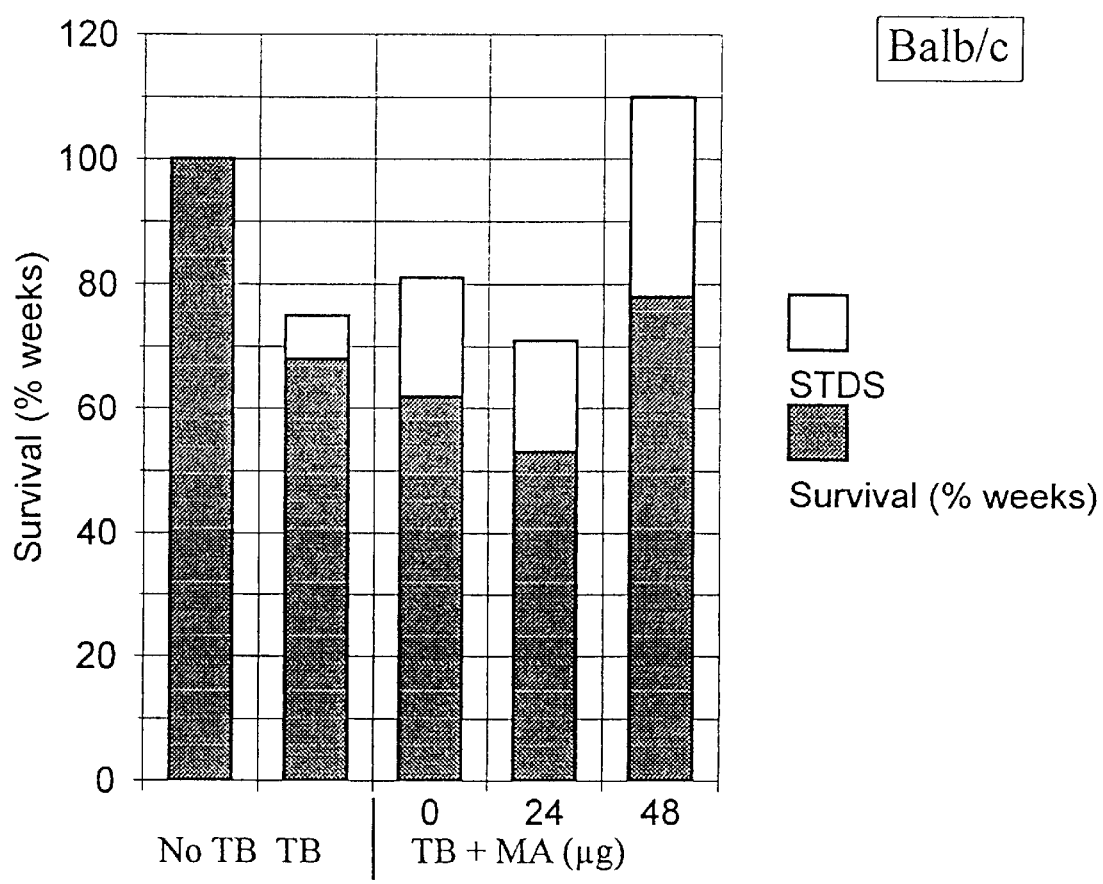
FIG. 12 shows the survival of *M. tuberculosis*-infected Balb/c mice post-treated with mycolic acids (from *M. tuberculosis*) three weeks after the infection, at the indicated doses, delivered in three daily injections of equal dose.
Figure 13:
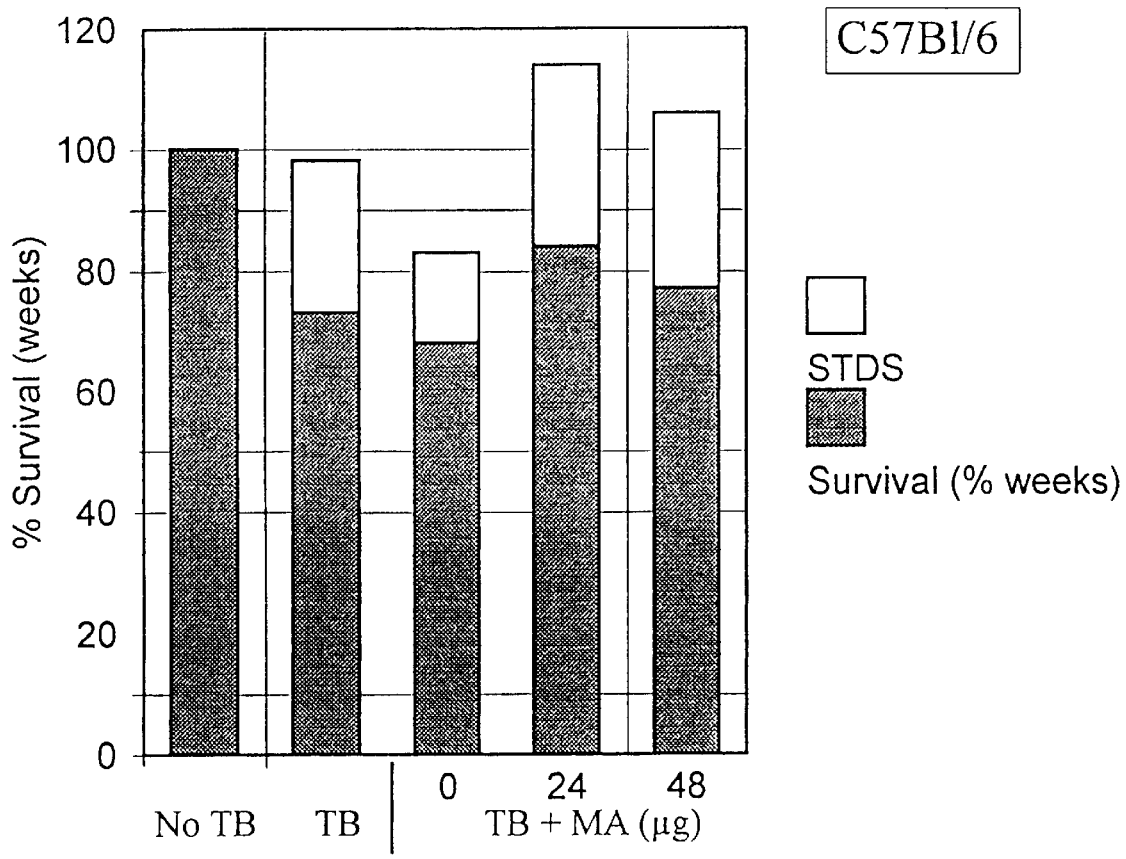
FIG. 13 shows the survival of *M. tuberculosis*-infected C57B1/6 mice post-treated with mycolic acids (from *M. tuberculosis*) three weeks after the infection, at the indicated doses, delivered in three daily injections of equal dose.

The results obtained in IR IV provide evidence that pre-treatment of Balb/c mice with 25 μg mycolic acids, one week prior to the infection with M. tuberculosis, enhanced the survival of the infected mice (FIG. 10). This protective effect was also seen in C57B1/6 mice but was less pronounced (FIG. 11). The introduction of mycolic acids to Balb/c mice three weeks after infection with M tuberculosis, did not lead to protection (FIG. 12). At double the dose, however, a degree of protection was observed illustrating the potential of mycolic acids also as an anti-tuberculosis agent (FIG. 12). Protection was also observed in M. tuberculosis-infected C57B1/6 mice upon post-treatment with mycolic acids three weeks after the infection (FIG. 13).

In two more experiments (Nos IR III and IR VII), mycolic acids induced protection, while in another experiment (IR V) less significant differences in survival were observed between treated and non-treated animals (results not shown). In the latter case, the duration of survival before the first death occurred was considerably longer, suggesting that protection was provided especially when relatively large doses of pathogenic bacteria were administered. In IR V however, macroscopic observation of the degree of tubercle formation in the infected lungs showed a degree of protection in the mycolic acids-treated animals seven weeks after the infection, with no evidence for protection in other organs (Table 6). It therefore appears probable that at subacute doses of the pathogen, a short term protection of the lung by mycolic acids pre-treatment could be rendered redundant due to the progression of the infection in the other organs.

The assessment of pathological changes in the organs dissected from the mice is presented in Table 6.

TABLE 6

Assessment of pathological changes in the organs dissected from mice of immunoregulatory experiment No V (IR V)

| | | 1st Organ extraction (5 weeks) | | | | 2nd Organ extraction (7 weeks) | | | | 3rd Organ extraction (11 weeks) | | |
|---|---|---|---|---|---|---|---|---|---|---|---|---|
| Group | M | Spleen | Lungs | Liver | M | Spleen | Lungs | Liver | M | Spleen | Lungs | Liver |
| - TB infection | 1 | norm | norm | norm | 1 | norm | norm | norm | 1 | — | — | — |
| | 2 | norm | norm | norm | 2 | norm | norm | norm | 2 | — | — | — |
| | 3 | norm | norm | norm | 3 | norm | norm | norm | 3 | — | — | — |
| - TB infection | 1 | > | ++ | norm | 1 | >> | + | red | 1 | >> | +++ | norm |
| | 2 | > | ++ | norm | 2 | >>> | ++ | red | 2 | > | +++ | red |
| | 3 | > | ++ | red | 3 | >>> | +++ | red | 3 | >> | +++ | norm |
| MA tb pre-treated | 1 | > | ++ | red | 1 | norm | + | norm | 1 | > | ++ | norm |
| | 2 | > | +++ | red | 2 | > | + | norm | 2 | > | ++ | norm |
| | 3 | > | +++ | red | 3 | > | + | norm | 3 | > | ++ | norm |

TABLE 6-continued

Assessment of pathological changes in the organs dissected from mice of immunoregulatory experiment No V (IR V)

| Group | | 1st Organ extraction (5 weeks) | | | | 2nd Organ extraction (7 weeks) | | | | 3rd Organ extraction (11 weeks) | | |
|---|---|---|---|---|---|---|---|---|---|---|---|---|
| | M | Spleen | Lungs | Liver | M | Spleen | Lungs | Liver | M | Spleen | Lungs | Liver |
| MA vaccae pre-treated | 1 | > | ++ | norm | 1 | > | + | red | 1 | > | +++ | norm |
| | 2 | > | ++ | red | 2 | > | + | red | 2 | > | +++ | norm |
| | 3 | > | +++ | norm | 3 | >> | + | norm | 3 | >> | ++ | red |
| Serum pre-treated | 1 | > | ++ | norm | 1 | >> | +++ | norm | 1 | > | ++ | norm |
| | 2 | > | +++ | red | 2 | >>> | +++ | norm | 2 | >> | ++ | norm |
| | 3 | > | ++ | red | 3 | > | ++ | norm | 3 | > | ++ | red |
| MA tb post-treated | 1 | > | +++ | norm | 1 | > | + | norm | 1 | > | ++ | norm |
| | 2 | > | ++ | norm | 2 | >> | ++ | norm | 2 | > | +++ | norm |
| | 3 | > | ++ | norm | 3 | >>> | +++ | norm | 3 | > | ++ | norm |
| MA vaccae post-treated | 1 | > | ++ | norm | 1 | >> | ++ | norm | 1 | >> | ++ | red |
| | 2 | > | +++ | norm | 2 | > | +++ | norm | 2 | >> | +++ | red |
| | 3 | > | ++ | norm | 3 | > | ++ | norm | 3 | >> | ++ | norm |
| Serum post-treated | 1 | > | ++ | norm | 1 | norm | +++ | norm | 1 | > | +++ | red |
| | 2 | > | + | norm | 2 | > | ++ | red | 2 | > | +++ | norm |
| | 3 | > | ++ | norm | 3 | > | +++ | norm | 3 | > | +++ | norm |

Key:
Spleen: the degree of enlargement was compared to the negative control mice (group 1):
(>) -moderate (1* bigger)
(>>) -much (2* bigger)
(>>>) -extreme (3* bigger)
Lungs: lesions started with grey spots. The next stage is characterised by the formation of white nodules around the grey spots. The different stages are indicated by "+", "++" and "+++" or "normal " if no lesions were visible.
Liver: colour of liver was noted "normal" if light brown, or "red".
MA tb - mycolic acids originating from *M. tuberculosis*
MA vaccae - mycolic acids originating from *M. vaccae*

1.3.4.4 The Influence of Pre-treatment and Post-treatment of the Experimental Mice with Resaponified Mycolic Acids Originating from *M. tuberculosis* on Cytokine Profiles in the Lungs Lungs used in the cytokine determinations were removed from mice five weeks after the infection with *M. tuberculosis*.

1.3.4.4.1 Pre-treatment with Mycolic Acids and Its Effect on IL-12 in the Lungs

Interleukin 12 was determined in the lungs because:
 i) IL-12 is mainly expressed by macrophages, which are abundant in the lungs;
 ii) it is known to play a role as a pro-inflammatory cytokine in protection against tuberculosis;
 iii) its expression in mice has been found to be enhanced by the introduction of mycolic acids (see section 1.3.4.1).

Figure 14:
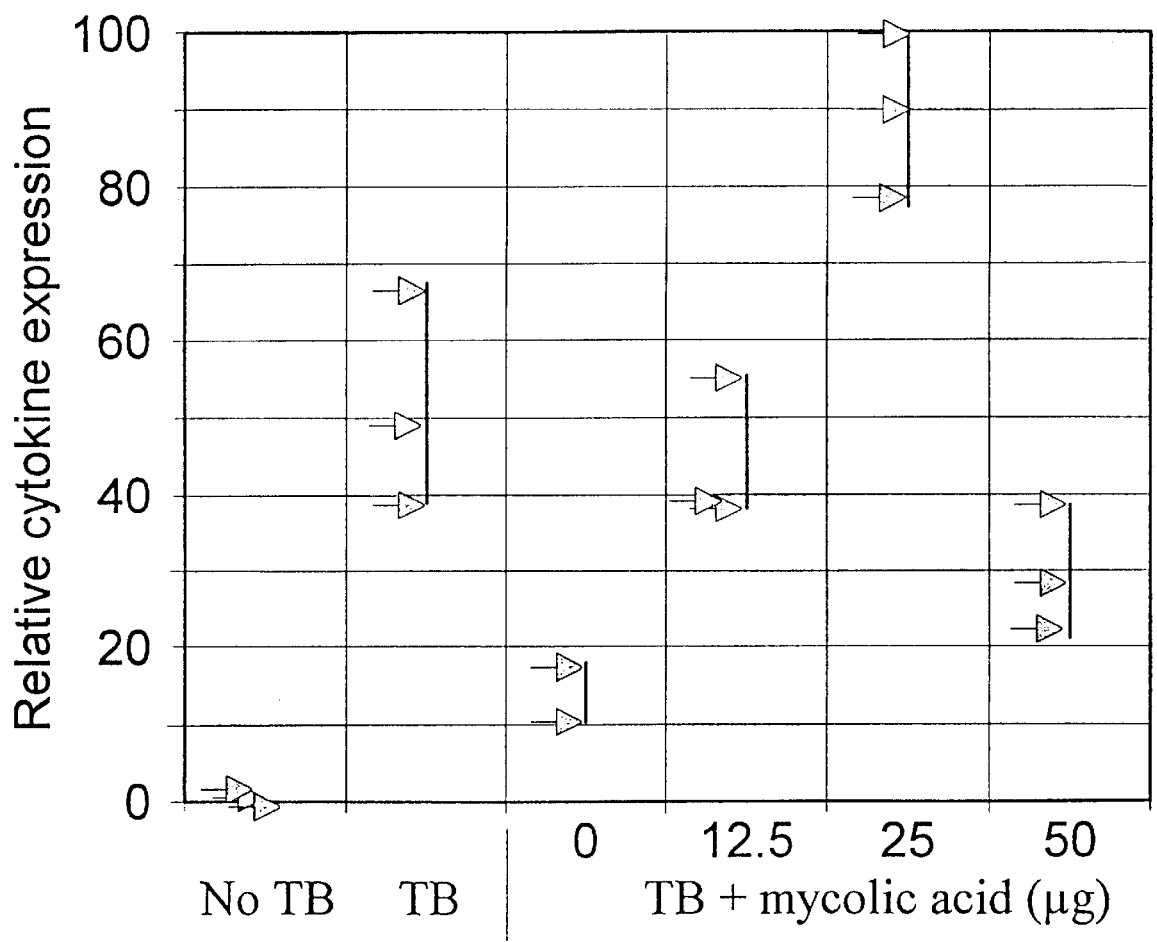
FIG. 14 shows the expression of IL-12 in *M. tuberculosis*-infected Balb/c mice, pre-treated with mycolic acids (from *M. tuberculosis*) one week before the infection, at the indicated doses. Lungs were removed five weeks after the infection.
Figure 15:
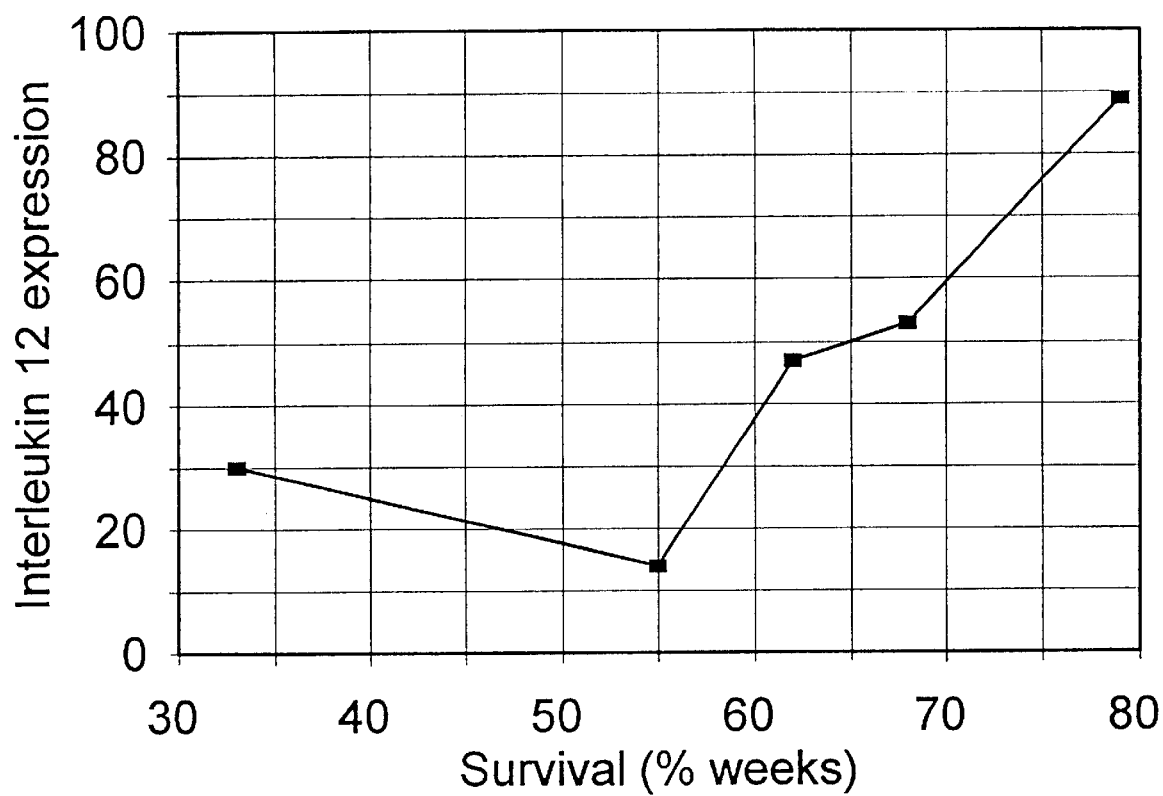
FIG. 15 shows the correlation between IL-12 expression in the lungs of Balb/c mice, pre-treated with mycolic acids (from *M. tuberculosis*), at five weeks after the infection and their survival.

Three doses of mycolic acids, i e., 12.5 μg, 25 μg and 50 μg were used in IR IV for pre-treatment. The results presented in FIG. 14 indicate that mycolic acids enhanced IL-12 expression in the lungs up to an optimum dose (25 μg), after which expression was suppressed. This correlated with the protection that was induced by mycolic acids pre-treatment (FIG. 15). Protection by mycolic acids as well as concomitantly enhanced expression of IL-12 was confirmed in IR V (Table 6).

1.3.4.4.2 Pretreatment with Mycolic Acids and Its Effect on IFN-γ in the Lungs

Interleukin 12 is known to exert some of its immunoregulatory properties through the stimulation of IFN-γ, which then provides protection against tuberculosis infection In order to determine whether this correlation held true for the protection provided by mycolic acids, the degree of expression of IFN-γ was determined in the lungs, five weeks after the infection with *M. tuberculosis*.

Figure 16:
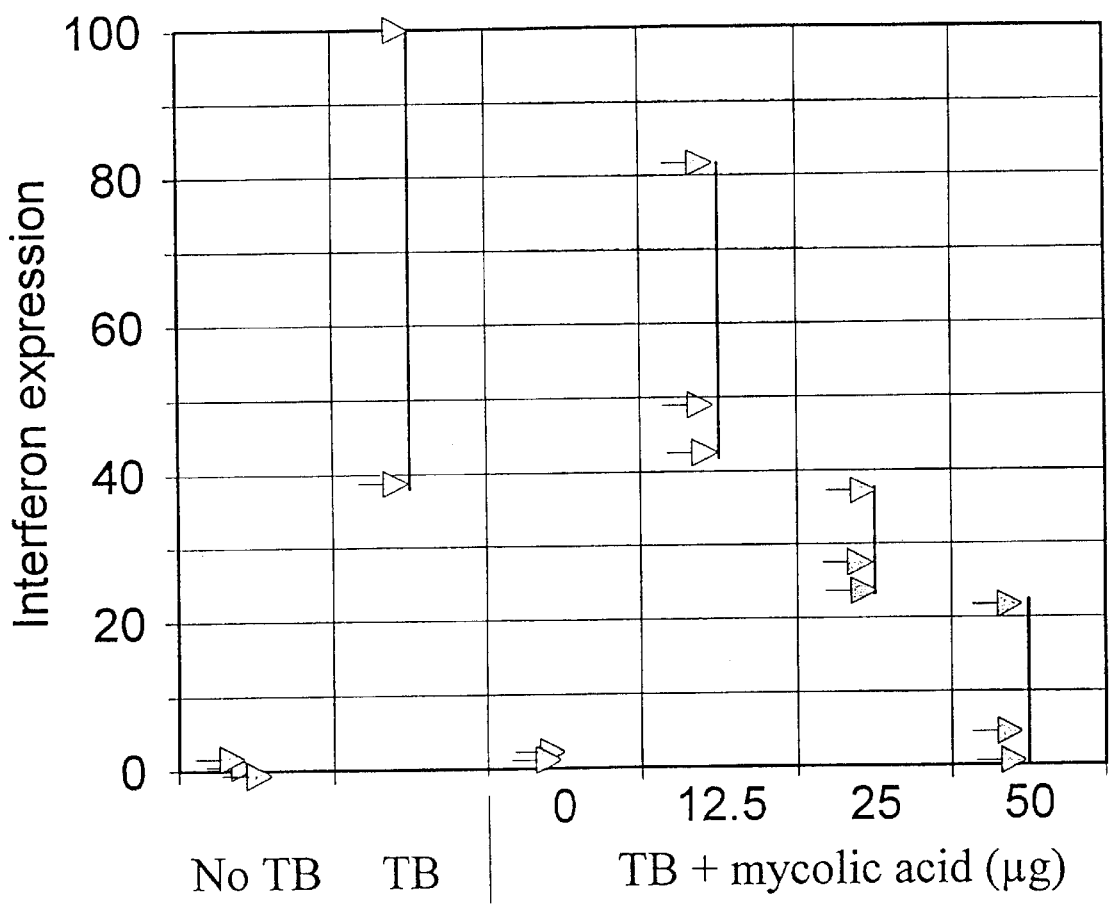
FIG. 16 shows the expression of IFN-γ in *M. tuberculosis*-infected Balb/c mice pre-treated with mycolic acids (from *M. tuberculosis*) one week before the infection, at the indicated doses. Lungs were removed five weeks after the infection.
Figure 17:
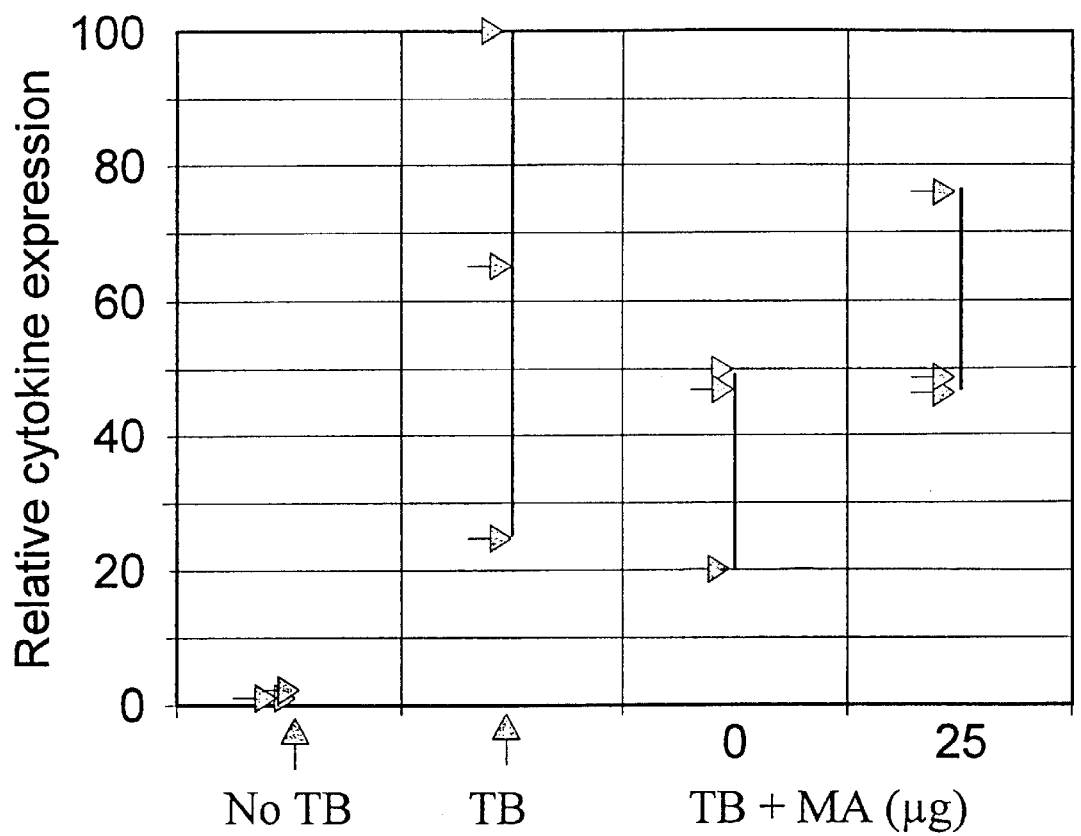
FIG. 17 is a repeat experiment and shows the expression of IFN-γ in *M. tuberculosis*-infected Balb/c mice pre-treated with mycolic acids (from *M. tuberculosis*) one week before the infection, at the indicated doses. Lungs were removed five weeks after the infection.

The results presented in FIG. 16 do not clearly support a model in which IFN-γ is the cytokine stimulated by IL-12 to exert a protective effect in animals against tuberculosis. This also applies to the measurements of TNF-α (results not shown). In a repeat experiment (IR V, as shown in FIG. 17) the results presented in FIG. 16 could not be confirmed for both IFN-γ and TNF-α.

It was concluded that the semi-quantitative PCR is not sufficiently reliable in providing quantitative data on subtle differences between IFN-γ and TFN-α expressions of mycolic acids in treated and untreated mice. However, it is adequate to show qualitatively that IFN-γ and TFN-α are expressed upon infection with *M. tuberculosis*. The data do not exclude the possibility that IFN-γ and possibly TNF-α may play effector roles in response to the increased IL-12 expression induced by mycolic acids.

1.3.4.4.3 Pre-treatment with Mycolic Acids and Its Effect on TGF-β in the Lungs

The correlation that was found between the protective effect of mycolic acids and its influence on IL-12 expression indicated that protection was brought about by a pro-inflammatory mechanism. The expression in response to pre-treatment with mycolic acids of two other pro-inflammatory cytokines, IFN-γ and TNF-α (results not shown), did not yield satisfactory quantitative results, but at least did not argue against a pro-inflammatory effect induced by mycolic acids. TGF-β is an anti-inflammatory cytokine expressed in macrophages which might respond to mycolic acids.

Figure 18:
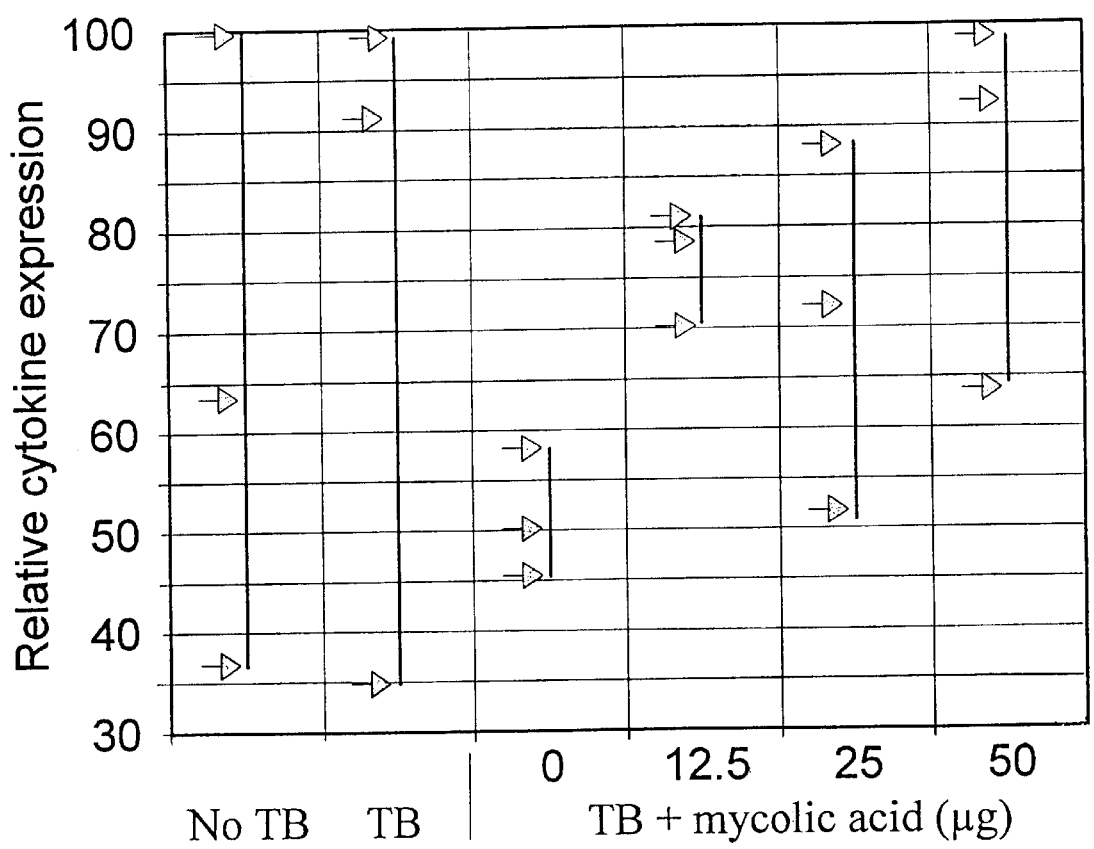
FIG. 18 shows the expression of TGF-β in *M. tuberculosis*-infected Balb/c mice pre-treated with mycolic acids (from *M. tuberculosis*) one week before the infection, at the indicated doses. Lungs were removed five weeks after the infection.

The results in FIG. 18 indicate that the levels of expression of the anti-inflammatory cytokine TGF-β were already high in the non-infected control mice. This is the only one of the four cytokines investigated that gave this result. It would not be unusual for an anti-inflammatory cytokine in the lungs to maintain a high level of expression under normal conditions when the inflammatory response could do harm to normal, uninfected lung tissue. After the infection with *M. tuberculosis*, the levels of TGF-β expression were not significantly altered, although a broad spread of measured values was obtained, indicating the possibility of unstable mRNA structure. Introduction of homologous serum into the animals significantly lowered the expression of TGF-β, while there was a tendency to restore this level by addition of mycolic acids adsorbed onto the serum. Due to the spread of the measurements for every point of data, a definite conclusion based on a fine resolution between experimental groups of animals could not be made.

Figure 19:
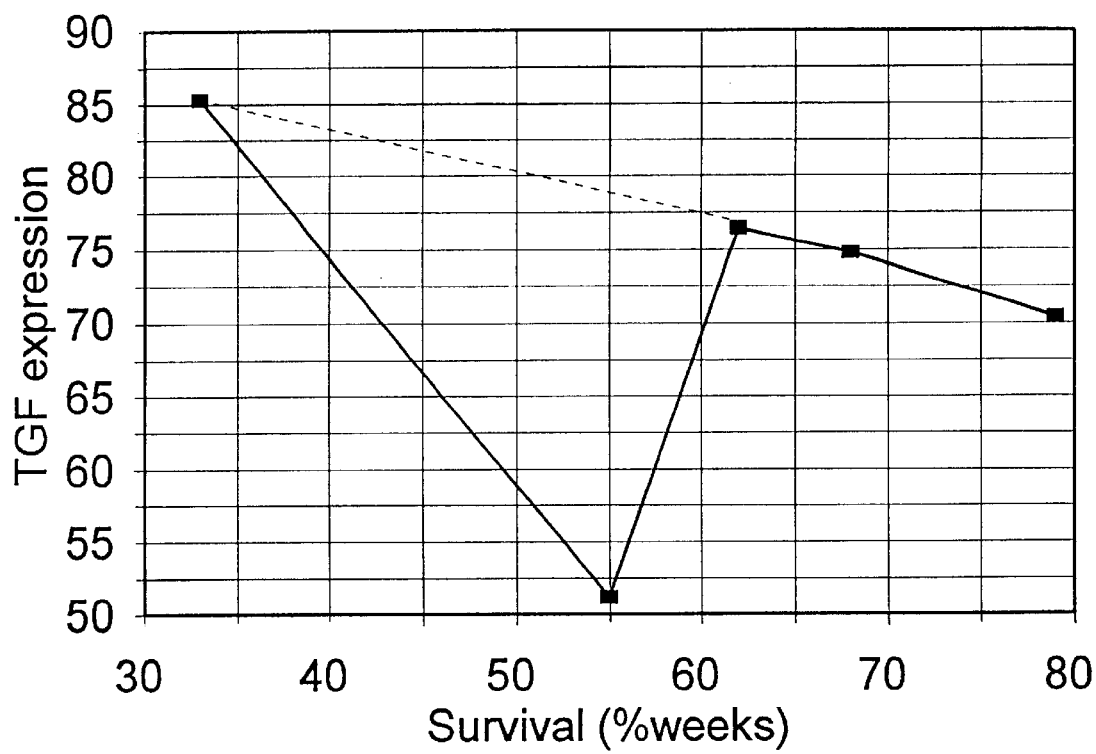
FIG. 19 shows the correlation between TGF-β expression in the lungs of Balb/c mice, pre-treated with mycolic acids (from *M. tuberculosis*) and their survival. The lungs were removed five weeks after the infection.

These measurements of expression of TGF-β illustrate the complicating role that homologous serum played in defining the immunoregulatory role of mycolic acids. Ignoring the effect of the serum carrier, the data might have suggested a reduced expression of TGF-β under the influence of mycolic acids, as FIG. 19 illustrates.

Figure 20:
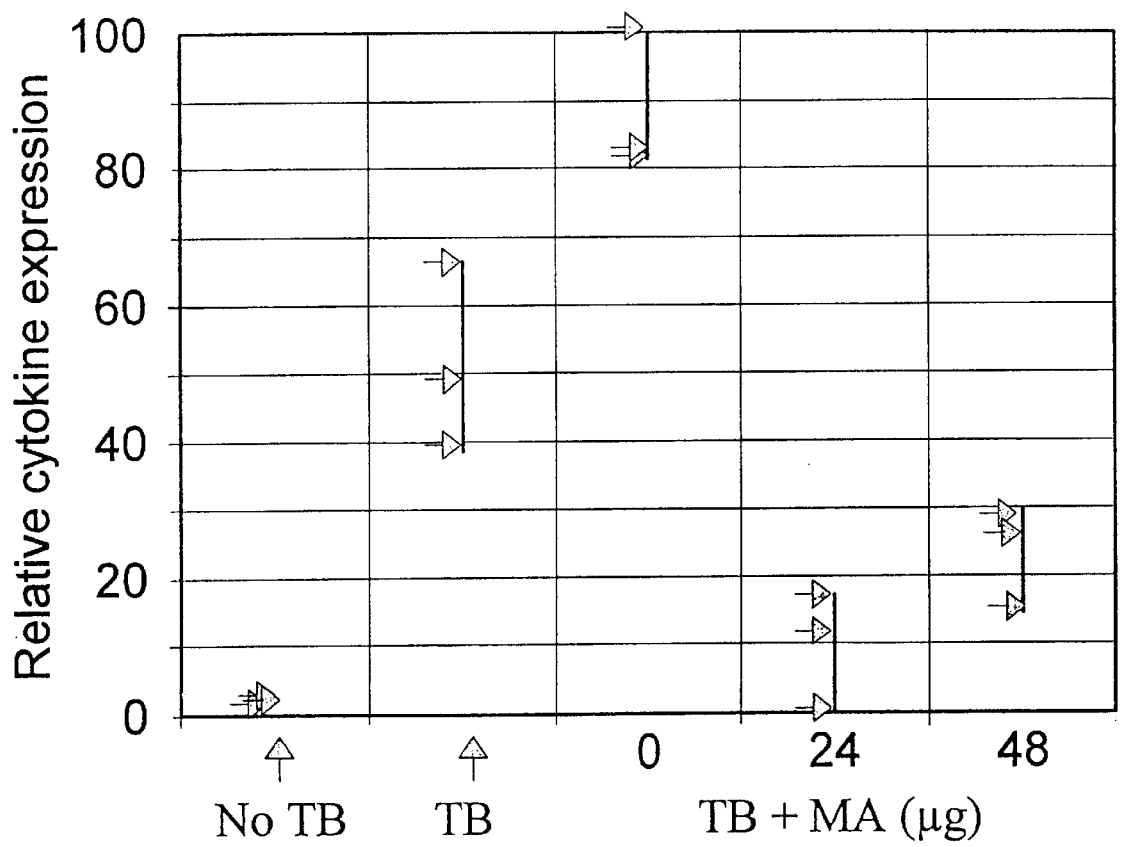
FIG. 20 shows the expression of IL-12 in *M. tuberculosis*-infected Balb/c mice, post-treated with mycolic acids (from *M. tuberculosis*) three weeks after the infection, at the indicated doses. Lungs were removed five weeks after the infection.
Figure 21:
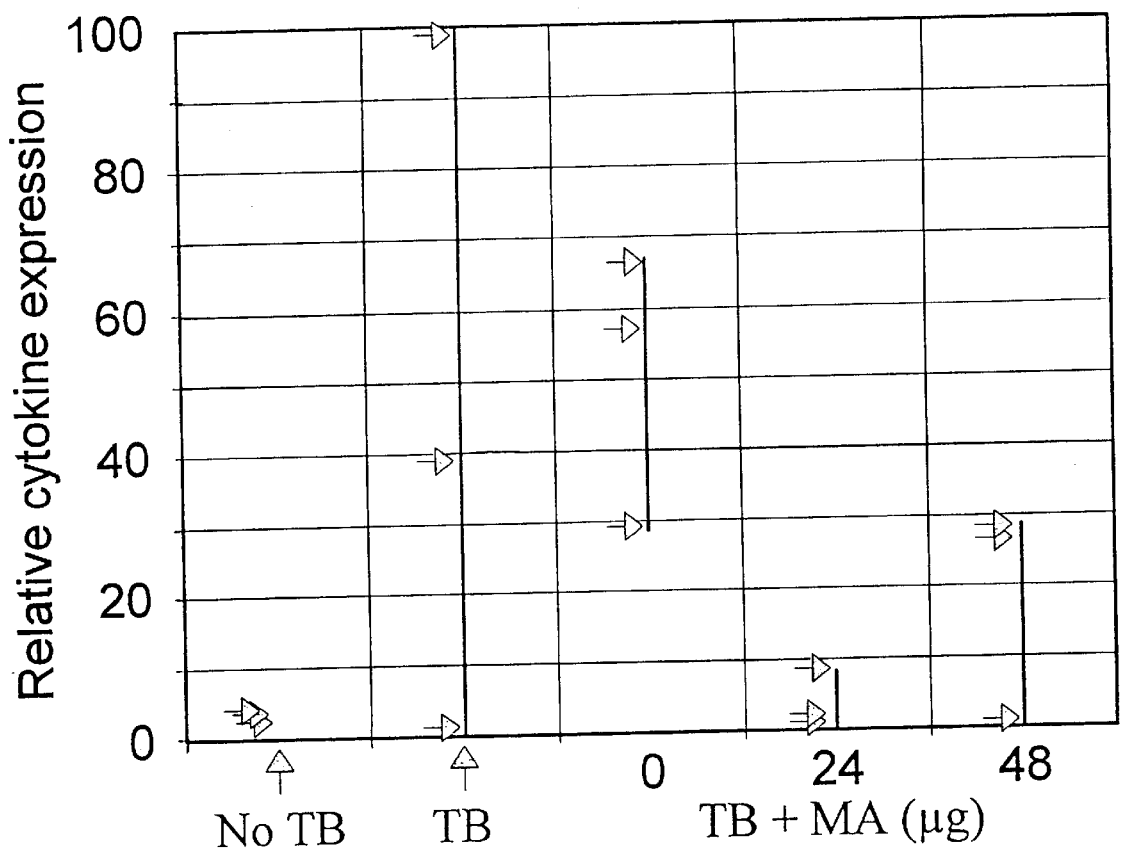
FIG. 21 shows the expression of IFN-γ in *M. tuberculosis*-infected Balb/c mice post-treated with mycolic acids (from *M. tuberculosis*) three weeks after the infection, at the indicated doses. Lungs were removed five weeks after the infection.
Figure 22:
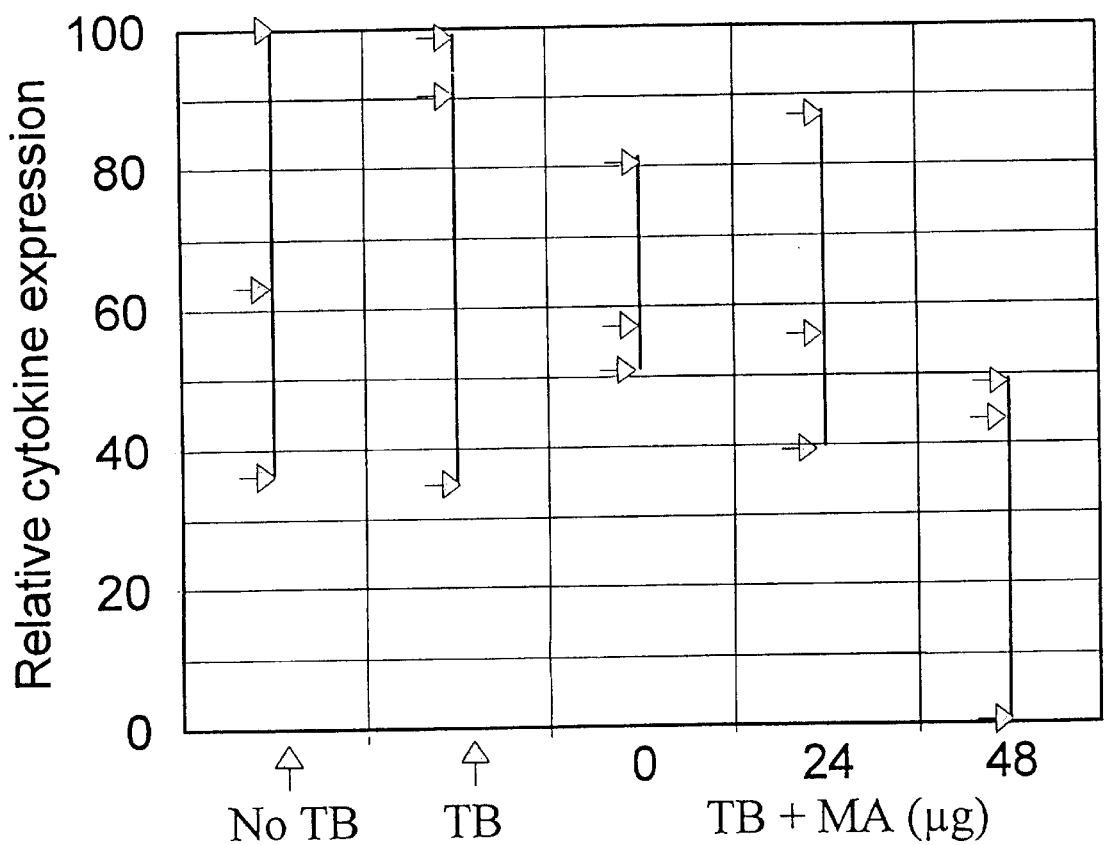
FIG. 22 shows the expression of TGF-β in *M. tuberculosis*-infected Balb/c mice post-treated with mycolic acids (from *M. tuberculosis*) three weeks after the infection, at the indicated doses. Lungs were removed five weeks after the infection.
Figure 23:
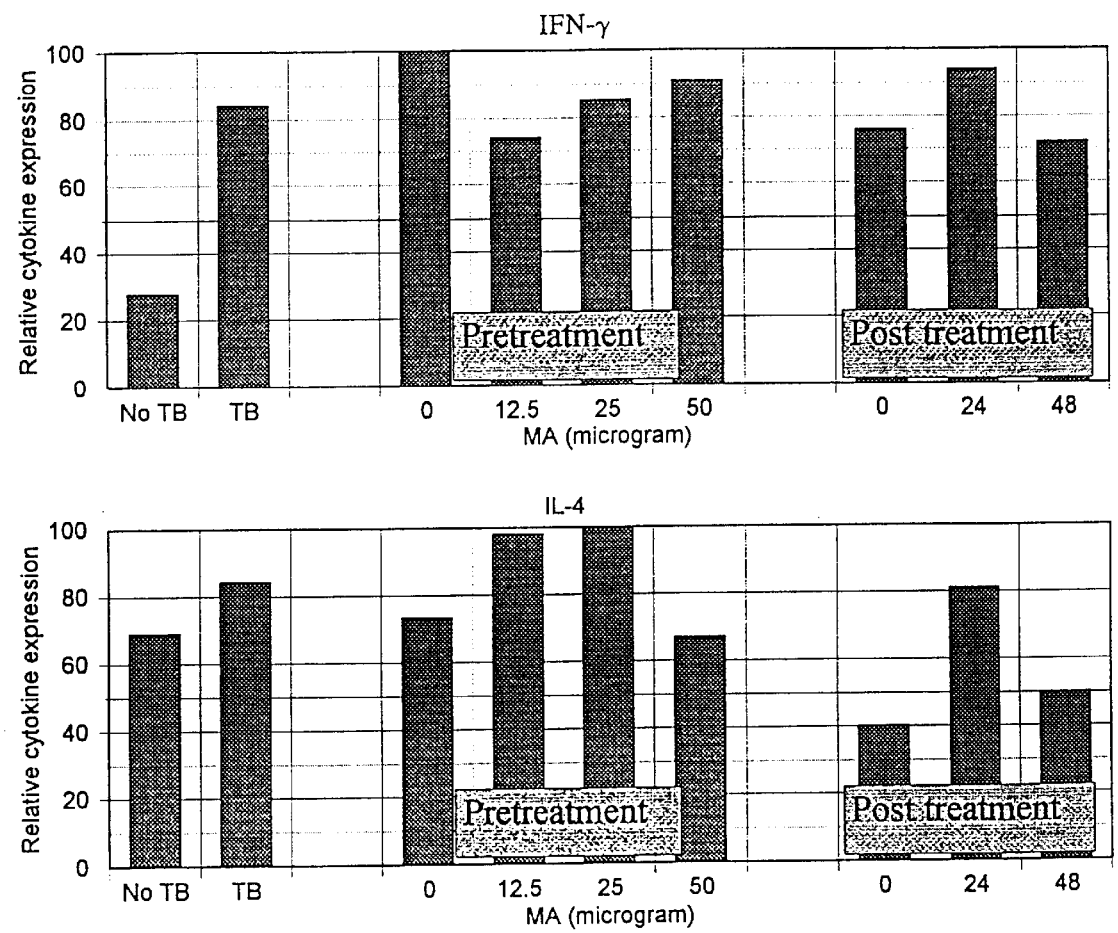
FIG. 23 shows cytokine profiles of IFN-γ and IL4 in the spleen of Balb/c mice pre- and post-treated with mycolic acids (from *M. tuberculosis*) at the indicated doses.
Figure 24:
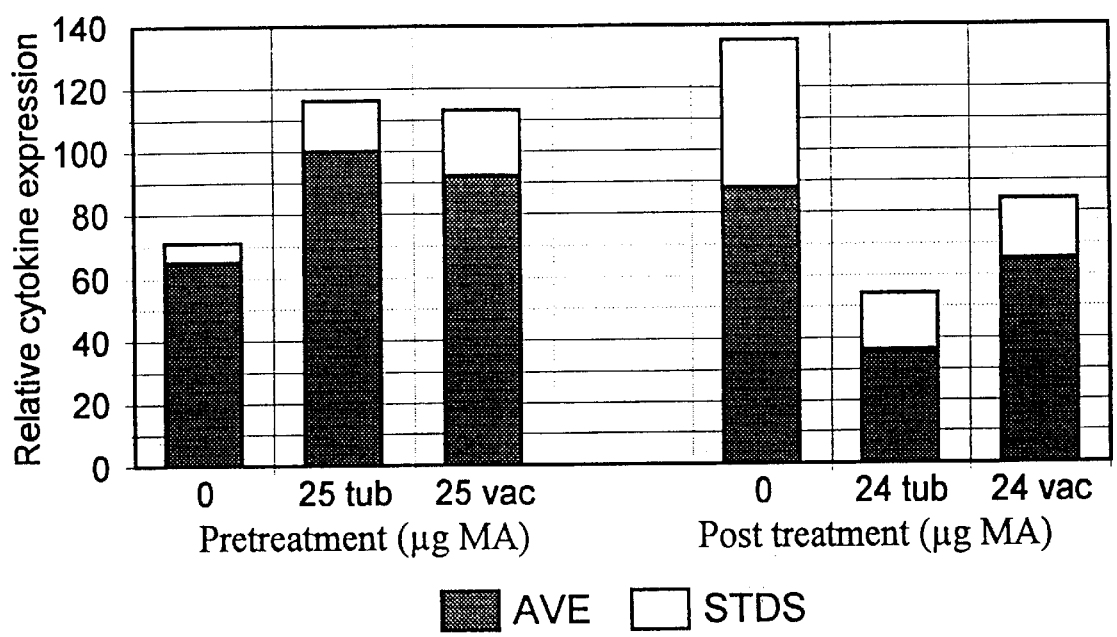
FIG. 24 shows the expression of IL-12 in the lungs of *M. tuberculosis*-infected Balb/c mice, pre- and post-treated with mycolic acids (from *M. vaccae*) at the indicated doses. Lungs were removed five weeks after the infection.

1.3.4.4.4 Post-infection Treatment with Mycolic Acids and Its Effect on IL-12, IFN-γ and TGF-β in the Lungs Balb/c mice infected with *M. tuberculosis* and treated with mycolic acids three weeks after the infection, showed protection against tuberculosis (FIG. 12). This was also observed in C57B1/6 mice (FIG. 13). The measured values for expression of IL-12 in the lungs of Balb/c mice post-treated with mycolic acids (FIG. 20) do not support a model in which this cytokine mediates the protection, as was found in pre-treatment. Although the IFN-γ expression levels correlated positively with IL-12 expression levis (FIG. 21), they did not correlate with increased survival. FIG. 22 indicates a decreased TGF-β expression in the lungs of Balb/c mice that were treated with 48 μg of mycolic acids after the infection with *M. tuberculosis*. This decreased TGF-β expression correlated with an increased survival.

These observations indicate a different model of protection provided by mycolic aids as a potential therapeutic agent against infection with *M. tuberculosis,* i.e., the down-regulation of the anti-inflammatory process in the lungs.

1.3.4.5 The Influence of Pre-treatment and Post-treatment of the Experimental Mice with Resaponified Mycolic Acids Originating from *M. tuberculosis* on Cytokine Profiles in the Spleens Spleens used in the cytokine determinations were removed from mice five weeks after the infection with *M. tuberculosis.*

The Th1 response has been previously indicated as the protective mode of Th cells to provide protection against tuberculosis. Because infection with *M. tuberculosis* was, in our experiments, routed systemically through the tail vein, the spleen was regarded as a prime lymphoid organ from which the Th1/Th2 bias could be determined, using IFN-γ as the indicator for a Th1 and 'IL-4 as the indicator for a Th2 response. These cytokines would have acted antagonistically, if the spleen became biased in one of the two modes upon immune challenge by *M. tuberculosis*. However, from the results presented in FIG. 23 it is evident that the infection with *M. tuberculosis* induced the expression of both cytokines and neither the expression of IFN-γ nor of IL-4 was significantly altered by the pre-treatment or post-treatment with mycolic acids.

These results suggest that:

i) the spleen does not appear to be the organ where the role of mycolic acids as a protector against tuberculosis is decided;

ii) the T cells do not appear to play the decisive role in providing protection against tuberculosis upon the administration of mycolic acids.

1.3.4.6 The Influence of Pre-treatment and Post-treatment of the Experimental Mice with Resaponified Mycolic Acids Originating from *M. vaccae* After the Infection with *M. tuberculosis*

The immunoregulatory effects of mycolic acids were found to be present irrespective of the source species of Mycobacterium from which they were obtained. Mycolic acids extracted from *M. vaccae*, after the countercurrent purification, stimulated the expression of interleukin 12 in Balb/c mice (FIG. 24) and induced protection against tuberculosis in the lungs of the experimental animals (Table 6). These results confirm the effects observed in the mice pre- and post-treated with mycolic acids originating from *M. tuberculosis*, described in sections 1.3.4.3 and 1.3.4.5.

1.3.5 Assessment of the Significance of the Results

The results obtained in the above experiments indicate that mycolic acids can protect mice against infection with *M. tuberculosis,* particularly when administered before the infection/onset of the disease. The kidneys, liver and lungs in mice were found to respond to mycolic acids even without the infection with *M. tuberculosis* (FIG. 8).

It should be stressed that the lungs from the mycolic acids-pre-treated animals were the only organ in which a significantly reduced tubercle formation could be observed upon macroscopic post-mortem assessment (Table 6) and were also the only organ that responded differently to the infection with *M. tuberculosis* in respect of IL-12 expression. It was, therefore concluded, that the protection provided by mycolic acids manifested itself mainly in the lungs. Preliminary evidence from IR V indicated that mycolic acids from other species of Mycobacterium (e.g. *M. vaccae*) could also induce immune effects in the lungs of mice infected with tuberculosis (FIG. 24).

The cytokine profiling of the lungs and spleen five weeks after the infection with *M. tuberculosis*, with or without pre- or post-treatment with mycolic acids, confirmed the observation that the lungs were the responsive organs to the antigenic challenge with mycolic acids. Although cytokine expression in the spleen was induced upon the infection with *M. tuberculosis*, it was not significantly altered by the pre- or post-treatment with mycolic acids. No bias towards either Th1 or Th2 mode of immune response was evident from the measurements of the IFN-γ and IL-4 expression levels in mice infected with tuberculosis, treated or untreated with mycolic acids (FIG. 23).

The results of IL-12, IFN-γ and TGF-β measurements in the lungs of the experimental animal support the view that a pro-inflammatory mechanism of protection against tuberculosis was elicited by pretreatment with mycolic acids. Interleukin 12 expression correlated positively with the survival of the *M. tuberculosis*-infected mice, while IFN-γ (although induced) and TNF-α, could not be determined with sufficient accuracy to clearly demonstrate its role in the protection. The TGF-β levels in the organs of the experimental animals remained largely unaltered.

During the post-infection treatment with mycolic acids, the levels of expression of IL-12 positively correlated with those of IFN-γ. No correlation with the protection against tuberculosis by mycolic acids was observed. Rather, a down-regulation of TGF-β appeared to be a possible mechanism of protective inflammation in the lungs. This mechanism might explain the lower efficiency of the post-infection therapy with mycolic acids.

Overall, the mechanistic model of mycolic acids-induced protection against tuberculosis, supported by the experimental evidence provided above, allows for the prediction of a much enhanced protection offered by mycolic acids against the disease, when the infection with *M. tuberculosis* occurs by the normal route, i.e., by inhalation into the lungs. It appears possible that the administration of mycolic acids directly into the lungs of tuberculosis-infected individuals, via inhaled vapours generated by a nebuliser could greatly reduce the incidence of infection with *M. tuberculosis* and also aid towards recovery from the disease.

The above findings can be extrapolated to human beings, and it can be expected that the response in humans towards the treatment with mycolic acids should be better. This assumption is based on the fact that humans possess mycolic acids presenting molecules, CD1b, expressed on their antigen presenting cells, the homologue of which has not yet been identified in mice.

Positive evidence was found for short term prevention or therapy of tuberculosis by mycolic acids in rats and mice. The results obtained would suggest that Th cells did not participate in the immune response upon challenge with mycolic acids either before or after the infection with *M. tuberculosis*. However, as humans possess CD1b molecules mycolic acids may have a role in human vaccines, i.e., for using them to provide long term immune memory against infection with *M. tuberculosis*.

The experimental evidence supports a role of cells of innate immunity, such as macrophages and natural killer cells, in responding towards mycolic acids administration in a manner that decreases the pathogenic effects induced in the lungs by *M. tuberculosis*.

EXAMPLE 1a

Protection Against Tuberculosis in Mice Provided by the Administration of Purified Mycolic Acids. Experiments Involving Animals Infected with *M. tuberculosis* by Intra-nasal Administration 1a.1 Rationale Dissemination of *M. tuberculosis* occurs in nature by inhalation of airborne droplets containing a few bacilli, expectorated by infected individuals wit "open" pulmonary disease i.e., by smear-positive patients. Such patients have very high numbers of bacilli in their sputum (at least 5 000 bacilli/ml) which are visible on standard microscopical examination. As the lungs are the most frequent portal of entry, they are the most frequently affected organ in man, although virtually any organ or system of the body may be invaded by *M. tuberculosis*.

In order to imitate the natural way of entry of mycobacteria into the experimental animals, an additional experiment was carried out in which the animals were infected by the intra-nasal administration of mycobacteria, while the route of administration of mycobacterial mycolic acids remained intravenous.

The results obtained from the treatment of mice with mycolic acids in the absence of *M. tuberculosis* infection (Example 1), indicated the lungs as the site of mycolic acids-induced IL-12 expression. This suggested that mycolic acids could be especially effective as prophylactant if tuberculosis infection was given through the intra-nasal route, targeting the lungs directly.

The survival of mycolic acids pre-treated mice Balb/c, infected with *M. tuberculosis* either intravenously or intranasally, was therefore tested.

1a.2 Materials

The materials used in the Example 1a, i.e. the bacterial culture, media, reagents, the experimental animals and plasticware were identical to those described in Example 1.

Methods

The methods used in the experimental work carried out to perform Example1a i.e., the cultivation of *M. tuberculosis*, viable and total bacterial counts, the preparation, extraction, purification and analysis of mycolic acids, the preparation of mycolic acids-mouse serum conjugates, the preparation of bacterial suspensions for the induction of tuberculosis in mice as well as the methods used in handling experimental animals and the conditions of their maintenance, were identical to the corresponding methods described in Example 1.

However, the manner in which the suspensions of *M. tuberculosis* cells were introduced into Balb/c mice was different and is described in detail below.

1a.2.1 Introduction of the *M. tuberculosis* H37 Rv Suspensions

The cells of *M. tuberculosis* H37 Rv, harvested from LJ slants, were suspended in the diluting buffer (0.01% v/v Tween 80 in 0.9% m/v NaCl) and homogenized. After centrifugation in a Beckman J-6 centrifuge for 20 min at 1 580 g, the cells were washed with a sterile solution of 0.9% m/v of NaCl and adjusted to a concentration corresponding to a McFarland standard No.4. After the confirmation of the total direct bacterial count, carried out on an autoclaved suspension in a Neubauer counting chamber, the suspension was further diluted in the sterile solution of 0.9% NaCl to obtain concentrations of *M. tuberculosis* corresponding to $10^3$, $10^4$ and $10^5$ cells/ml.

The viable counts of the mycobacteria in the suspensions were confirmed by plating 100 μl aliquots of the relevant dilutions onto Middlebrook 7H-10 agar medium, incubating the plates at 37° C. for two weeks and counting the number of colony forming units (CFU).

The introduction of the *M. tuberculosis*'s suspensions was performed in a biosafety cabinet class III in the PIII facilities at the Tuberculosis Institute of Medical Research Council in Pretoria.

In the intra-nasally infected group of mice, the bacterial suspensions prepared in sterile saline were introduced into the nostrils of mice anaesthetized with 5% diethylether, in aliquots of 60 μl per animal. The suspensions were released drop-wise into the nostrils using autoclaved pipette tips, while the animals were in dorsal recumbence. The intravenous administration of mycobacteria was performed as described in Example 1.

Control animals received and equivalent volume sterile saline, i.e., 60 μl introduced intra-nasally or 100 μl administered intravenously.

The administration of the mycolic acids conjugates was carried out for both types of the infection with *M. tuberculosis* via the intravenous route, after mice were heated for 5 min in a heating box to effect vasodilation of the tail veins. The mycolic acids-mouse serum 100 μl mouse serum per mouse.

Controls animals received 100 μl of mouse serum introduced in the same manner.

Balb/c mice were divided into nine groups and treated as indicated in Table 6a

TABLE 6a

Experimental set-up for immunoregulatory experiment No 1a

| Group No | Group No/ treatment | Number of mice per group |
|---|---|---|
| 1 | 1. Serum Saline | 10 |
| 2 | 2. Serum M tb[1] intra-nasally | 15 |
| 3 | 3. 5 μg MA iv[2] M tb intra-nasally | 15 |
| 4 | 4. 25 μg MA iv M tb intra-nasally | 15 |

TABLE 6a-continued

Experimental set-up for immunoregulatory experiment No 1a

| Group No | Group No/ treatment | Number of mice per group |
|---|---|---|
| 5 | 5. 25 μg MA iv Saline iv | 15 |
| 6 | 6. Serum iv M tb iv | |
| 7 | 7. 5 μg MA iv M tb iv | 10 |
| 8 | 8. 25 μg MA iv M tb iv | 10 |
| 9 | 9. Control No treatment | 15 |

[1])M. tb - *M. tuberculosis*
[2])iv - intravenous administration 1a.3 Results

All the mice in the intravenously infected pre-treatment and control groups were dead by week 36, with a very small difference in the average survival time (Table 6b). This corroborates the previous results (Example 1) where an increase in time of survival was seen in the mycolic acids-pre-treated group, but all the mice eventually died.

In contrast, 8 out of 9 mice (which corresponds to a 89% survival) of the intra-nasally infected mice pre-treated with mycolic acids-serum conjugate survived for more than 36 weeks, compared to the control mice where only 4 mice survived, which constituted 44% survival (Table 6b). After 36 weeks, the intra-nasally infected, mycolic acids pre-treated mice appeared to have the tuberculosis infection under control, while the control animals that were not pre-treated with mycolic acids were either dead, or sick at the end of week 36.

A single mouse in the mycolic acids pre-treatment group died, but the cause of death could not be established, because it was eaten by other mice in the cage. The remaining mice in the mycolic acids pre-treated group appeared healthy at week 36. The subsequent culturing of the spleens and lungs of the surviving animals confirmed the presence of *M. tuberculosis* infection in both organs in all the mice, including those of the mycolic acids pre-treated group.

TABLE 6b

The survival of Balb/c mice pre-treated with 25 μg mycolic acids: intra-nasal versus intravenous route of infection with *M. tuberculosis*. Observation carried out over a period of 36 weeks.

| | Intravenous infection with 4 × 10$^4$ cfu | | Intra-nasal infection with 1 × 10$^5$ cfu | |
|---|---|---|---|---|
| Type of treatment | MA -pre-treated mice | Control mice | MA -pre-treated mice | Control mice |
| Average survival time (in weeks) | 25.56 | 24.48 | 35.64 | 31.3 |
| Number of mice surviving | 0/7 0% | 0/7 0% | 8/9 88% | 4/9 44% |

MA - mycolic acids
cfu - colony forming units 1a.4 Discussion

The normal route of infection with *M. tuberculosis* is by inhalation into the lungs. While mycolic acids induced the protective IL-12 and IFN-τ cytokines mainly in the lungs, it was predicted that the protection provided by mycolic acids as prophylactant against tuberculosis would be much more pronounce when *M. tuberculosis* infection was given by the intra-nasal, rather than the intravenous route. This was confirmed (Example 1a), showing that mycolic acids administration could sufficiently stimulate the immune system of the experimental animals to enable them to bring the infection with *M. tuberculosis* under control, although it was unable to prevent the infection from establishing itself in the lungs and spleen.

EXAMPLE 2

Protection Against Tuberculosis-induced Arthritis in Rats

2. Materials 2.1 Culture

*Mycobacterium tuberculosis* H37Rv ATCC 27294—a virulent strain, originally isolated from all infected human lung, was used in the experiments.

The culture was purchased in lyophilized form from the American Type Culture Collection (ATCC), Maryland, USA.

*M. tuberculosis* H37Ra ATCC 27294—an avirulent strain, was purchased in lyophilized form from Difco (Cat No: 3114-33-8).

2.1.2 Media 2.1.2.1 Growth Media

The following media were used for the cultivation of *M. tuberculosis*:

Löwenstein-Jensen (LJ) medium (slants) and Middlebrook 7H10 agar (plates).

A detailed composition of the ingredients necessary for the preparation of these media as well as the conditions recommended for their sterilization, are given in the Laboratory Manual of Tuberculosis Methods, Tuberculosis Research Institute of the SA Medical Research Council (1980, Chapter 6, pp 83–105; Second Edition, revised by E E Nel, H H Kleeberg and E M S Gatner).

The media were prepared by the National Tuberculosis Institute of the Medical Research Council of South Africa, in Pretoria.

2.1.2.2 Media Used for Washing and Diluting of Mycobacteria

The harvested bacteria were washed in sterile 0.9% m/v NaCl (Saarchem, Chemically Pure, RSA).

Medium used for the preparation of serial dilutions preceding the determination of viable counts of *M. tuberculosis* was prepared by dissolving Tween 80 (Merck, Chemically Pure) in 0.9% m/v NaCl (Saarchem, Chemically Pure) to a concentration of 0.01% v/v and distributing it in 9.0 ml aliquots into test-tubes. The autoclaved media were stored at 4° C.

2.1.3 Reagents 2.1.3.1

For the preparation of the reagents used for the extraction, derivatization and High-Performance Liquid Chromatography (HPLC) analysis of mycolic acids, HPLC Grade methanol (BDH) and double-distilled deionized water were used.

Reagent A:25% potassium hydroxide (Saarchem, Analytical Grade) dissolved in methanol-water (1:1), i.e., 62.5 g potassium hydroxide was dissolved in 125 ml water and 125 ml methanol (BDH, HPLC Grade) was added.

Reagent B:Concentrated hydrochloric acid (Saarchem, Analytical Grade) diluted 1:1 with water.

Reagent C:2% potassium bicarbonate (BDH, Analytical Grade) dissolved in methanol-water (1:1), 10 g potassium bicarbonate was dissolved in 250 ml water and 250 ml methanol was added.

Reagent D:para-bromophenacylbromide dissolved in acetonitrile and crown ether (Pierce Chemical Co, Cat.

No 48891) was dispensed in 500 µl quantities into small amber-coloured screw cap vials with Teflon-coated septa. The caps were tightened and the vials were wrapped with Parafilm. Reagent D was stored at 4° C.

Reagent E:Reagent E was prepared by mixing reagent B 1:1 with methanol.

HPLC Standard: High Molecular Weight Internal Standard (C-100) from Ribi ImmunoChem Research Company, Cat No R-50. The standard, 1 mg, was dissolved in 20 ml chloroform (BDH, HPLC Grade) at 4° C. and aliquots of 100 µl were dispensed into 4 ml amber WISP vials, dried, capped with Teflon-coated septa and stored at 4° C.

Chloroform (Saarchem, Analytical Grade, RSA)

Methylene chloride (BDH, UK, HPLC-Grade)

Reagents A, B, C and E were prepared fresh prior to experiments, taking all the necessary safety precautions.

2.1.3.2 The following reagents were used for the preliminary purification of crude bacterial extracts ("fuel extraction") and for the countercurrent purification of the extracted mycolic acids:

Chloroform (Saarchem, Chemically Pure)

Methanol (Saarchem, Chemically Pure)

Acetone (Saarchem, Chemically Pure)

Sodium chloride (Saarchem, Analytical Grade)

Double-distilled deionized water was used for the preparation of the required reagent concentrations. i.e.:
39% v/v methanol
42% v/v chloroform
0.2 M NaCl 2.1.3.3 Reagents Used for the Induction of Adjuvant Arthritis:

Heat-killed and freeze-dried cells of *M. tuberculosis* H37Ra (Difco, Cat No 3114-33-8), 100 mg, suspended in 10 ml of Freund's Incomplete Adjuvant (FIA, Difco Cat No 0639) were used for the induction of adjuvant arthritis in Lewis rats.

2.1.3.4 Reagents Used for the Prevention of Adjuvant Arthritis

Freshly saponified mycolic acids (MA) originating from *M. tuberculosis* H37Rv were suspended in FIA (10 mg/ml FIA) and diluted with FIA to required concentrations, i.e.:
0.1 mg MA/100 µl, 0.3 mg MA/100 µl and 1.0 mg MA/100 µl.

2.1.3.5 Reagents Used in Monitoring the Production of Anti-mycolic Acids Antibodies:

Glycerol (Merck, Analytical Grade) was used for diluting sera of the experimental animals.

ELISA reagents:

Basic buffer—PBS buffer: 8.0 g NaCl, 0.2 g KCl, 0.2 g $KH_2PO_4$ and 1.05 g $Na_2HPO_4$ per 1 l distilled water, adjusted to pH 7.4.

Diluting buffer: 0.5% (m/v) casein in PBS buffer adjusted to pH 7.4 was used for diluting of the experimental animals' sera (mixed with glycerol 1:1) and for the preparation of suitable dilutions of immunoreagents.

Blocking buffer: 0.5% (m/v) casein in PBS buffer adjusted to pH 7.4 was used for blocking of ELISA plates.

Washing buffer: 0.5% (m/v) casein in PBS buffer adjusted to pH 7.4 was used for washing of ELISA plates.

Coating antigen: unsaponified mycolic acids originating from *M. tuberculosis* H37Rv, at a final concentration of 0.067 µg/µl. To prepare the coating antigen, 1 mg mycolic acids was dissolved in 100 µl chloroform and the solution introduced into 15.0 ml PBS buffer adjusted to pH 7.4. The solution was autoclaved at 121° C. for one hour.

Conjugates: Goat anti-rat antibody conjugated to peroxidase (H+L chains), Cappel (Cat No 55770). Rabbit anti-human gamma chain specific peroxidase conjugate (Sigma; A 8419).

Substrate: O-Phenylenediamine (Sigma; Cat No P-1526) and hydrogen peroxide (BDH).

Substrate buffer: 0.1 M citrate buffer (0.1 M citric acids and 0.1 M Tri sodium citrate), adjusted to pH 4.5.

2.1.4 Experimental Animals

Six weeks old, female Lewis rats were purchased from Shaw's farm, Blackthorn, Bicester, Oxon, England. This strain of rats is susceptible to the induction of arthritis.

The animals were maintained at the Animal Facilities of the Medical Research Council in Pretoria.

Feed and water

Mice cubes, manufactured by Epol, South Africa and tap, autoclaved water were provided ad libitum.

Sanitation:

Bronocide—manufactured by Essential Medicines (Pty) Ltd, was used for sanitation purposes.

2.1.5 Plasticware

The following plasticware was used:

Disposable Petri's dishes (Promex, RSA)

ELISA plates (Sterilin, UK)

Sterile, disposable 50 ml centrifuge tubes (Corning, USA)

Disposable tips (Elkay, Denmark)

96-well round bottom microplates (Nunc, Denmark)

2.2 Methods

The following methods were used in the experimental work:

2.2.1 Cultivation of the Bacterial Strains

The mycobacteria for the production of mycolic acids, i.e., *M. tuberculosis* H37Rv, were cultivated at 37° C. using Löwenstein-Jensen (LJ) medium slants and Middlebrook 7H-10 agar medium plates.

The sterility of all the media was confirmed, before they were used in the experiments by incubating them at 37° C. for 24 h.

For routine extraction of mycolic acids, approximately 4-week old cultures of *M. tuberculosis* grown on LJ slants or 2-week old cultures of *M. tuberculosis* grown on Middlebrook 7H-10 agar medium plates were used.

2.2.2 Viable and Total Bacterial Counts

For the viable count determination, serial dilutions of the harvested bacteria were suspended in the diluent medium (prepared as specified under 2.1.2.2) to a density corresponding to a McFarland standard 4 (approximately OD of 1.0; using a Beckman DU 65 spectrophotometer, at 486 nm). Tenfold serial dilutions were prepared using 9 ml aliquots of the diluent medium. From the last three dilutions corresponding to $10^{-3}$, $10^{-4}$ and $10^{-5}$ of the original suspension, aliquots of 0.1 ml (100 µl) were withdrawn and spread over the surface of Middlebrook 7H-10 plates. The plates were incubated at 37° C. and the developed colonies counted after two to three weeks for *M. tuberculosis* and after one week for the plates seeded with *M. vaccae*.

The direct total count was performed using a Neubauer counting chamber and the autoclaved cultures of *M. tuberculosis* and *M. vaccae*, originally adjusted to a density corresponding to a McFarland standard 4 and suitably diluted with the diluent medium.

Statistical analysis of the bacterial counts included the mean values of bacterial counts and standard deviations.

2.2.3 Preparation of Mycolic Acids from Bacterial Samples

The preparation of bacterial samples comprised three steps:
- harvesting of the Mycobacterial cells;
- saponification and
- extraction of mycolic acids.

Glassware used for the harvesting, extraction, derivatization and HPLC analyses of mycolic acids was washed in 2% (v/v) Contrad (Merck), rinsed in water, followed by rinsing in chloroform, water, technical Grade methanol, water and finally rinsed in double distilled deionized water. The washed glassware was dried in a warm air oven.

Harvesting was done by scraping the bacterial growth from the surface of media slants or agar medium plates (using sterile plastic loops) and by suspending them in Reagent A. Initial bacterial suspensions were prepared in Reagent A, by vortexing the harvested cells with sterile glass beads. Homogeneous bacterial suspensions were prepared using sterile tissue homogenizers. Prior to saponification, the density of the bacterial suspensions was adjusted to a density corresponding to a McFarland standard 4. This density of bacteria corresponds to approximately $10–12 \times 10^8$ colony forming units/ml.

The saponification, extraction and derivatization of mycolic acids were carried out as described by Butler, Jost and Kilburn (1991), with minor modifications and are described under the relevant headings.

Saponification of the Mycobacteria in Reagent A was carried out in an autoclave at 121° C., for 30 min.

2.2.4 Extraction of Mycolic Acids

The saponified samples were allowed to cool after autoclaving. Into 2 ml samples containing crude extract, 1.5 ml Reagent B was introduced. After vortexing, the pH of each sample was checked and if necessary, adjusted to pH 1 with Reagent B.

Subsequently, 2.0 ml chloroform was added to each sample and vortexed for 30 seconds. The layers were allowed to separate. The bottom layers were removed with Pasteur pipettes, transferred to amber WISP vials and evaporated to dryness at 85° C. in a heat block-evaporator under a stream of nitrogen. To neutralize traces of acid carried over, 100 $\mu$l of reagent C was added to each sample and the fluid evaporated to dryness at 85° C. in the heat block-evaporator under a stream of nitrogen.

2.2.5 Storage of the Crude Extracted Mycolic Acids

The material obtained from the large-scale extraction of mycolic acids originating from *M. tuberculosis* H37Rv, the crude bacterial extracts, was stored under acetone, at 4° C. in 4 ml amber WISP vials. To prevent evaporation/drying and the exposure to light, the caps of the WISP vials were covered with Parafilm.

2.2.6 Determination of Mycolic Acids Contents in Crude Extracts

Extracted mycolic acids were derivatized as follows:

To a cooled sample of crude extract (approximately 10 μg in 2.0 ml Reagent A), an aliquot of 1.0 ml chloroform was introduced, followed by the addition of 100 μl of Reagent D (derivatization reagent). The capped samples were vortexed for 30 seconds and heated for 20 minutes at 85° C. in a heat block-evaporator. Subsequently, the samples were cooled and 1.0 ml of Reagent E added. The samples were vortexed for 30 seconds and the layers allowed to separate. The bottom layers were removed with Pasteur pipettes and transferred to WISP-vials. The vials were placed in the heat block-evaporator and their contents evaporated to dryness at 85° C. using a stream of nitrogen.

The residues were resuspended in 0.212 g (which corresponds to 160 μl) methylene chloride, capped and vortexed Each reconstituted sample was introduced into a WISP vial containing 5 μg of the HPLC internal standard (prepared as described under 2.1.3.1), filtered through a 0.22 μm Millex GV4 filter with a polyethylene housing into another amber-coloured WISP-vial. The recapped vials were stored at 4° C. until ready for HPLC analysis.

2.2.7 HPLC Analysis and Quantification of Mycolic Acids

Repeatability and accuracy of the pipette used for the distribution of the HPLC standard was determined. The precision was established to be +/−1% 1% and it was confirmed prior to each aliquoting of the internal standard.

For the HPLC analysis 10 μl from each sample (maintained on ice during handling), was analyzed. Control samples, i.e., 10 μl of filtered methylene chloride, were run prior to each set of samples analyzed. If a large number of samples was analyzed, in order to validate the reliability of the HPLC apparatus, control samples were run after every three or four test samples.

The reverse-phase HPLC analyses were carried out using a Waters 600 E System Controller High Performance Liquid Chromatography apparatus consisting of:

Microsep M741 Data Module;

Waters 712 WISP Autosampler;

Detector (Waters 486 Tunable Absorbance Detector);

Column: Nova-Pak C18 4 μm 3.9×150 mm and an end connector set for steel cartridge columns.

RKC Rex-C 4 Column Temperature regulator.

Running conditions were:

Mobile phase:

Solvent A: HPLC Grade methanol

Solvent B: HPLC Grade methylene chloride

Flow Rate: 2.5 ml/min

Column temperature: 30° C.

The detector was set at 260 nm.

Prior to use, the solvents were sparged with Instrument Grade helium. High Purity Nitrogen was used to control hydraulics of the WISP vials autosampler.

The HPLC gradient initially comprised 98% (v/v) methanol (Solvent A) and 2% (v/v) methylene chloride (Solvent B). The gradient was increased linearly to 80% A and 20% B at one minute; 35% A and 65% B at ten minutes, held for 30 seconds and then decreased over 10 seconds back to 98% A and 2% B. This ratio was maintained for 4 minutes to allow for stabilization of the system prior to injection of the next sample.

Mathematical quantification of mycolic acids was carried out by comparing the combined peak areas of the tested samples to the peak area of the introduced quantity of the High Molecular Weight Internal HPLC Standard 2.2.8 Preliminary Purification of Crude Mycobacterial Extracts In order to shorten the time required for the countercurrent purification of the crude mycobacterial extracts, an additional preliminary extraction step was introduced This step had a dual purpose:

i) to remove unnecessary cellular components from the crude extract prior to the countercurrent purification and ii) to reduce soap fraction in the crude bacterial extracts.

A portion of the crude extracted material (approximately 3 to 4 g) was suspended in a minimum volume of the lower phase solvent (usually 100 ml), transferred into a separation funnel and mixed with an equal volume of the upper phase solvent The phases were allowed to separate and the upper phase was removed and stored at 4° C. Into the remaining lower phase an equal volume of the upper phase solvent was again introduced and the process of the phase separation was repeated.

The second upper phase was removed and stored at 4° C. and the second lower phase was dried in a Buchi Roto-evaporator RE 120, at 75° C. and its mass recorded.

2.2.9 Countercurrent Purification of Mycolic Acids Originating from *M. tuberculosis*

Countercurrent apparatus

A countercurrent apparatus produced by H O POST, Instrument Company Inc., Middle Village, N.Y. was used during the investigations. The "trains" in this model consisted of 2×250 inter-connected tubes.

Solvent system used in the countercurrent apparatus

The solvent system used for the countercurrent separation consisted of:

42% v/v chloroform (Saarchem, Chemically Pure Reagent)

39% v/v methanol (Saarchem, Chemically Pure)

19% V/V 0.2 M NaCl (Saarchem, Chemically Pure).

Double distilled deionized water was used for the preparation of the solvent system.

The components were mixed, equilibrated and the upper and lower phases were collected using a separation funnel.

The composition of the upper phase was established to be:
15% v/v chloroform, 52% v/v methanol and 33% v/v 0.2 M NaCl.

The composition of the lower phase was established to be:
68% v/v chloroform, 27% v/v methanol and 5% v/v 0.2 M NaCl.

The countercurrent purification process was carried out under the following conditions:

A countercurrent distribution train comprising 55 tubes, numbered 0–54, was used in the experiments. The upper phase solvent, a volume of 600 ml, was introduced into a buffer reservoir. A sample of 125 mg of mycolic acids after the preliminary purification was dissolved in 50 ml of the lower phase solvent, divided into five aliquots and introduced into first five tubes, numbered 0–4. Subsequently, 10 ml of the upper phase solvent was introduced into each of the first five countercurrent tubes. Into the remaining 50 tubes aliquots of 10 ml of the lower phase were introduced. Upper phase, in volumes of 10 ml per cycle, was automatically dispensed into tube number 0, repeatedly over 55 cycles resulting in approximately 5 hour operation. Thus, fifty five countercurrent cycles were performed, with each cycle consisting of 10 mixing pendula and 3 minutes phase separation time.

Initial load of crude extract after the funnel extraction: 125 mg

Number of cycles: 55

Equilibration time: 3 min 2.2.11 Removal of Malachite Green from the Countercurrent-purified Mycolic Acids To remove traces of malachite green derived from bacterial growth media (when *M. tuberculosis* was grown on LJ slants), the countercurrent-purified material was selectively precipitated in the following manner. Countercurrent-purified mycolic acids (92 mg) were placed in a WISP vial into which 1.0 ml chloroform was introduced. The dissolved mycolic acids were transferred into a pre-weighed round-bottom flask The vial was rinsed twice with 1.0 ml chloroform and the two aliquots of chloroform were added to that already present in the round-bottom flask. Subsequently, acetone was introduced drop-wise in 500 µl aliquots. In total, 26 ml of acetone was introduced and the white flakes of the precipitated-out mycolic acids were washed twice with 20 ml acetone. The acetone supernatant, with the dissolved malachite green was removed and the mycolic acids dried by evaporation.

The procedure was carried out at room temperature.

2.2.12 Determination of Mycolic Acids after Countercurrent Purification

In order to increase the accuracy of the HPLC determination of mycolic acids, the High Molecular Weight Internal Standard (C-100) was introduced into the countercurrent-purified mycolic acids before the saponification.

A sample of 0.5 mg of the countercurrent-purified mycolic acids was introduced into a WISP vial containing 5 µg of the High Molecular Weight Internal Standard (C-100). Saponification of mycolic acids was carried out with 2 ml of Reagent A at room temperature. The WISP vial was vortexed for 30 seconds. The extraction was carried out with 1.5 ml of Reagent B. After vortexing, the pH of the sample was checked and if necessary, adjusted to pH 1 with Reagent B.

Subsequently, 2.0 ml chloroform was added to each sample and vortexed for 30 seconds. The layers were allowed to separate. The bottom layers were removed with Pasteur pipettes, transferred to amber WISP vials and evaporated to dryness at 85° C. in a heat block-evaporator under a stream of nitrogen. To neutralize traces of acid carried over, 100 µl of reagent C was added to each sample and the fluid evaporated to dryness at 85° C. in a heat block-evaporator under a stream of nitrogen.

2.2.13 Determination of Yield of the Countercurrent Separation

In order to calculate the approximate yield of purification/separation, the amount of the mycolic acids present in the samples obtained after the countercurrent separation/purification was compared to the amount of these compounds present in the crude cellular extract introduced into the countercurrent apparatus. The calculations were based on the results obtained by the HPLC analysis.

It should be stressed, that it is essential for the calculation of the yield of the countercurrent separation, that the mycolic acids determined by HPLC should be within the tested linear range of the HPLC UV detector.

2.2.14 Methods Used in Monitoring Levels of Anti-mycolic Acids Antibodies

Bleeding: the animals were bled from the sublingual vein 12 days after the induction of arthritis. The blood was collected into sterile centrifuge tubes and allowed to clot for 16 hours at 4° C. The collected serum was centrifuged at 700–750 g for 20 minutes, diluted 1:1 v/v in glycerol and stored at −20° C.

ELISA protocol:

Coating of ELISA plates: The autoclaved coating antigen (in PBS buffer. pH 7.4), still hot, was introduced into ELISA wells in aliquots of 50 µl/well, with the solution being continuously stirred. Approximately 3 µg mycolic acids per well were introduced. The coated ELISA plates were incubated at room temperature for 16 hours. Subsequently the antigen solution was removed, the ELISA plates dried and the dry plates were stored at 4° C.

Blocking of ELISA plates: The blocking buffer (0.5% (m/v) casein in PBS pH 7.4) was introduced in aliquots of 200 µl/well. The ELISA plates were incubated at room temperature for 2 hours.

Binding of animal antibodies: Rat sera (mixed with glycerol 1:1 v/v) were diluted further in the diluting buffer 1:10 v/v. The final dilution was therefore 1:20 v/v. Aliquotes of 50 µl were introduced into wells in duplicate. The plates were incubated at room temperature for one hour. The sera were removed and the plates washed three times with the washing buffer using an Anthos Automatic Washer.

Quantification of the bound antibodies: Peroxidase anti-rat antibody conjugate diluted 1:1000 was introduced in aliquotes of 50 µl per well and incubated at room temperature for 30 minutes. After the removal of the conjugate, the ELISA plates were washed three times with the washing buffer.

The substrate solution comprising 10.0 mg O-phenylenediamine and 8.0 mg hydrogen peroxide in 10 ml of 0.1 M citrate buffer pH 4.5, was prepared immediately before use and introduced in 50 µl aliquotes per well. The plates were placed in a dark place and the colour development was monitored at 15, 30 and 60 minutes intervals using a SLT 340 ATC photometer at a wavelength of 450 nm.

2.2.15 Methods Used in Handling Experimental Animals in the Adjuvant Arthritis Experiments 2.2.15.1 Environmental Conditions Under Which the Experimental Animal Were Maintained Experimental animals: Six weeks old, female Lewis rats were accommodated in cages with a floor area of 864 cm$^2$ and a height of 12.5 cm. Four rats were maintained in each cage, except for the animals of group 6, which were maintained three per cage.

The animals were maintained at the Animal Facilities of the Medical Research Council in Pretoria.

Environmental conditions: Temperature and humidity in the animal facility were set at 20° C. (+/−1° C.) and 40% (+/−10%), respectively. Lighting was provided by means of fluorescent tubes. A light-darkness cycle of alternating 12 hour periods was set up.

Rats were fed on nutritionally controlled pellets manufactured by Epol, South Africa Cages: Rats were housed in transparent polypropylene cages with tightly fitting stainless steel lids. Wooden shavings, after autoclaving, were provided as nestling material.

Sanitation: Animal rooms, rat cages and glass bottles were cleaned and decontaminated once a week using Bronocide. Water bottles after washing were autoclaved once a week.

Identification of the experimental animals: Individual identification was accomplished by making ear marks.

2.2.15.2 Preparation of the Reagent Used for the Induction of Adjuvant Arthritis The method used for the induction of adjuvant arthritis was based on the method described by Wauben, Wagenaar-Hilber and Van Eden (1994).

In order to obtain a coarse surface, the bottom of a mortar bowl was ground with coarse grinding paper (100 grain). After the dust particles were removed, freeze-dried cells of M. tuberculosis H37 Ra, 100 mg, were transferred into the bowl. After the introduction of 3 drops of Freund's Incomplete Adjuvant (FIA) the bacteria were mixed very well with FIA for 2 minutes using a pestle. Once a thick paste was obtained, a few additional drops of FIA were introduced into the mortar and mixed with continuous grinding for a further half a minute. The thick paste was transferred into a 50 ml test tube using a glass Pasteur pipette. The mortar bowl was "rinsed" several times with the remaining FIA using a few drops at a time, until the entire volume of 10 ml was used. The final suspension of the freeze-dried cells of M. tuberculosis H37 Ra in FIA contained 100 mg of cells per 10 ml FIA.

2.2.15.3 Preparation of the Reagent Used for the Prevention of Adjuvant Arthritis An accurately weighed-off sample (10 mg) of freshly saponified mycolic acids, originating from M. tuberculosis H37 Rv, was introduced into 1 ml of FIA in a glass vial and heated on a heat-block evaporator at 80° C. until completely dissolved. After vortexing, the dissolved sample was removed from the heat block-evaporator and left at room temperature to cool down. From this stock solution the required concentrations of mycolic acids were prepared by introducing additional aliquotes of FIA.

2.2.15.4 Experimental Set-up

The experimental set-up is presented in Table 7.

A day before the start of the experiment, the rats were weighed and the thickness of the joints of their front and hind limbs was measured with a micrometer. Individual identification of rats was done by making ear marks.

Heat-killed and freeze-dried cells of M. tuberculosis H37Ra, 100 mg, were suspended in 10 ml of FIA by emulsifying the bacterial cells in FIA using a mortar and pestle. (For details, see section 2.2.15.2.). The administration of killed cells of M. tuberculosis H37Ra suspended in FIA, FIA alone and various doses of mycolic acids in FIA, using aliquots of 100 µl, was carried out in the form of intradermal injections at the base of the rats' tail.

The rats were divided into 12 groups and treated as illustrated in Table 7.

The rats were monitored daily for the appearance of any symptoms of arthritis such as swollen limbs, necrosis of the tail and nose bleeding. Two weeks into the experiment, the diameter of the joints in the front and hind limbs was measured every second day. Rats' mass was likewise monitored every second day.

To determine the level of anti-mycolic acids antibodies in the sera of the experimental animals, the rats were bled from the sublingual vein in the tongue on the 12-th day after the induction of arthritis.

TABLE 7

Experimental set-up for the induction of adjuvant arthritis

| | Day of the experiment | | Induction of | |
|---|---|---|---|---|
| Group number | Number of rats per group | Pre-treatment Day 0 | adjuvant arthritis Day 7 | Post-treatment Day 11 |
| Group 1 | 4 | FIA only, 100 µl | 1 mg H37Ra in 100 µl FIA | 0 |
| Group 2 | 4 | 0.1 mg MA in 100 µl FIA | 1 mg H37Ra in 100 µl FIA | 0 |
| Group 3 | 4 | 0.3 mg MA in 100 µl FIA | 1 mg H37Ra in 100 µl FIA | 0 |
| Group 4 | 4 | 1.0 mg MA in 100 µl FIA | 1 mg H37Ra in 100 µl FIA | 0 |
| Group 5 | 4 | 0 | 100 µl FIA | 0 |

TABLE 7-continued

Experimental set-up for the induction of adjuvant arthritis

| Group number | Number of rats per group | Pre-treatment Day 0 | Induction of adjuvant arthritis Day 7 | Post-treatment Day 11 |
|---|---|---|---|---|
| Group 6 | 6 | 0 | 1 mg H37Ra in 100 µl FIA | 0 |
| Group 7 | 4 | 0 | 1 mg MA in 100 µl FIA | 0 |
| Group 8 | 4 | 0 | 1 mg H37Ra in 100 µl FIA | 100 µl FIA |
| Group 9 | 4 | 0 | 1 mg H37Ra in 100 µl FIA | 0.1 mg MA in 100 µl FIA |
| Group 10 | 4 | 0 | 1 mg H37Ra in 100 µl FIA | 0.3 mg MA in 100 µl FIA |
| Group 11 | 4 | 0 | 1 mg H37Ra in 100 µl FIA | 1.0 mg MA 20 100 µl FIA |
| Group 12 | 4 | 0 | 0 | 0 |

2.2.15.5 Methods Used in the Radiological Assessment of Arthritis

Radiographs of the cadaver limbs originating from the control, arthritis and mycolic acids-treated rats were made using a Siemens Polymat 50 diagnostic X-ray machine. Fuji HRF film and Trimax T2 detail screens were used at a source-to-image distance of 109 cm. Exposure factors were 42 kVp and 4 mAs to optimise soft tissue visibility and bony detail.

Radiological examinations were carried out by Prof. R M Kirberger the Section of Pathology of the Veterinary Research Institute, Onderstepoort, Pretoria.

2.3 Results and Discussion

The results obtained concerning:
i) the influence of the modified method of purification on yield and purity of mycolic acids;
ii) the structural analysis of mycolic acids originating from *M. tuberculosis* using infra-red spectroscopy; and
iii) the stability of mycolic acids were presented and discussed in sections 1.3.1, 1.3.2 and 1.3.3.

2.3.1 Monitoring of the Symptoms of Adjuvant Arthritis

Figure 25A:
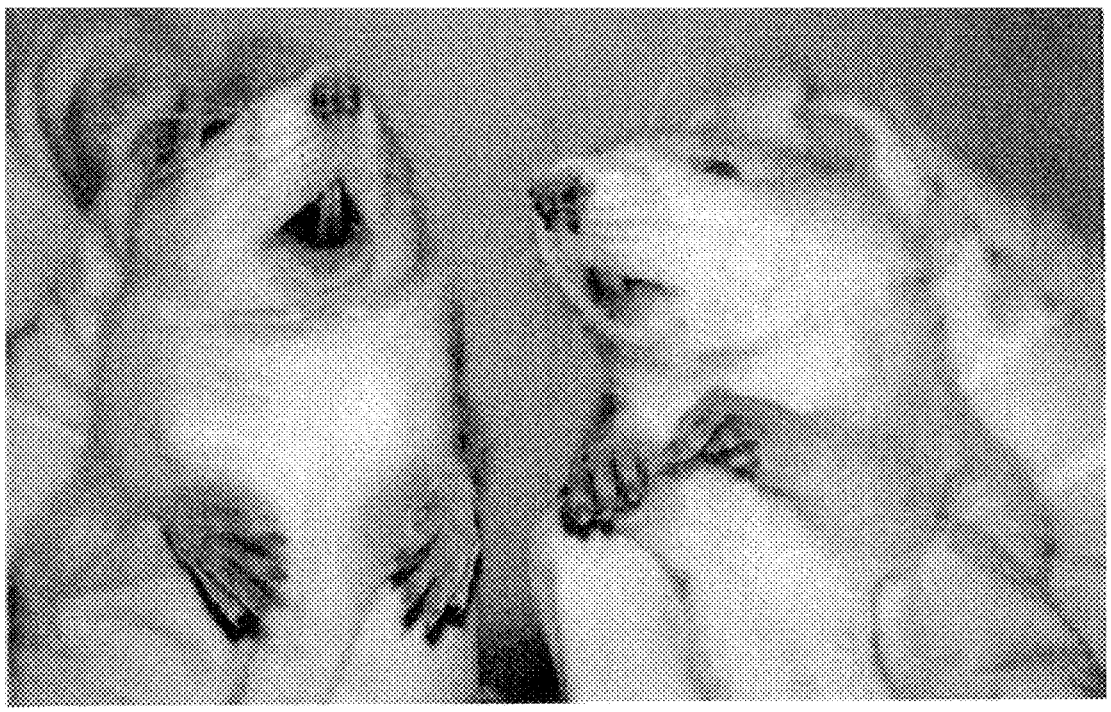
FIG. 25a is a photograph of two rats, the rat on the left being a control and having received only FIA, the rat on the right having received a reagent for the induction of adjuvant arthritis and showing a bleeding nose and arthritic nodules visible on the front paws.
Figure 25B:
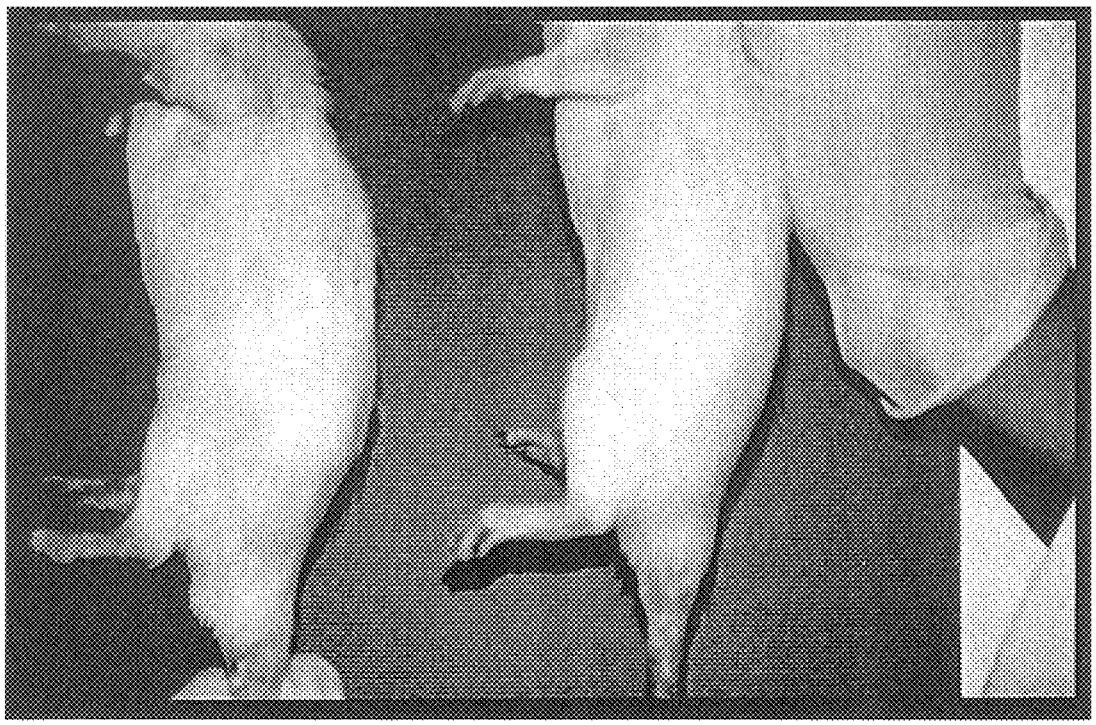
FIG. 25b is a photograph of two rats, the rat on the right having been pre-treated with 1 mg of mycolic acids/serum in FIA before having received a reagent for the induction of adjuvant arthritis and showing minimal signs of arthritis, the rat on the left not having been pre-treated before having received a reagent for the induction of adjuvant arthritis and showing swollen and inflamed arthritic hind legs.
Figure 26A:
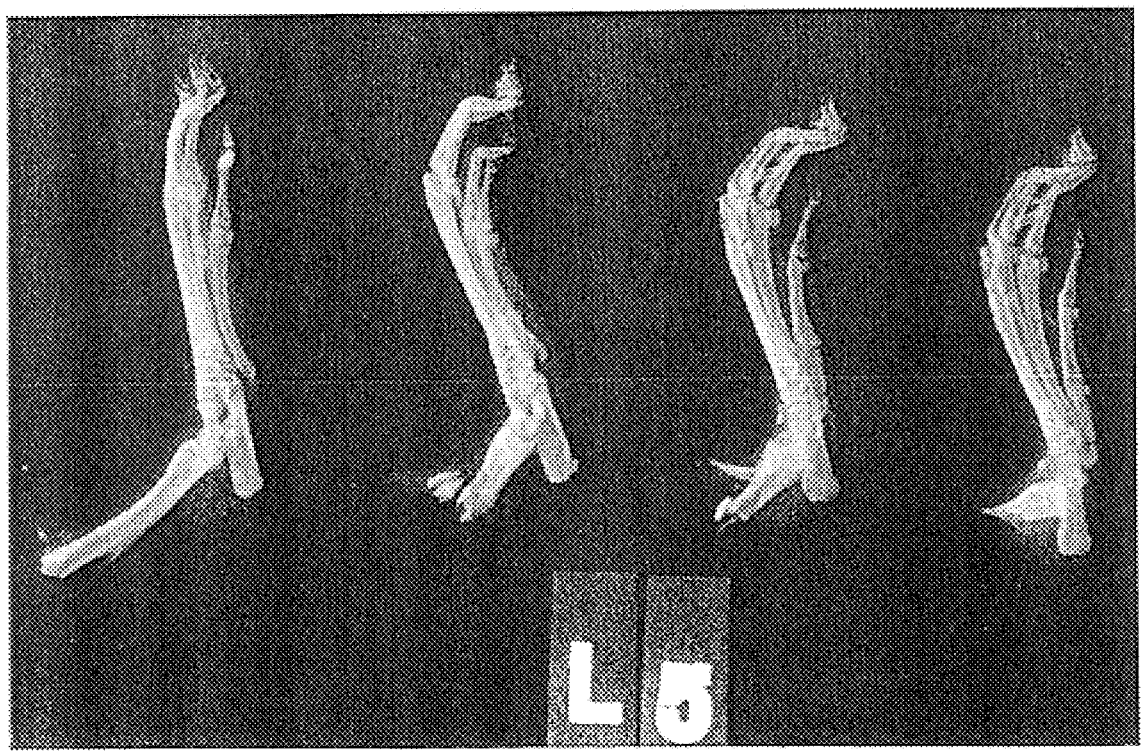
FIG. 26a shows X-ray photographs of the hind limbs of rats used in the arthritis experiments. Group 5 of Tables 8a and 8b—a "negative" control treated with Freund's Adjuvant only.
Figure 26A:
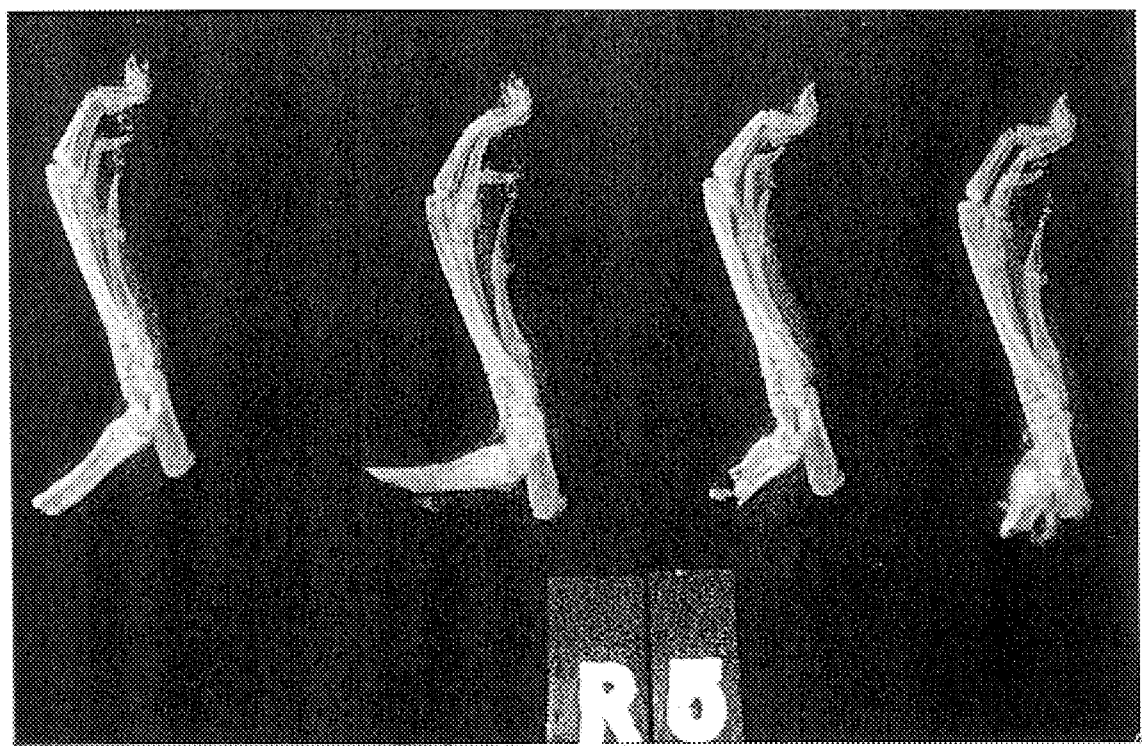
Figure 26B:
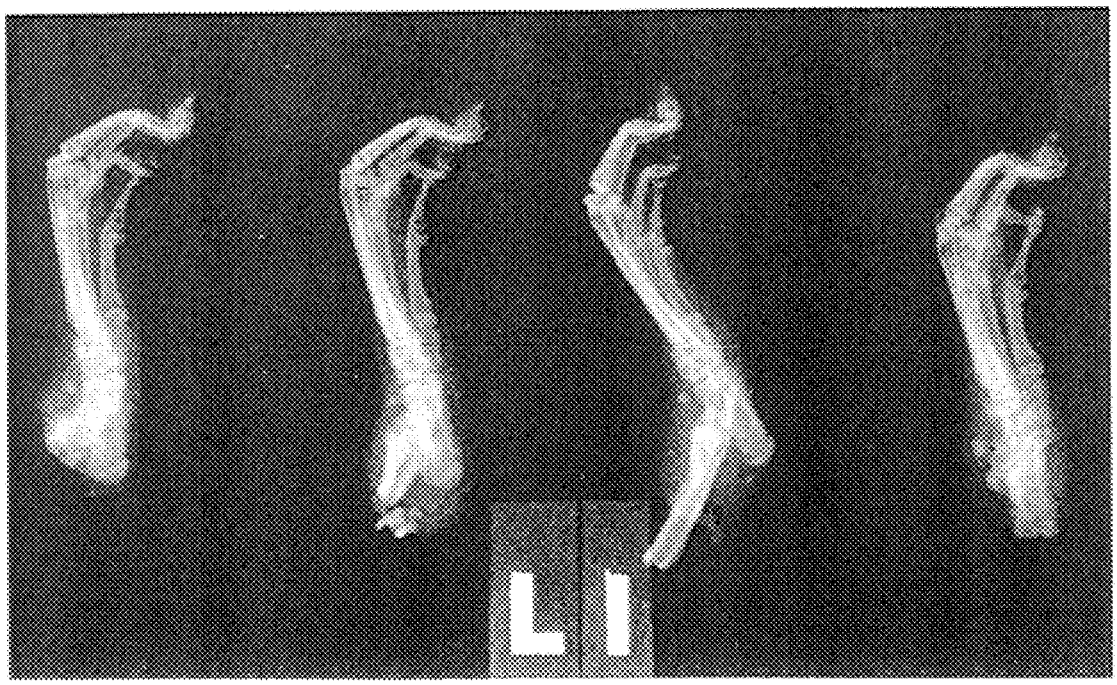
FIG. 26b shows X-ray photographs of the hind limbs of rats used in the arthritis experiments. Group 1 of Tables 8a and 8b—a "positive" control treated with *M. tuberculosis* H37Rv suspended in Freund's Adjuvant.
Figure 26B:

Successful induction of adjuvant arthritis (experimental details given 2.2.15.2, 2.2.15.3 and 2.2.15.4) was first observed four days after the administration of an arthritis-inducing dose of the suspension of *M. tuberculosis* H37Ra freeze-dried cells in Freund's Incomplete Adjuvant (FIA). The fist symptoms were those of a necrosis developing at the site of the injection. Other symptoms were observed at about 11 days after the administration of the cells of *M. tuberculosis* H37Ra in FIA and included swelling of the knuckles and joints as well as nose bleeding (FIGS. 25a, 25b and FIG. 26b). These symptoms peaked after approximately 16 to 21 days and subsequently subsided, except for the necrosis. Complete recovery was observed within the next two weeks.

The rats which were pre-treated with 0.1 mg and 0.3 mg mycolic acids developed less severe symptoms than those treated with FIA alone. Three rats pre-treated with 1 mg MA did not develop any symptoms indicative of the presence of the disease. The fourth rat in the same group (rat number 3 in FIG. 26c) did not receive the full dose of mycolic acids during pre-treatment, as part of the dose leaked out after the injection. This rat showed only moderate symptoms of arthritis in the hind limbs.

The rats which received injections of FIA only (FIG. 26a), did not show any symptoms. No toxic effects were observed among the control rats which were treated with mycolic acids suspended in FIA but without challenge with an arthritis-inducing dose of *M. tuberculosis* H37Ra in FIA.

Figure 26C:
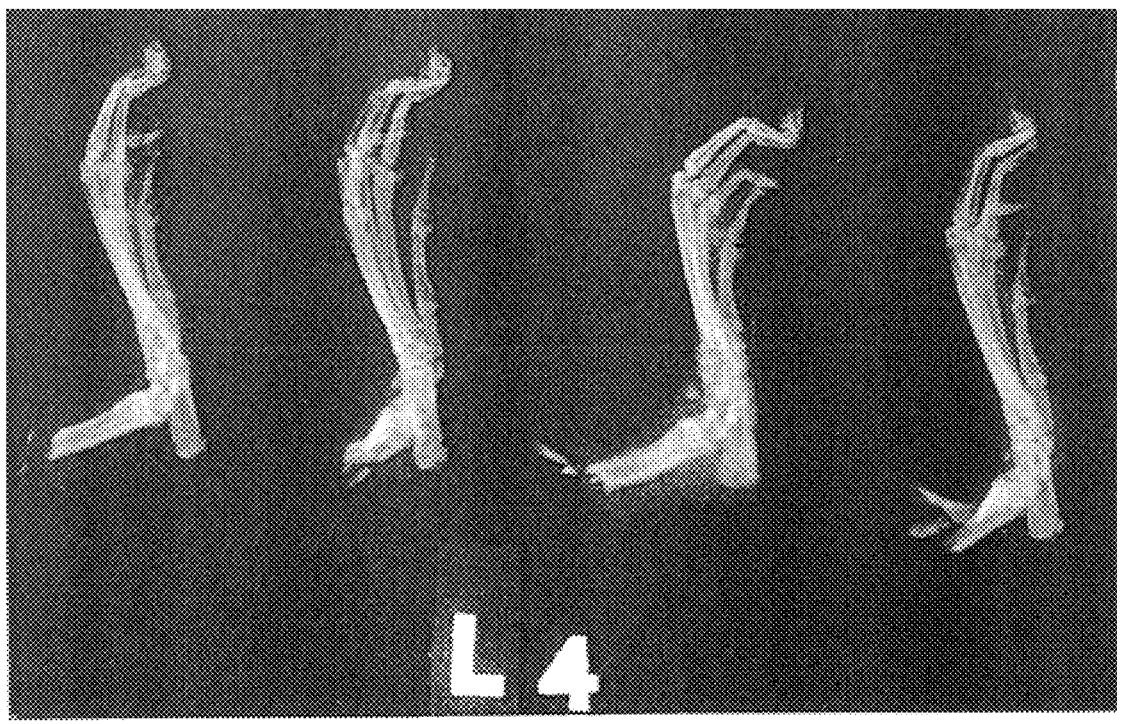
FIG. 26c shows X-ray photographs of the hind limbs of the rats pre-treated with 1 mg mycolic acids {from *M. tuberculosis*) prior to the induction of arthritis. Group 4 of Tables 8a and 8b.
Figure 26C:
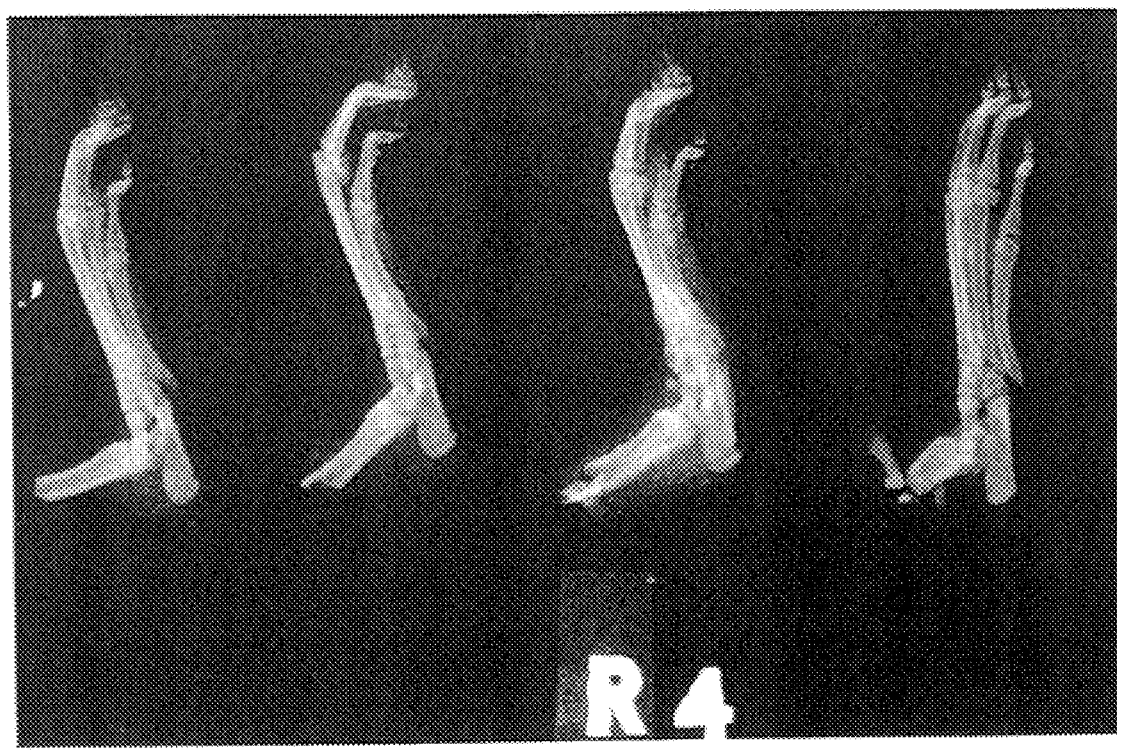
Figure 27:
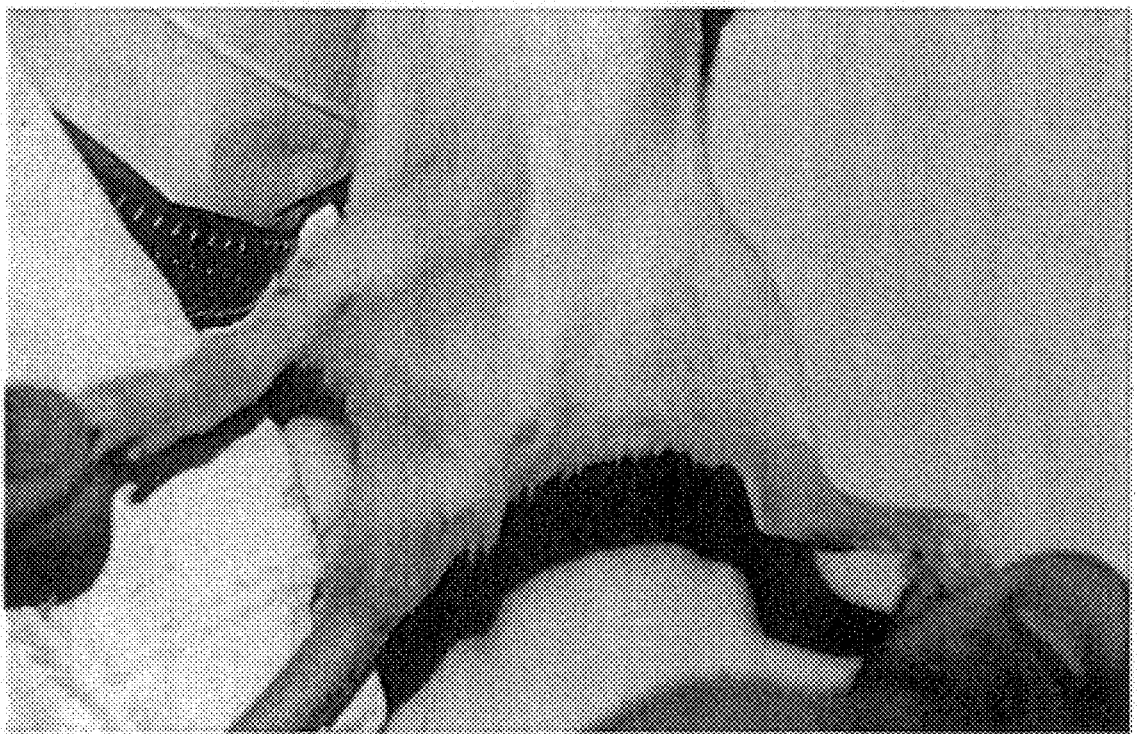
FIG. 27 shows the emaciation of a rat with typical induced adjuvant arthritis.

The results obtained in the experiment are summarized in Tables 8a and 8b and illustrated by photographs presented in FIGS. 25 to 27.

FIGS. 25a and 26b show the typical swelling of the joints and knuckles in the front paws of the experimental rats. FIG. 25a illustrates the bleeding from the nose caused by thrombocytopenia induced by the presence of a high concentration of immune complexes in the blood of the experimental animals.

TABLE 8a

Results obtained in rats treated with mycolic acids prior to the induction of adjuvant arthritis

| Group | Rat | Days | LF | RF | LB | RB | Necrosis | Nose bleed | Mass (g) | Avg mass |
|---|---|---|---|---|---|---|---|---|---|---|
| 1 | 1 | 16 | 2.1 | 1.6* | 5.3 | 4.3 | ++N | + | +12 | 13.4 |
| FIA + | 2 | | 3.2 | 2.9 | 3.6 | 3 | +++N | + | +7.8 | |
| H37Ra | 3 | | * | 2.3 | 3.8 | 2.7 | +++N | + | +8.3 | |
| | 4 | | 3 | 3.7 | 3.6 | 4.7 | +++N | + | −2.6 | |
| 2 | 1 | 16 | * | * | 2 | 2.3 | +++N | + | +26.2 | 24.5 |
| 0.1 mg | 2 | | 2.4 | 2.9 | * | 4.9 | +++N | + | +22.6 | |
| MA + | 3 | | 2.2 | 0.7 | 1.2 | 2.7 | +++N | + | +24.7 | |
| H37Ra | 4 | | 0.6 | 2.4 | 2.6 | 3.8 | ++N | + | +24.5 | |
| 3 | 1 | 16 | — | — | — | — | +++N | + | +31.2 | 17.6 |
| 0.3 mg | 2 | | 0.5 | 2.5 | 2.9 | 3.6 | ++N | + | +22.4 | |
| MA + | 3 | | 2.1 | 2.8 | 3.3 | 5.5 | +++N | + | +12.2 | |
| H37Ra | 4 | | 1.1 | 1 | 2.9 | 3.5 | ++++N | + | +4.4 | |
| 4 | 1 | 16 | — | 0.9 | — | — | ++N | + | +40.6 | 30.6 |
| 1 mg | 2 | | — | — | — | 1 | +++N | + | +31.4 | |
| MA + | 3 | | 1.5 | 2 | 4.2 | 4.3 | +++N | + | +4.9 | |
| H37Ra | 4 | | — | — | — | — | +N | + | +45.3 | |
| 5 | 1 | 16 | — | 1.1 | — | — | — | + | +35.2 | +29.6 |
| FIA | 2 | | — | 0.9 | — | 0.7 | — | — | +33.1 | |
| | 3 | | — | — | — | — | — | — | +23.9 | |
| | 4 | | — | 0.9 | — | 0.5 | — | + | +26.1 | |
| 7 | 1 | 21 | 0.5 | — | — | — | — | + | +39.9 | 36 |
| 1 mg | 2 | | 0.6 | 0.9 | — | 0.5 | — | — | +26.5 | |
| MA | 3 | | — | 0.8 | — | — | — | — | +37.7 | |
| | 4 | | — | 0.6 | — | — | — | + | +39.6 | |

Abbreviations:
Increase in the joint diameter of:
LF     Left front paw
RF     Right front paw
LB     Left back paw
RB     Right back paw
Nose bleed     Nose bleeding
Mass     Increase or decrease in mass
Avg mass     Average increase in mass per group
Max sympt     Day on which the most severe symptoms were observed TABLE 8b Results obtained in rats treated with mycolic acids administered after the induction of adjuvant arthritis

| Group | Rat | Days | LF | RF | LB | RB | Necrosis | Nose bleed | Mass (g) | Avg mass |
|---|---|---|---|---|---|---|---|---|---|---|
| H37Ra | 1 | 21 | 1.5 | 1.5 | 2.3 | 4.3 | ++++N | + | +19.8 | 17.5 |
| | 2 | | 1.35 | — | — | — | +++N | + | +29.5 | |
| | 3 | | — | — | — | 0.9 | ++N | + | +14.5 | |
| | 4 | | — | — | 1 | — | ++N | — | +19.5 | |
| | 5 | | — | 1.5 | 5.7 | 4.2 | +N | + | +5.3 | |
| | 6 | | — | 0.6 | 1.6 | 0.5 | +++N | + | +16.6 | |
| 7 | 1 | 21 | 0.5 | — | — | — | — | + | +39.9 | 36 |
| 1 mg | 2 | | 0.6 | 0.9 | — | 0.5 | — | — | +26.5 | |
| MA | 3 | | — | 0.8 | — | — | — | — | +37.7 | |
| | 4 | | — | 0.6 | — | — | — | + | +39.6 | |
| 8 | 1 | 21 | — | — | 4.3 | 3.1 | +++N | — | +24 | 26.6 |
| H37Ra | 2 | | — | — | 0.9 | 0.5 | +++N | — | +27.6 | |
| + FIA | 3 | | 1.9 | — | 2.7 | 3 | +++N | + | +9.9 | |
| | 4 | | — | 0.5 | — | — | +++N | + | +44.7 | |
| 9 | 1 | 21 | — | — | — | 2.7 | +++N | + | +6.4 | 14.8 |
| H37Ra | 2 | | 2.2* | — | — | 3 | ++++N | + | +14.6 | |
| + 0.1 mg | 3 | | — | — | 0.7 | 0.9 | +++++N | + | +20.9 | |
| MA | 4 | | 0.7 | 2.1 | 3.1 | 3 | +++N | + | +17.3 | |
| 10 | 1 | 21 | — | — | — | — | — | — | +32.5 | 27.2 |
| H37Ra | 2 | | — | — | — | — | +++N | + | +30.4 | |
| + 0.3 mg | 3 | | — | — | 0.5 | — | +++++N | — | +32.9 | |
| MA | 4 | | 1.5 | 2.9* | 3.1 | 2.2 | ++++++N | + | +13.1 | |
| 11 | 1 | 21 | 1.5 | 1.1 | 1.2 | 2.1 | ++++N | + | +25.2 | 23.1 |
| H37Ra | 2 | | 2.45 | 1* | 2.75 | 1.45 | ++++N | + | +18.2 | |
| + 1.0 mg | 3 | | — | 1.1 | 0.75 | — | +++N | + | +25.7 | |
| MA | 4 | | 2.7 | 0.65 | — | 2.25 | +++N | + | +23.1 | |
| 12 | 1 | 21 | — | 0.5 | — | — | — | — | +34.5 | 37.3 |
| Nothing | 2 | | — | 0.5 | — | — | — | — | +29.1 | |
| | 3 | | — | — | — | — | — | — | +46.5 | |
| | 4 | | — | — | — | — | — | — | +37.2 | |

Abbreviations:
LF    Left front paw
LB    Left back paw
Nose bleed    Nose bleeding
Avg mass    Average increase in mass per group
Max sympt    Day on which the most severe symptoms were observed
Increase in the joint diameter of:
RF    Right front paw
RB    Right back paw
MASS    Increase or decrease in mass FIGS. 25b as well as FIGS. 26b and 26c show a comparison between the rat pre-treated with 1 mg MA in FIA and the arthritic rat. The pronounced swelling and inflammation of hind leg joints of the rat in which adjuvant arthritis was successfully induced can be clearly distinguished from those rats that were protected with mycolic acids pre-treatment (FIGS. 25b and 26c).

Figure 25C:
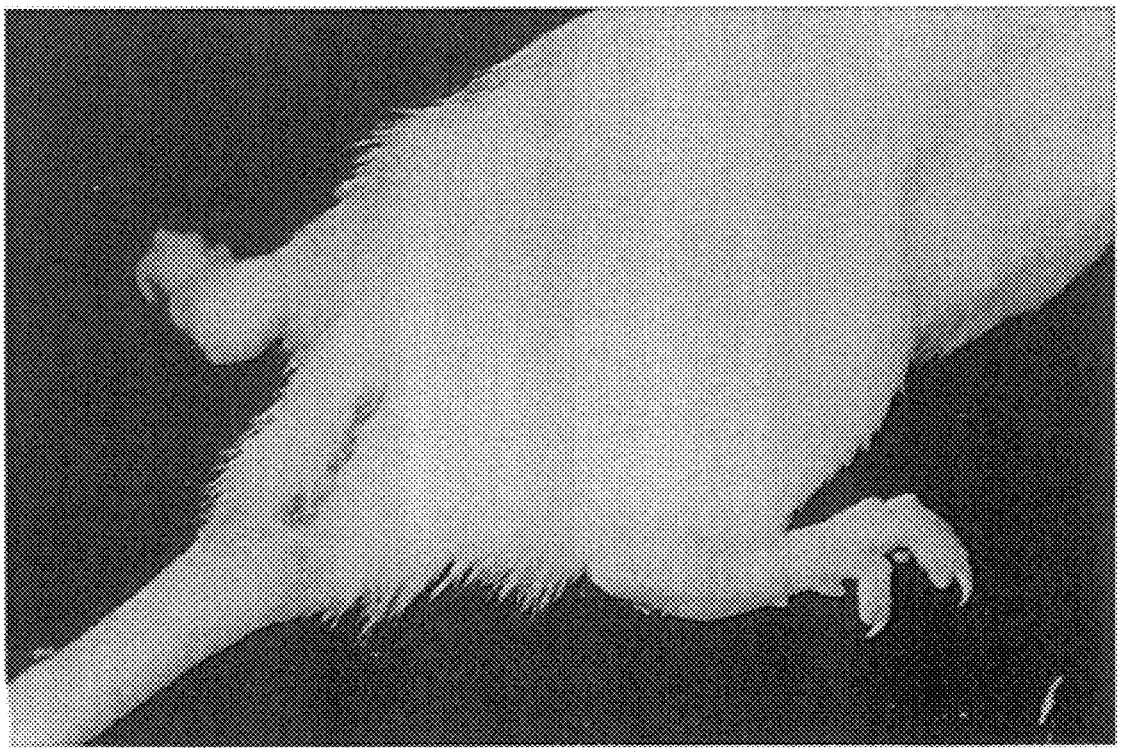
FIG. 25c is a photograph of the rat showing the typical deformation of the joints in the hind legs, the so-called "swimming position" and a necrosis developing at the site of the injection.

FIG. 25c shows the typical deformation of the joints in the hind legs, known as the "swimming position". The emaciation caused by adjuvant arthritis is evident from FIG. 27.

The results obtained in the experiment indicate a protective influence of mycolic acids at a dose of 1 mg administered before priming with *M. tuberculosis* H37Ra in FIA.

EXAMPLE 3

Immunogenic Properties of Countercurrent-purified Mycolic Acids 3.1 Materials
3.1.1 Culture

*Mycobacterium tuberculosis* H37Rv ATCC 27294—a virulent strain, originally isolated from an infected human lung. Type strain of the species.

The culture was purchased in lyophilized form from the American Type Culture Collection (ATCC), Maryland, USA.

3.1.2 Media
3.1.2.1 Growth Media

The following media were used for the cultivation of *M. tuberculosis:*

Löwenstein-Jensen (LJ) medium (slants) and Middlebrook 7H1-10 agar medium (plates).

A detailed composition of the ingredients necessary for the preparation of these media as well as the conditions recommended for their sterilization, are given in the Laboratory Manual of Tuberculosis Methods, Tuberculosis Research Institute of the SA Medical Research Council (1980, Chapter 6, pp 83–105; Second Edition, revised by E E Nel, H H Kleeberg and E M S Gatner).

The media were prepared by the National Tuberculosis Institute of the Medical Research Council of South Africa, in Pretoria.

3.1.2.2 Media Used for Washing and Diluting of Mycobacteria

The harvested bacteria were washed in sterile 0.9% m/v NaCl (Saarchem, Chemically Pure, RSA).

Medium used for the preparation of serial dilutions, preceding the determination of viable counts of *M. tuberculosis*, was prepared by dissolving Tween 80 (Merck, Chemically Pure) in 0.9% m/v NaCl (Saarchem, Chemically Pure) to a concentration of 0.01% v/v and distributing it in 9.0 ml aliquots into test-tubes. The autoclaved media were stored at 4° C.

3.1.3 Reagents
3.1.3.1 For the preparation of the reagents used for the extraction, derivatization and High-Performance Liquid Chromatography (HPLC) analysis of mycolic acids, HPLC Grade methanol (BDH) and double-distilled deionized water were used.

Reagent A: 25% potassium hydroxide (Saarchem, Analytical Grade) dissolved in methanol-water (1:1), i.e., 62.5 g potassium hydroxide was dissolved in 125 ml water and 125 ml methanol (BDH, HPLC Grade) was added.

Reagent B: Concentrated hydrochloric acid (Saarchem, Analytical Grade diluted 1:1 with water.

Reagent C: 2% potassium bicarbonate (BDH, Analytical Grade) dissolved in methanol-water (1:1), 10 g potassium bicarbonate was dissolved in 250 ml water and 250 ml methanol was added.

Reagent D: para-bromophenacylbromide dissolved in acetonitrile and crown ether (Pierce Chemical Co, Cat. No 48891) was dispensed in 500 $\mu$l quantities into small amber-coloured screw cap vials with Teflon-coated septa. The caps were tightened and the vials were wrapped with Parafilm. Reagent D was stored at 4° C.

Reagent E: Reagent E was prepared by mixing reagent B 1:1 with methanol.

HPLC Standard: High Molecular Weight Internal Standard (C-100) from Ribi ImmunoChem Research Company, Cat No R-50. The standard, 1 mg, was dissolved in 20 ml chloroform (BDH, HPLC Grade) at 4° C. and aliquots of 100 $\mu$l were dispensed into 4 ml amber WISP vials, dried, capped with Teflon-coated septa and stored at 4° C.

Chloroform (Saarchem, Analytical Grade, RSA)

Methylene chloride (BDH, UK, HPLC-Grade)

Reagents A, B, C and E were prepared fresh prior to experiments, taking all the necessary safety precautions.

3.1.3.2 The following reagents were used for the preliminary purification of crude bacterial extracts ("funnel extraction") and for the countercurrent purification of the extracted mycolic acids:

Chloroform (Saarchem, Chemically Pure)

Methanol (Saarchem, Chemically Pure)

Acetone (Saarchem, Chemically Pure)

Sodium chloride (Saarchem, Analytical Grade)

Double-distilled deionized water was used for the preparation of the required reagent concentrations. i.e.,:
39% v/v methanol
42% v/v chloroform
0.2 M NaCl 3.1.3.3 Reagents Used in the Induction of Anti-mycolic Acids Antibodies Unsaponified mycolic acids originating from M. tuberculosis; Marcol 52 immunization oil manufactured by Esso, RSA.

3.1.3.4 Reagents Used in Monitoring the Production of Anti-mycolic Acids Antibodies Glycerol (Merck, Analytical Grade) was used for diluting sera of the experimental animals.

ELISA reagents:

Basic buffer—PBS buffer: 8.0 g NaCl, 0.2 g KCl, 0.2 g $KH_2PO_4$ and 1.05 g $Na_2HPO_4$ per 1 l distilled water, adjusted to pH 7.4.

Diluting buffer: 0.5% (m/v) casein in PBS buffer adjusted to pH 7.4 was used for diluting of the experimental animals' sera (mixed with glycerol 1:1) and for the preparation of suitable dilutions of immunoreagents.

Blocking buffer: 0.5% (m/v) casein in PBS buffer adjusted to pH 7.4 was used for blocking of ELISA plates.

Washing buffer: 0.5% (m/v) casein in PBS buffer adjusted to pH 7.4 was used for washing of ELISA plates.

Coating antigen: unsaponified mycolic acids originating from M. tuberculosis, at a final concentration of 0.067 $\mu$g/$\mu$l. To prepare the coating antigen, 1 mg mycolic acids was dissolved in 100 $\mu$l chloroform and the solution introduced into 15.0 ml PBS buffer adjusted to pH 7.4. The solution was autoclaved at 121° C. for one hour.

Conjugates: Goat anti-rat antibody conjugated to peroxidase (H+L chains), Cappel (Cat No 55770). Rabbit anti-human gamma chain specific peroxidase conjugate (Sigma; A 8419).

Substrate: O-Phenylenediamine (Sigma; Cat No P-1526) and hydrogen peroxide (BDH).

Substrate buffer: 0.1 M citrate buffer (0.1 M citric acids and 0.1 M Tri sodium citrate), adjusted to pH 4.5.

ELISA plates were manufactured by Sterilin, UK.

3.1.3.4 Reagents Used in the Preparation of SDS-PAGE Gels

Laemmli buffer: 0.5 M Tris-HCl pH 6.8, 10% v/v glycerol, 10% m/v SDS and 0.05% m/v bromo phenol blue CAPS buffer pH 9.0: 3-[Cyclohexylamino]-1 propane sulphonic acid, (Sigma) buffer pH 9.0

TBS buffer pH 7.4: 20 mM Tris and 55 mM NaCl, containing 1% m/v fat-free milk powder and 0.05 % v/v Tween 20

SDS-PAGE gels: Sodium dodecyl sulphate polyacrylamide slab electrophoresis gel: a 4% stacking gel and a 6% separating gel comprising 30 mM Tris pH 8.0, 200 mM glycine and 17 mM SDS.

Substrate: 0.03 mM 4-chloronaphtol, 3% v/v hydrogen peroxide in 20 ml methanol, made up to 100 ml with TBS buffer pH 7.4

Immobilon-P Transfer membranes

Coomassie blue 3.1.4 Human Sera

Human sera used in the ELISA experiments originated from the Serum Bank of the Medical Research Council Tuberculosis Institute, Pretoria.

3.1.5 Experimental Animals

Seventeen weeks old Sprague-Dawley female rats were used for the induction of anti-mycolic acids antibodies. The animals were purchased from the Animal Centre at the South African Institute for Medical Research in Johannesburg.

Feed and water

Mice cubes, manufactured by EPOL and tap, autoclaved water were provided ad libitum.

Sanitation:

Bronocide, manufactured by Essential Medicines (Pty) Ltd, was used for sanitation purposes.

3.1.6 Plasticware

The following plasticware was used:

Disposable Petri's dishes (Promex, RSA)

ELISA plates (Sterilin, UK)

Sterile, disposable 50 ml centrifuge tubes (Corning, USA)

Disposable tips (Elkay, Denmark)

96well round bottom microplates (Nunc, Denmark)

3.2 Methods

The following methods were used in the experimental work:

3.2.1 Cultivation of the Bacterial Strains

The bacteria were cultivated at 37° C. using Löwenstein-Jensen (LJ) medium slants and Middlebrook 7H-10 agar medium plates.

The sterility of all the media was confirmed, before they were used in the experiments, by incubating them at 37° C. for 24 h.

For routine extraction of mycolic acids approximately 4-week old *M. tuberculosis* and 2-week old cultures of *M. vaccae*, grown on LJ slants, were used. When Middlebrook 7H-10 agar medium plates were used, 2-week old cultures of *M. tuberculosis* were harvested for the extraction of mycolic acids. For the preparation of bacterial suspensions used for the experimental induction of tuberculosis, approximately 2-week old cultures of *M. tuberculosis*, grown on LJ slants were used.

3.22 Viable and Total Bacterial Counts

For the viable count determination, serial suspensions of the harvested bacteria were prepared in the diluent medium (as specified under 1.1.2.2) to a density corresponding to a McFarland standard 4 (approximately OD of 1.0; using a Beckman DU 65 spectrophotometer, at 486 nm). Tenfold serial dilutions were prepared using 9 ml aliquots of the diluent medium. From the last three dilutions corresponding to $10^{-3}$, $10^{-4}$ and $10^{-5}$ of the original suspension, aliquots of 0.1 ml (100 μl) were withdrawn and spread over the surface of Middlebrook 7H-10 plates. The plates were incubated at 37° C. and the developed colonies counted after two to three weeks for *M. tuberculosis* and after one week for the plates seeded with *M. vaccae*.

The direct total count was performed using a Neubauer counting chamber and the autoclaved cultures of *M. tuberculosis* and *M. vaccae*, originally adjusted to a density corresponding to a McFarland standard 4 and suitably diluted with the diluent medium.

Statistical analysis of the bacterial counts included the mean values of bacterial counts and standard deviations.

3.2.3 Preparation of Mycolic Acids from Bacterial Samples

The preparation of bacterial samples comprised three steps:

harvesting of the Mycobacteria cells;

saponification and extraction of mycolic acids.

Glassware used for the harvesting, extraction, derivatization and HPLC analyses of mycolic acids was washed in 2% (v/v) Contrad (Merck), rinsed in water, followed by rinsing in chloroform, water, Technical Grade methanol, water and finally rinsed in double distilled deionized water. The washed glassware was dried in a warm air oven.

Harvesting was done by scraping the bacterial growth from the surface of media slants or agar plates (using sterile plastic loops) and by suspending them in Reagent A. Initial bacterial suspensions were prepared in Reagent A, by vortexing the harvested cells with sterile glass beads. Homogenous bacterial suspensions were prepared using sterile tissue homogenizers. Prior to the saponification, the density of the bacterial suspensions was adjusted to a density corresponding to a McFarland standard 4.

The saponification, extraction and derivatization of mycolic acids were carried out as described by Butler, Jost and Kilburn (1991), with minor modifications and are described under the relevant headings.

Saponification of the Mycobacteria in Reagent A was carried out in an autoclave at 121° C., for 30 min.

3.2.4. Extraction of Mycolic Acids

The saponified samples were allowed to cool after autoclaving. Into 2 ml samples containing crude extract, 1.5 ml Reagent B was introduced. After vortexing, the pH of each sample was checked and if necessary, adjusted to pH 1 with Reagent B.

Subsequently, 2.0 ml chloroform was added to each sample and vortexed for 30 seconds. The layers were allowed to separate. The bottom layers were removed with Pasteur pipettes, transferred to amber WISP vials and evaporated to dryness at 85° C. in a heat block-evaporator under a stream of nitrogen. To neutralize traces of acid carried over, 100 μl of reagent C was added to each sample and the fluid evaporated to dryness at 85° C. in a heat block-evaporator under a stream of nitrogen.

3.2.5 Storage of the Crude Extracted Mycolic Acids

The material obtained from the large-scale extraction of mycolic acids originating from *M. tuberculosis* and *M. vaccae*, i e., the crude bacterial extracts, was stored under acetone, at 4° C. in 4 ml amber WISP vials. To prevent evaporation/drying and the exposure to light, the caps of the WISP vials were covered with Parafilm.

3.2.6 Determination of Mycolic Acids Contents in Crude Extracts

Extracted mycolic acids were derivatized as follows:

To a cooled sample of crude extract (approximately 10 μg in 2.0 ml Reagent A), an aliquot of 1.0 ml chloroform was introduced, followed by the addition of 100 μl of Reagent D (derivatization reagent). The capped samples were vortexed for 30 seconds and heated for 20 minutes at 85° C. in a heat block-evaporator. Subsequently, the samples were cooled and 1.0 ml of Reagent E added. The samples were vortexed for 30 seconds and the layers allowed to separate. The bottom layers were removed with Pasteur pipettes and transferred to WISP-vials The vials were placed in a heat block-evaporator and their contents evaporated to dryness at 85° C. using a stream of nitrogen.

The residues were resuspended in 0.212 g (which corresponds to 160 μl) methylene chloride, capped and vortexed. Each reconstituted sample was introduced into a WISP vial containing 5 μg of the HPLC internal standard (prepared as described under 1.1.3.1), filtered through a 0.22 μm Millex GV4 filter with a polyethylene housing into another amber-coloured WISP-vial. The recapped vials were stored at 4° C. until ready for HPLC analysis.

3.2.7 HPLC Analysis and Quantification of Mycolic Acids

Repeatability and accuracy of the pipette used for the distribution of the HPLC standard was determined. The precision was established to be +/−1% and was confirmed prior to each aliquoting of the internal standard.

For the HPLC analysis 10 μl from each sample (maintained on ice during handling), was analyzed Control samples, i.e., 10 μl of filtered methylene chloride, were run prior to each set of samples analyzed. If a large number of samples was analyzed, in order to validate the reliability of the HPLC apparatus, control samples were run after every three or four test samples.

The reverse-phase HPLC analyses were carried out using a Waters 600 E System Controller High Performance Liquid Chromatography apparatus consisting of:

Microsep M741 Data Module;

Waters 712 WISP Autosampler;

Detector (Waters 486 Tunable Absorbance Detector);

Column: Nova-Pak C18 4 μm 3.9×150 mm and an end connector set for steel cartridge columns.

RKC Rex-C 4 Column Temperature regulator.

Running conditions were:
Mobile phase:
Solvent A: HPLC Grade methanol
Solvent B: HPLC Grade methylene chloride
Flow Rate: 2.5 ml/min
Column temperature: 30° C.
The detector was set at 260 nm.

Prior to use, the solvents were sparged with Instrument Grade helium. High Purity Nitrogen was used to control hydraulics of the WISP vials autosampler.

The HPLC gradient initially comprised 98% (v/v) methanol (Solvent A) and 2% (v/v) methylene chloride (Solvent B). The gradient was increased linearly to 80% A and 20% B at one minute; 35% A and 65% B at ten minutes, held for 30 seconds and then decreased over 10 seconds back to 98% A and 2% B. This ratio was maintained for 4 minutes to allow for stabilization of the system prior to injection of the next sample.

Mathematical quantification of mycolic acids was carried out by comparing the combined peak areas of the tested samples to the peak area of the introduced quantity of the High Molecular Weight Internal HPLC Standard.

3.2.8 Preliminary Purification of Crude Mycobacterial Extracts

In order to shorten the time required for the countercurrent purification of the crude mycobacterial eats, an additional preliminary extraction step was introduced. This step had a dual purpose:

i) to remove unnecessary cellular components from the crude extract prior to the countercurrent purification and ii) to reduce soap fraction in the crude bacterial extracts.

A portion of the crude extracted material (approximately 3–4 g) was suspended in a minimum volume of the lower phase solvent (usually 100 ml), transferred into a separation funnel and mixed with an equal volume of the upper phase solvent. The phases were allowed to separate and the upper phase was removed and stored at 4° C. Into the remaining lower phase an equal volume of the upper phase solvent was again introduced and the process of the phase separation was repeated.

The second upper phase was removed and stored at 4° C. and the second lower phase was dried in a Buchi Rotoevaporator RE 120, at 75° C. and its mass recorded.

3.2.9 Countercurrent Purification of Mycolic Acids Originating from M. tuberculosis and M. vaccae Countercurrent apparatus A countercurrent apparatus produced by H O POST, Instrument Company Inc., Middle Village, N.Y. was used during the investigations. The "trains" in this model consisted of 2×250 inter-connected tubes.

Solvent system used in the countercurrent apparatus

The solvent system used for the countercurrent separation consisted of:

42% v/v chloroform (Saarchem, Chemically Pure Reagent)

39% v/v methanol (Saarchem, Chemically Pure)

19% v/v 0.2 M NaCl (Saarchem, Chemically Pure).

Double-distilled deionized water was used for the preparation of the solvent system.

The components were mixed, equilibrated and the upper and lower phases were collected using a separation funnel.

The composition of the upper phase was established to be: 15% v/v chloroform 52% v/v methanol and 3.3% v/v 0.2 M NaCl.

The composition of the lower phase was established to be: 68% v/v chloroform, 27% v/v methanol and 5% v/v 0.2 M NaCl.

The countercurrent purification process was carried out under the following conditions:

A countercurrent distribution train comprising 55 tubes, numbered 0–54, was used in the experiments. The upper phase solvent, a volume of 600 ml, was introduced into a buffer reservoir. A sample of 125 mg of mycolic acids after the preliminary purification was dissolved in 50 ml of the lower phase solvent, divided into five aliquots and introduced into first five tubes, numbered 0–4, Subsequently, 10 ml of the upper phase solvent was introduced into each of one first five countercurrent tubes. Into the remaining 50 tubes aliquots of 10 ml of the lower phase were introduced. Upper phase, in volumes of 10 ml per cycle, was automatically dispensed into tube number 0, repeatedly over 55 cycles resulting in approximately 5 hour operation. Thus, fifty five countercurrent cycles were performed, with each cycle consisting of 10 mixing pendula and 3 minutes phase separation time.

Initial load of crude extract after the funnel extraction: 125 mg

Number of cycles: 55

Equilibration time: 3 min 3.2.11 Removal of Malachite Green from the Countercurrent-purified Mycolic Acids To remove traces of malachite green derived from bacterial growth media (when M. tuberculosis was grown on LJ slants), the countercurrent-purified material was selectively precipitated in the following manner. Countercurrent-purified mycolic acids (92 mg) were placed in a WISP vial into which 1.0 ml chloroform was introduced. The dissolved mycolic acids were transferred into a pre-weighed round-bottom flask. The vial was rinsed twice with 1.0 ml chloroform and the two aliquots of chloroform were added to that already present in the round-bottom flask. Subsequently, acetone was introduced dropwise in 500 $\mu$l aliquots. In total, 26 ml of acetone was introduced and the white flakes of the precipitated-out mycolic acids were washed twice with 20 ml acetone. The acetone supernatant, with the dissolved malachite green, was removed and the mycolic acids dried by evaporation.

The procedure was carried out at room temperature.

3.2.12 Determination of Mycolic Acids After Countercurrent Purification

In order to increase the accuracy of the HPLC determination of mycolic acids, the High Molecular Weight Internal Standard (C-100) was introduced into the countercurrent-purified mycolic acids before the saponification.

A sample of 0.5 mg of the countercurrent-purified mycolic acids was introduced into a WISP vial containing 5 $\mu$g of the High Molecular Weight Internal Standard (C-100). Saponification of mycolic acids was carried out with 2 ml of Reagent A at room temperature. The WISP vial was vortexed for 30 seconds. The extraction was carried out with 1.5 ml of Reagent B. After vortexing, the pH of the sample was checked and if necessary, adjusted to pH 1 with Reagent B.

Subsequently, 2.0 ml chloroform was added to each sample and vortexed for 30 seconds. The layers were allowed to separate. The bottom layers were removed with Pasteur pipettes, transferred to amber WISP vials and evaporated to dryness at 85° C. in a heat block-evaporator under a stream of nitrogen. To neutralize traces of acid carried over, 100 $\mu$l of reagent C was added to each sample and the fluid evaporated to dryness at 85° C. in the heat block-evaporator under a stream of nitrogen.

Therefore, the main difference between the determination of mycolic acids after countercurrent purification and in the crude extract was the time of introduction of the Internal Standard.

3.2.13 Determination of Yield of the Countercurrent Separation

In order to calculate the approximate yield of purification/separation, the amount of the mycolic acids present in the samples obtained after the countercurrent separation/purification was compared to the amount of these compounds present in the crude cellular extract introduced into the countercurrent apparatus. The calculations were based on the results obtained by the HPLC analysis.

It should be stressed, that it is essential for the calculation of the yield of the countercurrent separation, that the mycolic acids determined by HPLC should be within the tested linear range of the HPLC UV detector.

3.2.14 Infra-red Spectroscopy

Samples of mycolic acids to be analyzed by infra-red spectroscopy were prepared in the following manner. Countercurrent-purified mycolic acids, 1 mg, were dissolved in 1 ml chloroform, introduced into 200 mg KBr and thoroughly mixed. After the evaporation of chloroform, a pellet of mycolic acids in KBr was prepared by using a Shimadzu tablet die and applying a force of approximately 100 kilonewtons on the sample for 10 minutes. A control pellet was prepared using only chloroform, without mycolic acids added to the preparation. The control pellet was used to determine the background infra-red spectrum. The spectra were analyzed on a Perkin Elmer 1600 series FT-IR system and plotted on a Roland Digital Group X-Y Plotter DXY-1200.

3.2.15 Determination of the Stability of the Countercurrent-purified Mycolic Acids A pooled sample of the countercurrent-purified mycolic acids was prepared by introducing five batches of countercurrent-purified mycolic acids into a container, dissolving them in chloroform and mixing the contents very well. The chloroform was evaporated using a Buchi Rotoevaporator RE 120, at 75° C. and the sample dried under a stream of nitrogen. The pooled sample was divided into two parts which constituted two stock samples. The first stock sample was re-saponified and the second was left as a non-saponified stock sample. From both stock samples individual aliquots were withdrawn and placed at −20° C., 4° C. and 25° C. Three samples were prepared per each time point and HPLC analyses were carried out after 6 weeks, 3, 6, 9 and 12 months of storage.

3.2.16 Methods Used in the Experimental Production of Anti-mycolic Acids Antibodies Experimental animals: Sprague-Dawley female rats, 17 weeks old were used. Three animals were used per each antigen dose.

The animals were maintained at the Animal Facilities of the Medical Research Council in Pretoria.

Environmental conditions: Temperature and humidity in the animal facility were set at 20° C. (+/−1° C.) and 40% (+/−10%), respectively. Lighting was provided by means of fluorescent tubes. A light-darkness cycle of alternating 12 hour periods was set up.

Cages: Rats were housed in transparent polypropylene cages with tight fitting stainless steel lids. Wooden shavings, after autoclaving, were provided as nestling material.

Sanitation: Animal rooms, rat cages and glass bottles were cleaned and decontaminated once a week using Bronocide. Water bottles after washing were autoclaved once a week.

Identification of the experimental animals: Individual identification was accomplished by making ear marks.

Antigen: Unsaponified mycolic acids originating from *M. tuberculosis,* suspended in Marcol 52 oil.

Dose: Three doses of the antigen were used: 1.0, 0.1 and 0.01 mg mycolic acids in 100 $\mu$l of Marcol 52 oil per rat per immunization procedure. A control group received 100 $\mu$l Marcol 52 oil, only.

Route of antigen introduction: The antigen was injected subcutaneously at the underneath site of the rat's tail base.

Frequency of immunization: the animals were immunized at 14 days intervals.

Bleeding: the animals were bled from the tongue vein at 14 days intervals. The blood was collected into sterile centrifuge tubes and allowed to clot for 16 hours at 4° C. The collected serum was centrifuged at 700–750 g for 20 minutes, diluted 1:1 v/v in glycerol and stored at −20° C.

3.2.17 Methods Used in Monitoring Levels of Anti-mycolic Acids Antibodies

ELISA protocol:

Coating of ELISA plates: The autoclaved coating antigen (in PBS buffer. pH 7.4), still hot, was introduced into ELISA wells in aliquots of 50 $\mu$l/well, with the solution being continuously stirred. Approximately 3 $\mu$g mycolic acids per well were introduced. The coated ELISA plates were incubated at room temperature for 16 hours. Subsequently, the antigen solution was removed, the ELISA plates dried and the dry plates were stored at 4° C.

Blocking of ELISA plates: The blocking buffer (0.5% (m/v) casein in PBS pH 7.4) was introduced in aliquotes of 200 $\mu$l/well. The ELISA plates were incubated at room temperature for 2 hours.

Binding of animal and human antibodies: Rat or human sera (mixed with glycerol 1:1 v/v) were diluted further in the diluting buffer 1:10 v/v. The final dilution was therefore 1:20 v/v. Aliquotes of 50 $\mu$l were introduced into wells in duplicate. The plates were incubated at room temperature for one hour. The sera were removed and the plates washed three times with the washing buffer using an Anthos Automatic Washer.

Quantification of the bound antibodies: Peroxidase anti-rat antibody conjugate (or peroxidase anti-human conjugate) diluted 1:1000 was introduced in aliquotes of 50 $\mu$l per well and incubated at room temperature for 30 minutes. After the removal of the conjugate, the ELISA plates were washed three times with the washing buffer.

The substrate solution comprising 10.0 mg O-phenylenediamine and 8.0 mg hydrogen peroxide in 10 ml of 0.1 M citrate buffer pH 4.5, was prepared immediately before use and introduced in 50 $\mu$l aliquotes per well. The plates were placed in a dark place and the colour development was monitored at 15, 30 and 60 minutes intervals using a SLT 340 ATC photometer at a wavelength of 450 nm.

3.2.18 Methods Used in Evaluating Specificity of Human Anti-mycolic Acids Antibodies For the determination of the specificity of antibodies recognising mycolic acids, the inhibition ELISA was used. Coating of the ELISA plates with mycolic acids and blocking of the plates were carried out as described under 3.2.17.

Competition step: Human patient's (patient No 38) serum, 75 $\mu$l, was mixed with an equal volume of mycolic acids/mouse serum conjugate (prepared as described in section 1.2.16.4). Human control serum was likewise mixed with 75 $\mu$l of the conjugate. Two additional controls were prepared by mixing 75 $\mu$l of control mouse serum with 75 $\mu$l of the human patient's and control human sera. The samples were incubated for 1 hour at room temperature.

Subsequently, 625 $\mu$l of diluting buffer (section 3.1.3.4) was introduced into the each mixture, resulting in a final volume 775 $\mu$l (final dilution of the human sera was therefore 1:10). The diluted samples were mixed and 50 $\mu$l aliquots were loaded in triplicate onto ELISA plates, coated with mycolic acids. The plates were incubated on an ELISA shaker for 1 hour at room temperature. After washing (three times with the washing buffer using an Anthos Automatic Washer) the wells were aspirated and the anti-human gamma-chain specific peroxidase conjugate diluted 1:1000 was introduced into each well. The plates were incubated for 30 minutes at room temperature and again washed three times. The preparation of the substrate and quantification of the bound antibodies was carried out in the same manner as described under 3.2.17.

3.2.22 Preparation of Gel Electrophoresis

Preparation of human sera

Patients' sera were centrifuged at 3 000 g, for 10 min at 4° C., using a BHG Hermle centrifuge model 2320. After centrifugation and heat inactivation at 56° C. for 30 min, the sera were maintained at −70° C.

Sodium dodecyl sulphate polyacrylamide gel electrophoresis (SDS-PAGE)

The mouse serum and mycolic acids-mouse serum conjugates (prepared as described under 1.2.16.3 and 1.2.16.4, respectively) were diluted with Laemmli buffer (Laemmli, 1970) comprising 0.5 M Tris-HCl pH 6.8, 10% v/v glycerol, 10% m/v SDS and 0.05% m/v bromo phenol blue, and separated on a vertical sodium dodecyl sulphate polyacrylamide slab electrophoresis gel system (SDS-PAGE) (Owl system 1.5 mm×160 mm×140 mm). The gel consisted of a 4% stacking gel and a 6% separating gel in an electrode buffer comprising 30 mM Tris pH 8.0, 200 mM glycine and 17 mM SDS.

The SDS-PAGE gels were initially run at a voltage of 60 V/sec for one hour, after which the voltage was turned up to 100 V/sec for additional two to three hours. The gels were run in an electric field created by the Electrophoretic Constant Power Supply (ECPS 2000/300) produced by Pharmacia Biotechnology.

Western Blot

After the separation of the mouse serum proteins, the gel was equilibrated in CAPS buffer pH 9.0 (as specified under 3.1.3.4). An Immobilon-P Transfer membrane was equilibrated in methanol for one minute and then washed with CAPS (3-[Cyclohexylamino]-1 propane sulphonic acid, Sigma) buffer. The separated mouse proteins were transferred from the SDS-PAGE gel to the Immobilon membrane with a Biorad Transblot-SP semi-dry transfer cell (power supply: ECPS 2000/300 from Pharmacia Biotechnology).

The strips present on the Immobilon membrane were cut out and blocked by incubation in TBS buffer pH 7.4 (20 mM Tris, 55 mM NaCl) containing 1% m/v fat-free milk powder and 0.05% V/V Tween 20.

Each strip of the Immobilon membrane contained one lane of the mouse serum and one lane of the mouse serum-mycolic acids conjugate. The control strip comprised one lane of the standard Low Molecular Weight Markers, one lane of the mouse serum and of the mouse serum-mycolic acids conjugate. The control strip was stained with Coomassie blue. The remaining strips were individually incubated in either patient or control sera at 4° C. for 16 hours. The sera of both types were diluted 1:6 v/v in the blocking buffer (TBS pH 7.4, 1% m/v fat free milk powder and 0.05% v/v Tween 20).

The membrane strips were subsequently incubated with a mixture of anti-human IgG+IgM peroxidase conjugate diluted 1:500 with the blocking buffer, at room temperature for three hours and excess antibody was removed by three rinses in TBS buffer pH 7.4 containing 1% m/v fat free milk powder. The blots were developed by adding the substrate, i.e.: 0.03 mM 4-chloronaphtol, 3% v/v hydrogen peroxide in 20 ml methanol, made up to 100 ml with TBS buffer pH 7.4.

3.2.23 Methods Used in the Purification of CD4$^+$ Single Positive (SP), CD8$^+$ Single Positive, CD4- and CD8-Double Negative (DN) αβ TCR Positive Cells from the Human Peripheral Blood Purification of these cells was performed according to the procedure described by Niehues et al., (1994) with small modifications.

Peripheral blood mononuclear cells (PBMC) were isolated from 100 to 200 ml of blood from healthy individuals, using density gradient centrifugation over Ficoll-Hypaque. Red blood cells were lysed with 0.015 M $NH_4Cl$ and the remaining cells were resuspended in PBS buffer containing 1% v/v BSA and 0.01% m/v sodium azide to a concentration of 10 to $20×10^4$ cells/ml. The cells were then incubated on ice with the specific mouse monoclonal antibody recognising a framework determinant of the αβTCR WT31, at 10 µl/10 cells.

After 30 min, the cells were washed and positively selected with Dynal M-450 magnetic beads coated with a goat anti-mouse IgE antibody. The volume ratio between target cells and the beads was 1:40. The cells and beads mixture was gently rotated for 30 min at 4° C.

The cell suspensions were then exposed to a strong magnetic field and the non-adherent cells were removed. Adherent cells were allowed to detach by an overnight incubation at 37° C. and were then subjected to two rounds of immunodepletion with anti-CD8 mAb covalently coupled to magnetic beads and one round of depletion with anti-CD4 mAb, both covalently coupled to magnetic beads (M-450 Dynal).

Immunomagnetic depletions were performed at bead to target cell ratios of 40:1 with gentle rotation for 30 min at 4° C.

Cells bound to the anti-CD4 magnetic beads and to the anti-CD8 magnetic beads were used directly as a source of T-cell RNA.

The isolated CD4, CD8 and DN cells did not contain CD20, CD13, CD14 or CD34$^+$ cells and were >90% viable. The assessment of the cell viability was carried out using propidium iodide staining and Fluorescence Activated Cell Sorter (FACS).

Cells that did not bind to WT31 in the first selection step were irradiated (30 Gy) and used as autologous total APCs (Antigen Presenting Cells).

Induction of CD1 on autologous APC was carried out as described by Porcelli, Morita and Brenner (1992). Human monocytes were isolated from leucocyte concentrates originating from blood of normal donors by plastic adherence and detached by incubation at 37° C. in PBS with 0.53 mM EDTA. Adherent cells comprised typically more than 90% CD 13$^+$ and MHC class II$^+$ abut tested negative for CD1a, -b and -c by surface staining. To induce CD1 expression, monocytes were cultured in RPM1 1640 tissue culture medium containing 10% fetal calf serum with 100 units/ml of GM-CSF and IL-4 for 60 hours. The cells were collected by desorption using PBS with 0.53 mM EDTA Proliferation assay: The cells were suspended in RPM1 1640 tissue culture medium supplemented with 2 mM glutamine, 0.25% m/v refobacine and 5% v/v heat-inactivated, pooled human AB serum. SP and DN cells were plated in triplicate into round-bottomed 96-well tissue culture microplates, stimulated with mycolic acids (at concentrations of 5, 25, and 50 µg/ml and a mutagen, phytohemagglutinin (PHA), at a concentration of 3.3 µg/ml). The cells were incubated for 72 hours at 37° C. in a humidified $CO_2$ incubator (5% $CO_2$).

During the final 16 hours of incubation, the cells in the microplates were pulsed with $^3$H-thymidine (0.5 µCi/well).

Proliferation of SP and DN cells was determined by incorporation of $^3$H-thymidine as measured by standard liquid scintillation counting. Dose response curves were generated. Autologous, irradiated (30 Gy) APC or CD1$^+$ APC cells were added at a ratio of 4:1 in all experiments. The results were expressed at mean cpm +/–SEM, from which background values (medium alone) were subtracted.

3.3 Results and Discussion

The results obtained concerning:
i) the influence of the modified method of purification on yield and purity of mycolic acids;
ii) the structural analysis of mycolic acids originating from *M. tuberculosis* using infra-red spectroscopy; and
iii) the stability of mycolic acids were presented and discussed in sections 1.3.1, 1.3.2 and 1.3.3.

3.3 Investigations of the Immunogenic Properties of Countercurrent-purified Mycolic Acids These investigations were based on the following experiments:
3.3.1 The induction of antibodies against mycolic acids in the experimental rats;
3.3.2 The detection of anti- mycolic acids antibodies in human tuberculosis patients;
3.3.3 Response of human CD4 T cells to the in vitro stimulation with mycolic acids.

The following results were obtained 3.3.1 The Induction of Antibodies Against Mycolic Acids in the Experimental Animals In order to determine the immunogenicity of mycolic acids, suspensions of a methylester form of mycolic acids in oil were used for the immunization of Sprague-Dawley rats, as described under 3.2.16. The antibody response was monitored and the ELISA results obtained after a treatment period of 3 months, are presented in FIG. 28. A dose related response was observed for the induction of antibodies specific for mycolic acids, immobilized on the ELISA plates as described under 3.2.17.

Figure 28:
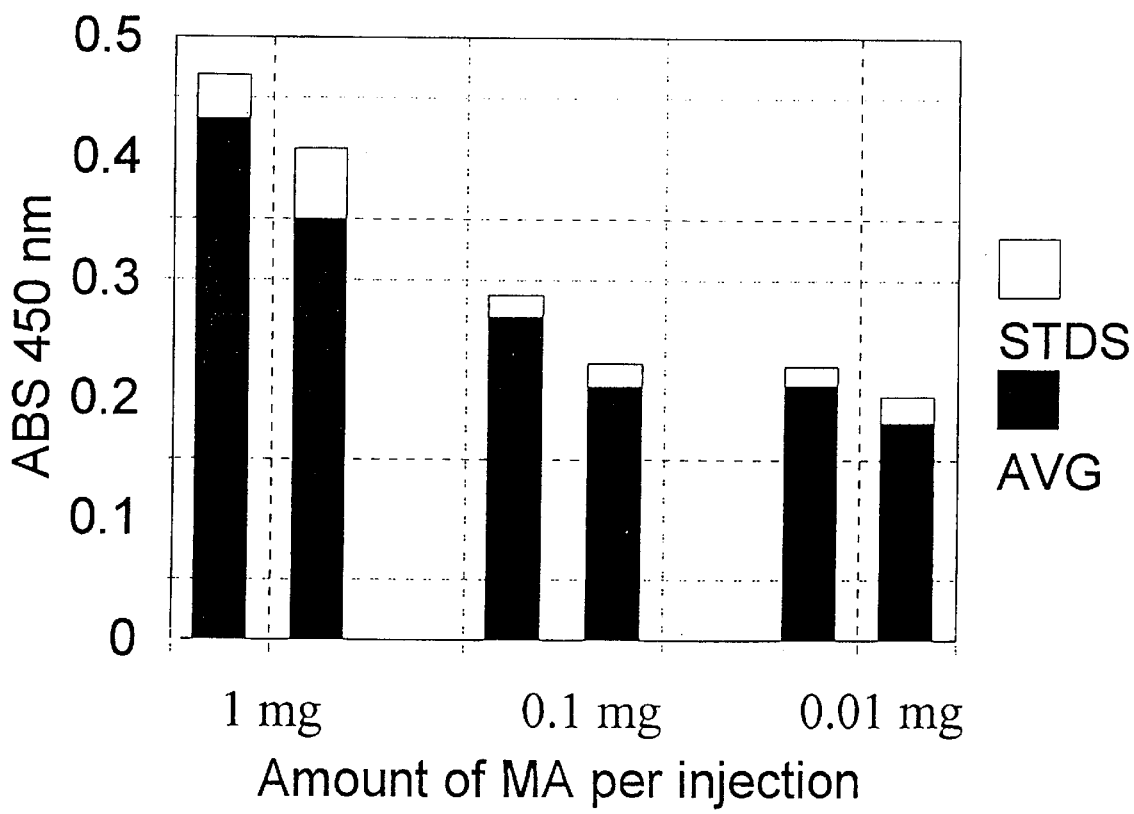
FIG. 28 shows rat antibody response to mycolic acids suspended in oil after three months' treatment using 1.0, 0.3 and 0.1 mg mycolic acids per immunization, after three months treatment.
Figure 29A:
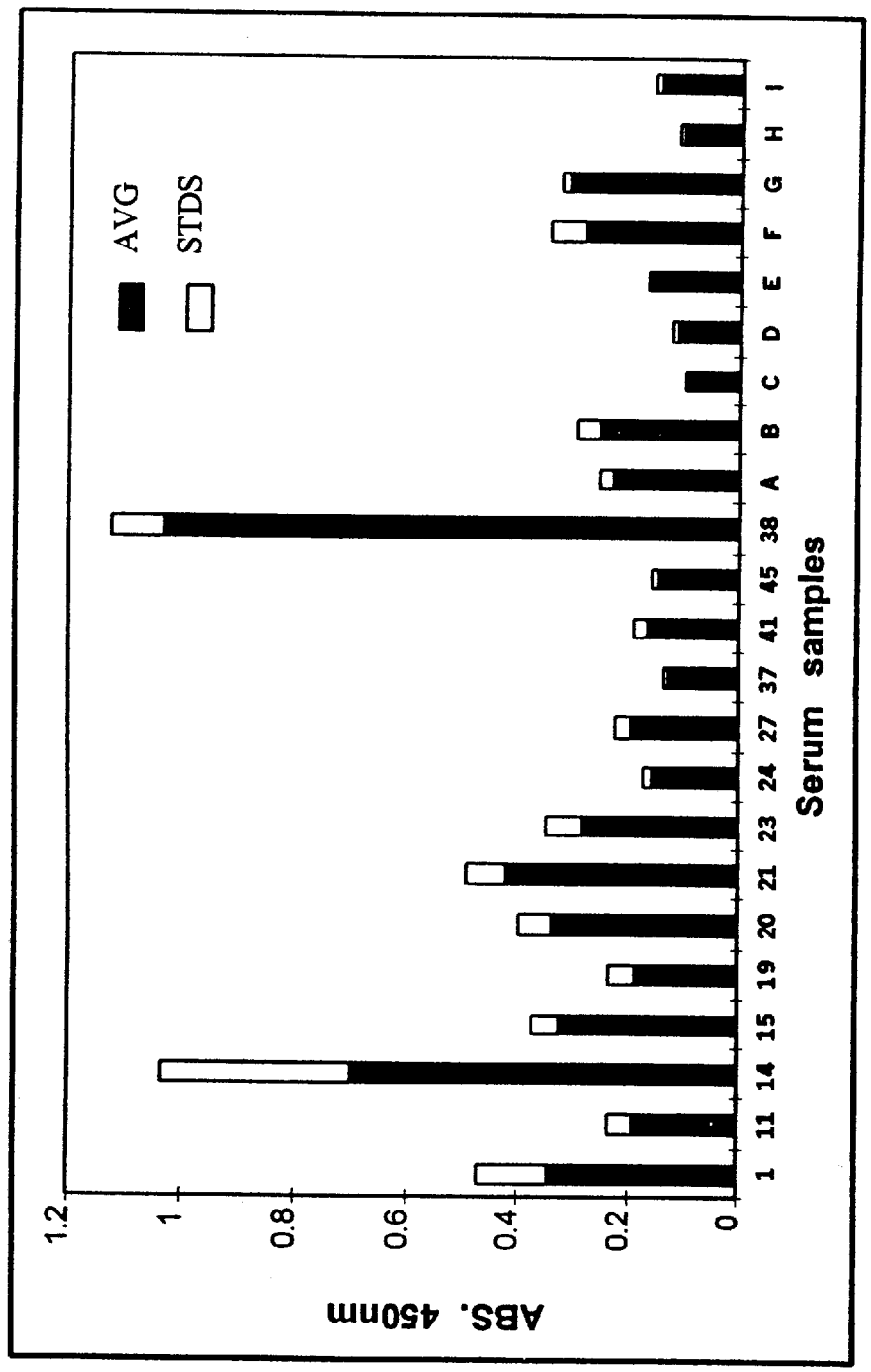
FIG. 29 shows ELISA results of human tuberculosis patients' sera in comparison to healthy control on the plates coated with mycolic acids.
Figure 29B:
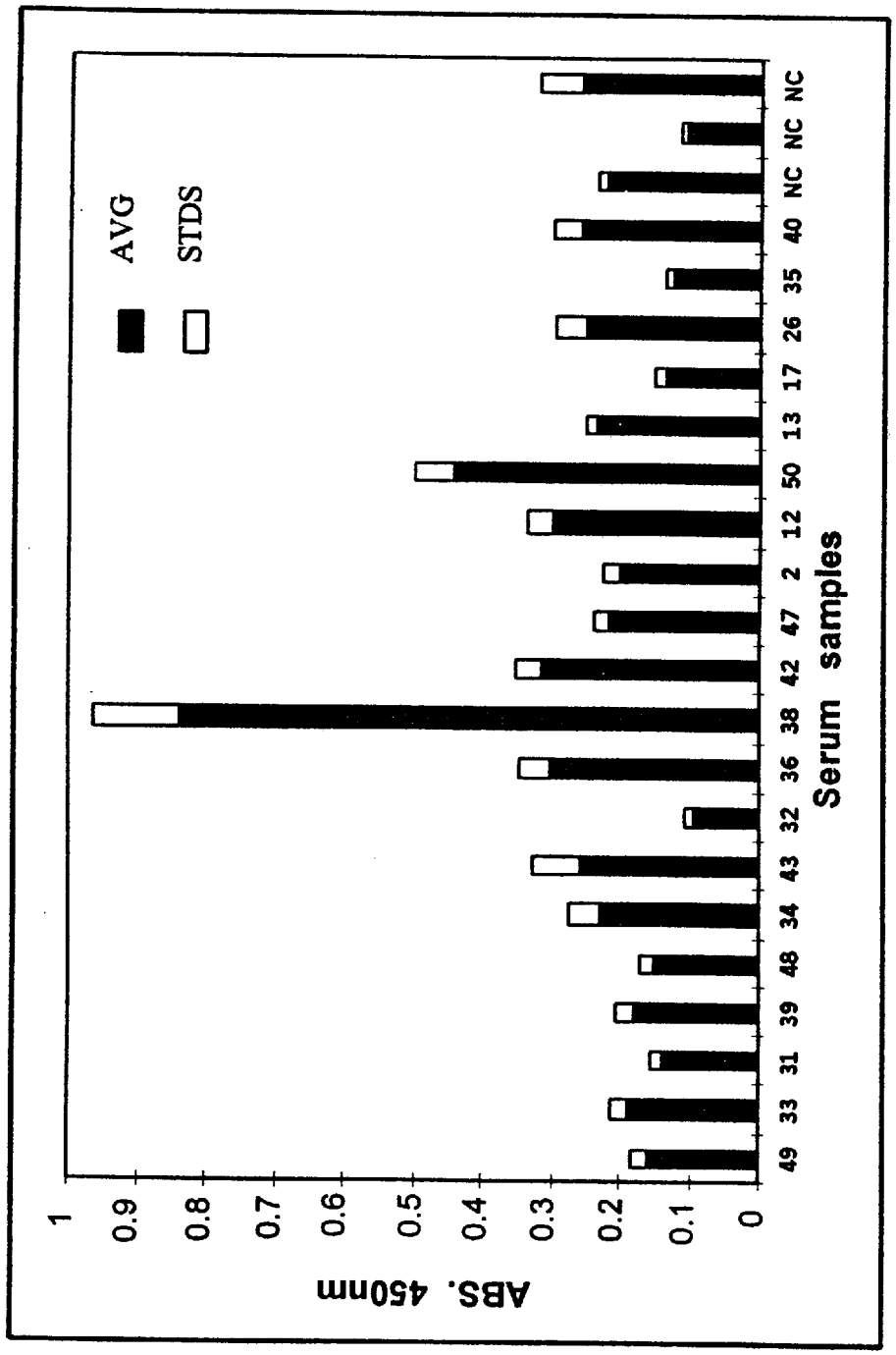
Figure 29C:
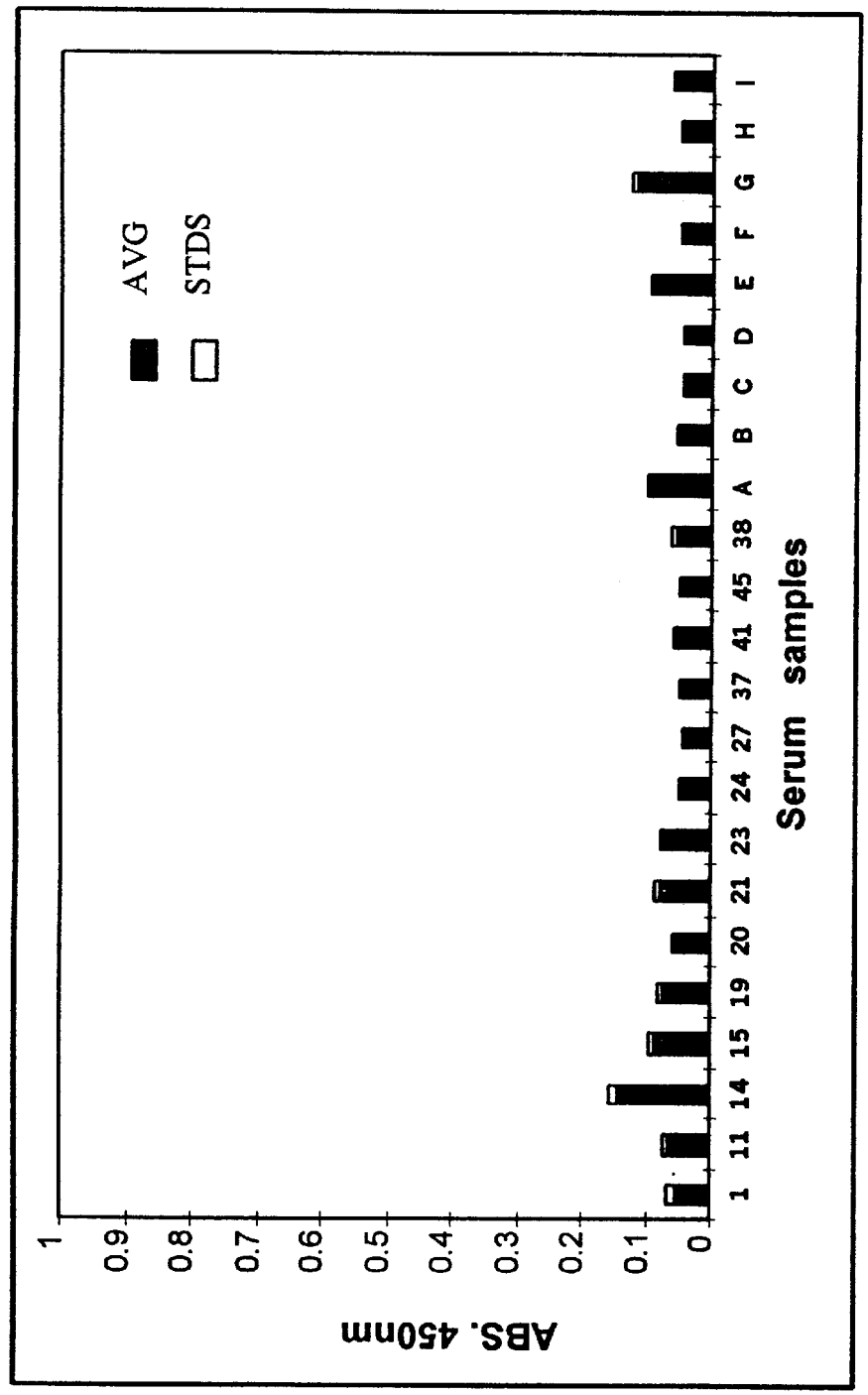
Figure 29D:
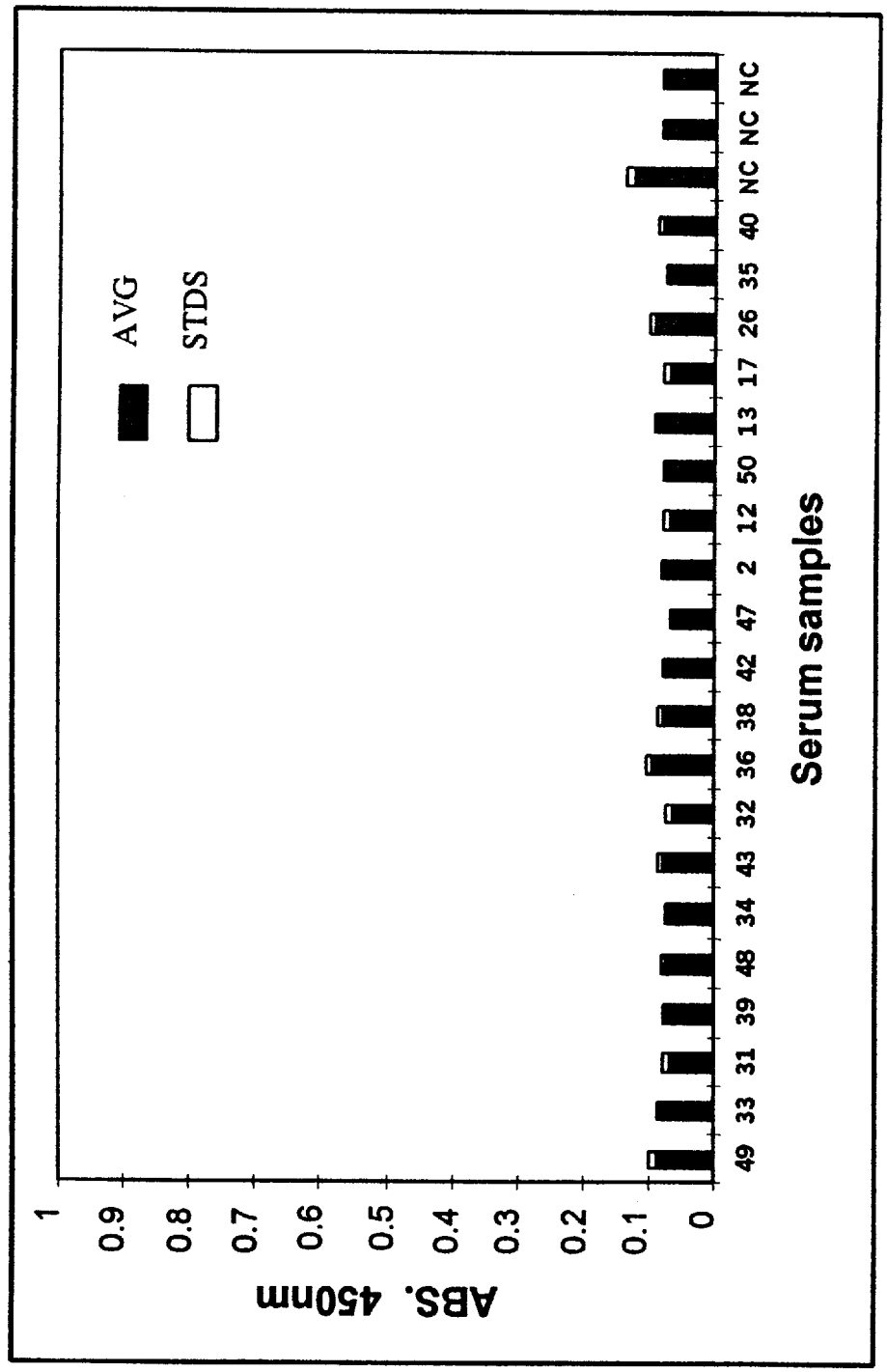

The results presented in FIG. 28 support the hypothesis that mycolic acids are immunogenic in respect of being able to induce anti-mycolic acids antibodies.

3.3.2 The Detection of Anti-mycolic Acids Antibodies in Human Tuberculosis Patients Two out of 58 human tuberculosis patients sera screened, revealed the presence of antibodies recognising methyl-ester form of mycolic acids (FIG. 29).

Figure 30:
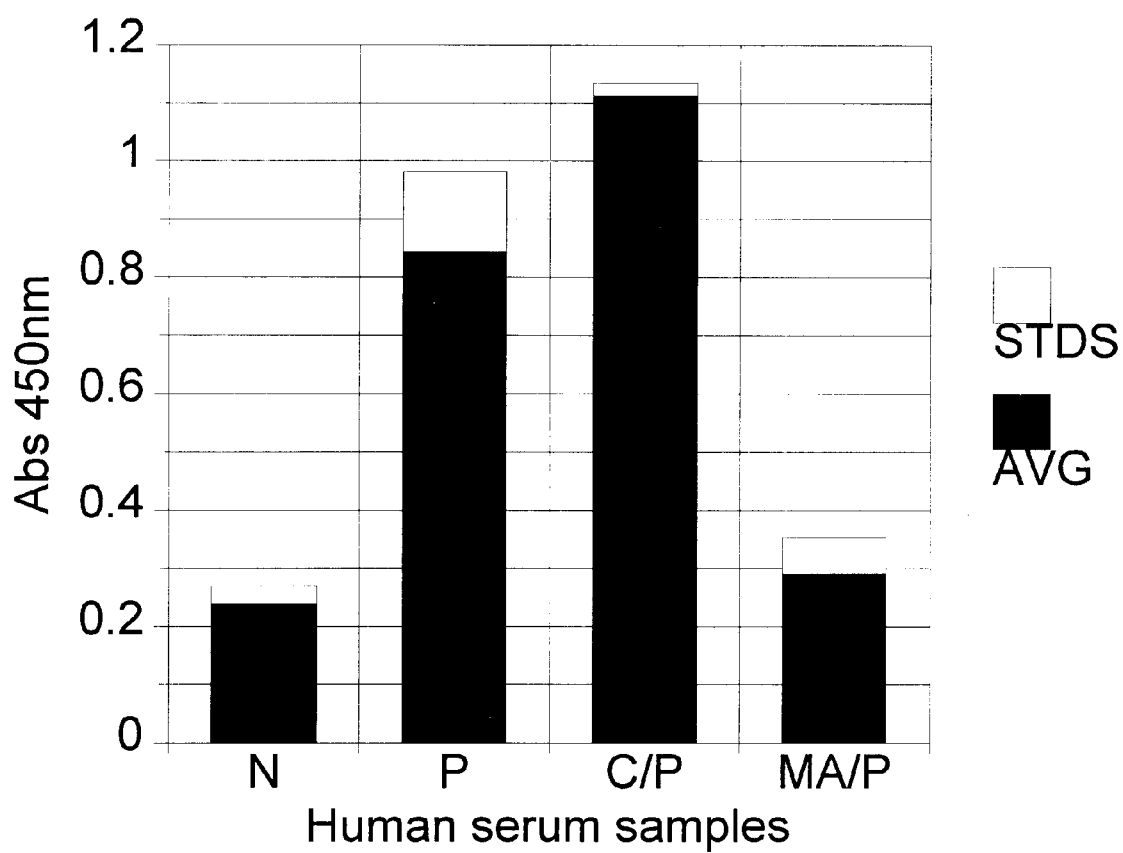
FIG. 30 is a specificity assay of antibodies of human tuberculosis patient No. 38 assessed by inhibition of ELISA.

The specificity of these antibodies was confirmed by an inhibition ELISA reaction carried out as described under 3.2.18. The results obtained are presented in FIG. 30

The results imply that mycolic acids shed from the cell walls of *M. tuberculosis* infecting the human host may induce the formation of anti-mycolic acids antibodies in patients. However, the antibodies are produced at a low frequency, or there is a stage of the infection during which the antibodies are not detected. The antibodies are specific (FIG. 30), but their affinity is low due to the high serum concentration required to give a detectable signal.

Figure 31:
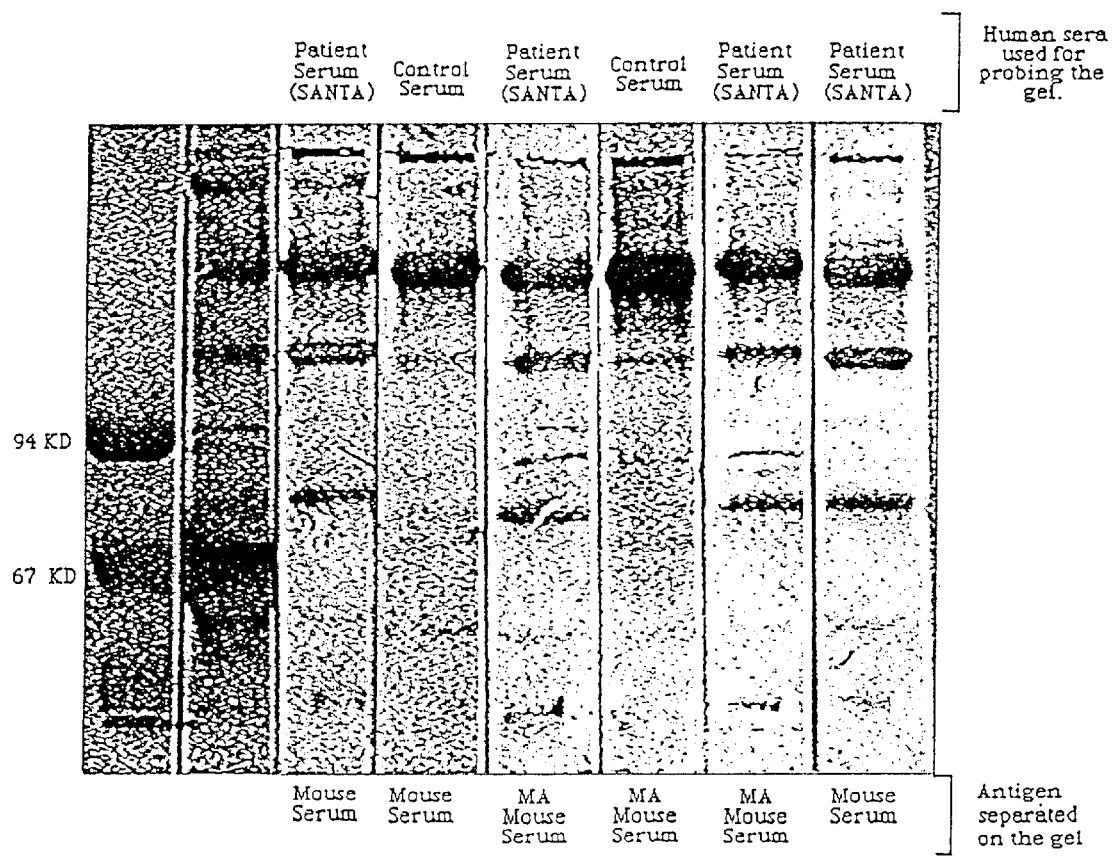
FIG. 31 is a Western blot of mouse serum with and without exposure to mycolic acids, probed with human tuberculosis patients' sera and a healthy control serum.

Anti-mycolic acids antibodies from human tuberculosis patients recognise a preferred serum protein of +/–80 kDa on control mouse serum exposed to purified mycolic acids in methyl-ester form An illustration of this observation is given in FIG. 31.

The result presented in FIG. 31 could not be easily reproduced with the sera of other human tuberculosis patients, probably due to the fact that these antibodies occur at low frequencies. The +/–80 kDa mouse protein appears to enhance the antigenicity of mycolic acids and its human homologue may therefore also increase the imnunogenicity of mycolic acids in blood of human tuberculosis patients.

3.3.3 Response of Human CD4 T Cells to the in vitro Stimulation with Mycolic Acids In order to establish the extent of the human T-cell response to mycolic acids stimulation, besides the known stimulation of double negative (DN) T cells (Porcelli, Morita and Brenner, 1992; Beckman et al., 1994), CD4 T cells and CD8 T cells were exposed to CD1-expressing antigen presenting cells and the cell proliferation was measured. The results are presented in FIGS. 32*a* and 32*b*.

Figure 32A:
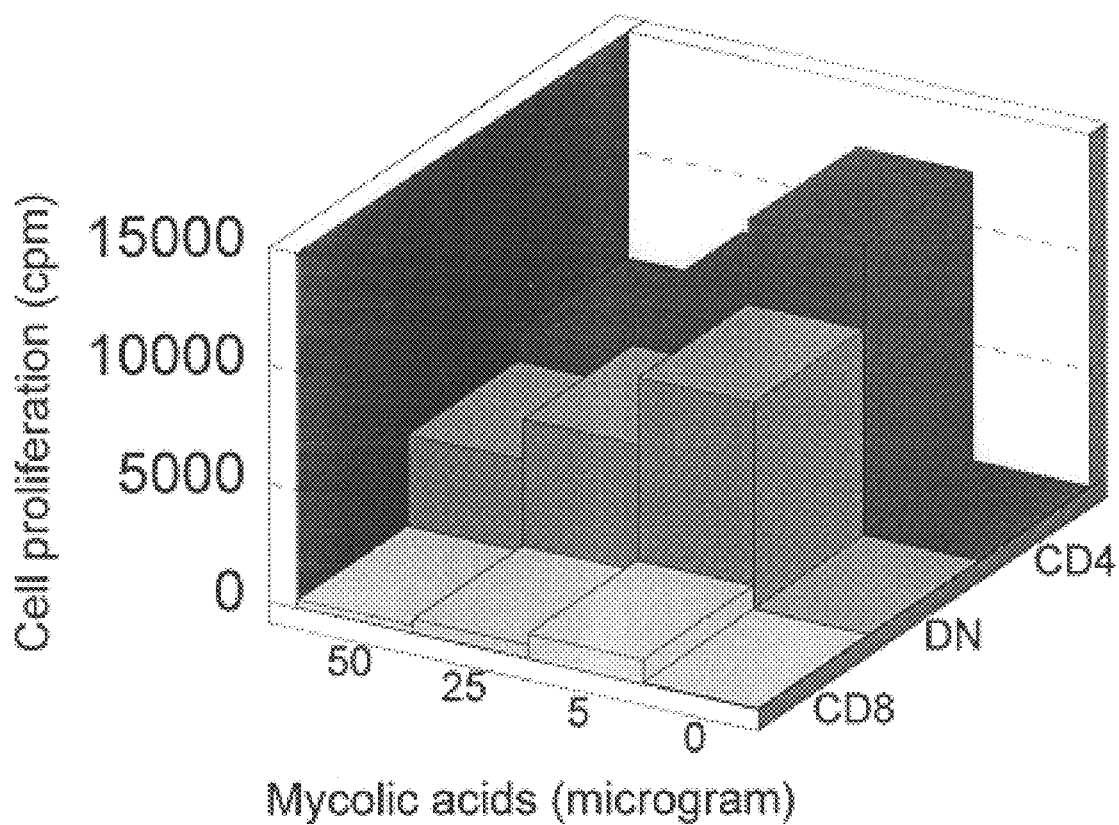
FIG. 32a shows the stimulation by mycolic acids of human T cells by CD1 presenting cells.

The results in FIG. 32*a* indicate stronger stimulation of CD4 T cells by mycolic acids at a frequency higher than that of DN T cells. This effect was not previously reported by Beckman et al., (1995) or other researchers.

Figure 32B:
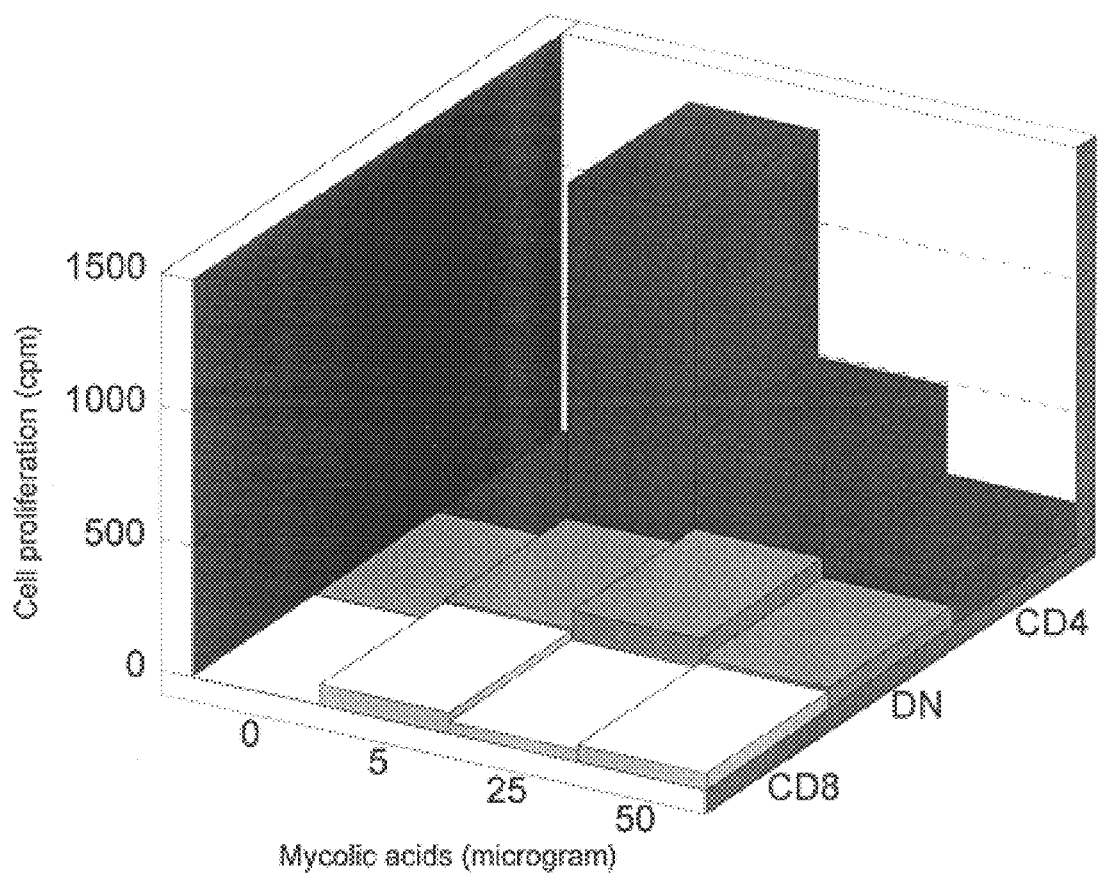
FIG. 32b shows the stimulation of human T cells by mycolic acids.

On the other hand, upon exposure to non-CD1 expressing APCs, CD4 T cells also showed a significant but weak cell proliferation after mycolic acids treatment (FIG. 32*b*). No stimulation of DN T cells was observed. This result may, therefore, suggest a non-CD1 dependent way of mycolic acids presentation by APC cells in order to activate CD4 T cells.

On the basis of these results, immunoregulatory properties of mycolic acids appear to be mediated by both DN and CD4 T cells, but not by CD8 T cells.

Conclusions

1. On the basis of the results reported above it can be concluded that mycolic acids originating from *M. tuberculosis* H37Rv purified using counter-current purification, possess immunoregulatory and immunogenic properties and can be used in the prophylaxis and/or therapy of diseases, particularly those induced by or associated with Mycobacteria.
2. Mycolic acids can protect mice against infection with *M. tuberculosis,* especially when administered before the infection/onset of the disease.
3. The protection provided by mycolic acids manifested itself mainly in the lungs. The lungs from the mycolic acids-pre-treated animals were the only organ in which a significantly reduced tubercle formation could be observed upon macroscopic post-mortem assessment
4. On the basis of cytokine profiling of IL-12, IFN-τ, TNF-α and TGF-β in the organs of the experimental animals, mycolic acids appear to induce upon pre-treatment a pro-inflammatory mechanism of protection against tuberculosis.
5. Preliminary evidence from IR V indicates that mycolic acids from other species of Mycobacterium (e.g. *M. vaccae*) could also induce the protective immune effects in the lungs.
6 Mycolic acids impair the development of arthritic symptoms when introduced before the administration of an arthritis-inducing dose of heat-killed and freeze-dried cells of *M. tuberculosis* H37Ra. This reveals an immunosuppressive regulatory property of mycolic acids, which might be applied in the prevention of auto-immune side-effects of bacterial infections, particularly in the case of *M. tuberculosis* or mycobacterial infections.
7. The results do not exclude a protective effect of mycolic acids treatment after the administration of arthritis-inducing doses of *M. tuberculosis* H37Ra.
8. The immunogenic properties of mycolic acids were confirmed in the experiments in which they induced the formation of antibodies in the experimental animals upon immunization with these compounds. Anti-mycolic acids antibodies occurring spontaneously and detected in human serum were found to be specific but of low affinity.

9. Countercurrent-purified mycolic acids were also found to stimulate human DN and CD4 T cells, but did not appear to have an effect on CD8 T cells.
10. No toxic effects of mycolic acids were detected in control rats within the tested doses, i.e., between 8 and 50 μg for mice and 0.1 and 1 mg for rats.

References

Agrewala, J N and G C Mishra. 1995. A 38-kDa antigen of *Mycobacterium tuberculosis* predominantly induces the secretion of interleukin-2, interferon-gamma and IgG2a antibodies. *Microbiol Immunol*, 39, 801–808.

Beagly, K W, K Fujihashi, C A Black et al. 1993. The *Mycobacterium tuberculosis* 71-kDa heat-shock protein induces proliferation and cytokine secretion by murine gut intraepithelial lymphocytes. *Eur J Immunol*, 23, 2049–2052.

Beckman, E V, S A Porcelli, C T Morita et al. 1994. Recognition of a lipid antigen by CD1-restricted $\alpha\beta^+$ T cells. *Nature*, 372, 691–694.

Beckman, E M, S A Porcelli, C T Morita et al. 1995. CD1 molecules: a third pathway of antigen presentation. *Proceedings of the IX-th International Congress of Immunology, San Francisco*, 23–29 July, 4190.

Beech, J T, L Stasiuk, T A Rainbridge et al. 1995. Pristane-induced arthritis: disease induction or prevention is associated with different T-helper cell subsets. *Proceedings of the IX-th International Congress of Immunology, San Francisco*, 23–29 July, 4723.

Benavides, G R, B Hubby, W M Grosse, R A McGraw and R L Tarlton. 1995. Construction and use of a multi-competitor gene for quantitative RT-PCR using existing primer sets. *J Immunol Methods*, 181, 145–156.

Bermudez, L E M and L S Young. 1988. Tumor necrosis factor, alone or combined with IL-2, but not IFN-γ is associated with macrophage killing of *Mycobacterium avium* complex. *J Immunol*, 140, 3006–3013.

Boom, W H. 1996. The role of T-cell subsets in *Mycobacterium tuberculosis* infection. *Infectious Agents and Disease*, 5, 73–81.

Bost, K L and J D Clements. 1995. In Vivo Induction of Interleukin-12 mRNA Expression after Oral Immunization with *Salmonella dublin* or the B Subunit of *E. coli* Heat-Labile Enterotoxin. *Infect Immun*, 63, 1076–1083.

Brand, D, W Watson, K Whittington et al. 1995. Anti-mouse α1(II)-CB11 antibody epitope profiles differ between chick α1(II)-CB11 immunized collagen arthritis susceptible and resistant mice. *Proceedings of the IX-th International Congress of Immunology, San Francisco*, 23–29 July, 3692.

Bras, A and A P Aguas. 1995. Mycobacteria-induced autoantibody production is associated with susceptibility to infection but not with host propensity to develop autoimmune disease. *Proceedings of the IX-th International Congress of Immunology, San Francisco*, 23–29 July, 2368.

Butler, W R, K C Jost and J O Kilburn 1991. Identification of Mycobacteria by High-Performance Liquid Chromatography. *J Clin Microbiol*, 29, (11), 2468–2472.

Buzas, E I, K Hollo, M Garzo et al., 1995. Partial prevention of proteoglycan (aggrecan) induced murine arthritis by pre- and coimmunization with 65 KD mycobacterial heat shock protein. *Proceedings of the IX-th International Congress of Immunology, San Francisco*, 23–29 July, 5040.

Chantry, D, M Turner, E Abney and M Feldmann. 1989. Modulation of cytokine production by transforming growth factor-beta. *J Immunol*, 142, 4295–4300.

Chomczynski, P and N Sacchi. 1987. Single step method of RNA isolation by acid guanidium thiocyanate-phenol-chloroform extraction. *Analyt Biochem*, 162, 156–159.

Chong, C, K L Bost and J D Clements. 1996. Differential Production of Interleukin-12 mRNA by murine Macrophages in Response to Viable or Killed Salmonella spp. *Infect Immun*, 64, 1154–1160.

Cooper, M A, D K Dalton, T A Stewart et al., 1993. Disseminated tuberculosis in interferon-γ gene-disrupted mice. *J Immunol*, 178, 2243–2247.

D'Andrea, A M, M Rengaraju, N M, Viliante, et al. 1992. Production of natural killer cell stimulatory factor (Interleukin-12) by peripheral blood mononuclear cells. *J Exp Med*, 176, 1387–1398.

Davies, K A, P Norsworthy and M J Walport. 1995. Anti-C1q antibodies are associated with hypo-complementaemia, defective opsonisation of Gram-positive organisms, and death due to infection in patients with SLE. *Proceedings of the IX-th International Congress of Immunology, San Francisco*, 23–29 July, 3637.

Denis, M. 1991. Killing of *Mycobacterium tuberculosis* within human monocytes: activation by cytokines and calcitriol. *Clin Exp Immunol*, 84, 200–208.

Ding, A, C Nathan and S Srimal. 1990. Macrophage deactivating factor and TGFβ inhibit macrophage nitrogen oxide synthesis by IFNγ. *J Immunol*, 145, 940–945.

Dolin, P J, M C Raviglione and A Koch. 1994. Global tuberculosis incidence and mortality during 1990–2000. *Bulletin of the World Health Organisation*, 72, (2), 213–230.

Ebtekar, M and N Khanasri. 1996. Differential antigenic stimulation influences cytokine production patterns T cells and $CD4^{+0}$ subpopulations. *Scand J Immunol*, 43, 391–397.

Elgert, K D. 1996a. Hypersensitivities. In: Immunology—understanding the Immune System. Chpt 15, pp 309–311. Wiley-Liss Inc, Publ. New York, Chichester, Brisbane, Toronto, Singapore.

Elgert, K D. 1996b. Cytokines. In: Immunology—understanding the Immune System. Chpt 10, pp 199–217. Wiley-Liss Inc, Publ. New York, Chichester, Brisbane, Toronto, Singapore.

Elgert, K D. 1996c. The T-cell receptor complex: T-cell activation by processed antigen and cell surface-associated costimulatory molecules. In: Immunology—understanding the Immune System. Chpt 9, pp 173–198. Wiley-Liss Inc, Publ. New York, Chichester, Brisbane, Toronto, Singapore.

Ellner, J J. 1978. Suppressor adherent cells in human tuberculosis. *J Immunol*, 121, 2573–2578.

Espevik, T, I S Figart, M R Shalaby et al. 1987. Inhibition of cytokine production by cyclosporin A and transforming growth factor β. *J Exp Med*, 166, 571–576.

Fenton, M J and M V Vermuelen. 1996. Immunopathology of Tuberculosis: Roles of Macrophages and Monocytes. Minireview. *Infect Immun*, 64, 683–690.

Fine, P E M. 1994. Immunities in and to tuberculosis: implications for pathogenesis and vaccination. In: Tuberculosis Back to the Future, London School of Hygiene & Tropical Medicine, Third Annual Public Health Form; Editors: J. D. H. Porter and K. P. J. McAdam. Publishers: John Wiley & Sons, Chichester, New York, Brisbane, Toronto, Singapore, Chpt 1, pp 13–33.

Flynn, J L, J Chan, K J Triebold et al. 1993. An essential role for interferon γ in resistance to *Mycobacterium tuberculosis*. *J Exp Med*, 178, 2249–2254.

Flynn, J L, M M Goldstein, K J Triebold, K J et al. 1995. IL-12 increases resistance of BALB/c mice to *Mycobacterium tuberculosis* infection. *J Immunol*, 155, 2515–2524.

Gately, M K, R R, Warrier, S Honasoge et al. 1994. Administration of recombinant IL-12 to normal mice enhances cytolytic lymphocyte activity and induces the production of IFN-γ in vivo. *Int Immunol,* 6, 157–167.

Gong, J H, M Zhang, R L Modlin et al. 1996. Interleukin-10 downregulates *Mycobacterium tuberculosis*-induced Th1 responses and CTLA-4 expression. *Infect Immun,* 64, 913–918.

Grange, I M 1984. The humoral immune response in tuberculosis: its nature, biological role and diagnostic usefulness, *Adv Tuberc Res.* 21, 1–78.

Grange, I M, J L Stanford and G A W Rook. 1995. Tuberculosis and cancer: parallels in host responses and therapeutic approaches? *Lancet,* 345, 1350–1352.

Haanen, J B et al. 1991. Selection of a human T helper type 1-like T cell subset by mycobacteria. *J Exp Med,* 174, 583–590.

Hart, C A, N J Beeching and B I Duerden 1996. "Tuberculosis into the next century. Review Article. *J Med Microbiol,* 44, 1–34.

Heath, A W and H L, Playfair. 1992. The potential of cytokines as adjuvants. *AIDS Research and Human Retroviruses,* 8, 1401–1411.

Heifets, L B and Good, R C. 1994. Current Laboratory Methods for the Diagnosis of Tuberculosis. In: Tuberculosis—pathogenesis, protection, and control. Ed. B R Bloom, Chpt 7., pp 85–110.

Hirsch, C S, T Yoneda, J J Ellner et al. 1994. Enhancement of intracellular growth of *M. tuberculosis* in human monocytes by transforming growth factor β. *J Infect Dis,* 170, 1229–1237.

Hirsch, C S, R Hussain, Z Toossi et al. 1996. Cross modulation by transforming growth factor β in human tuberculosis, suppression of antigen-driven blastogenesis and interferon γ production. *Proc Nat Acad Sci, USA,* 93, 3193–3198.

Holland, S M et al. 1994. Treatment of refractory disseminated nontuberculous mycobacterial infection with interferon γ. *N Engl J Med,* 330, 1348–1354.

Huygen, K, J O van Vooren, M Turneer et al. 1988. Specific lymphoproliferation, gamma interferon production, and serum immunoglobulin G directed against a purified 32 kDa mycobacterial protein antigen (P32) in patients with active tuberculosis. *Scand J Immunol,* 27, 187–194.

Janeway, C A and P Travers. 1994a. T-cell mediated immunity. In: Immunobiology, Blackwell Scientific Publications, Oxford, Chpt 7, pp 7.1–7.49.

Janeway, C A and P Travers. 1994b. Host Defense Against Infection. In: Immunobiology, Blackwell Scientific Publications, Oxford, Chpt 9, pp 9.10–9.11.

Janeway, C A and P Travers. 1994c. Endogenous regulation of the immune response. In: Immunobiology, Blackwell Scientific Publications, Oxford, Chpt 12 pp: 12.14–12.17.

Janeway, C A and P Travers. 1994d. The thymus and the development of T lymphocytes. In: Immunobiology, Blackwell Scientific Publications, Oxford, Chpt 6, pp: 6.1–6.37.

Janeway, C A and P Travers. 1994e. Immune responses in the absence of infection. In: Immunobiology, Blackwell Scientific Publications, Oxford, Chpt 11, pp: 11.1–11.49.

Kaufman, S H E. 1995a. Immunity to intracellular bacteria and protozoa. *The Immunologist.* 3, 221–225.

Kaufman, S H E. 1995b. Immunity to intracellular microbial pathogens. *Immunology Today.* 16, 338–342.

Kisielow, P, H Bluthmann, U D Staerz et al. 1988. Tolerance in T cells receptor transgenic mice involves deletion of nonmature $CD4^+8^+$ thymocytes. *Nature,* 333, 742–746.

Kleinhenz, M E and J J Ellner. 1985. Immunoregulatory adherent cells in human tuberculosis: radiation-sensitive antigen-specific suppression by monocytes. *J Infec Dis,* 152, 171–176.

Kleinhenz, M F and J J Ellner. 1987. Antigen responsiveness during tuberculosis: regulatory interaction of T-cell subpopulation and adherent cells. *J Lab Clin Med,* 10, 31–40.

Kobayashi, M, L Fitz, M Ryan et al. 1989. Identification and purification of natural killer cell stimulatory factor (NKSF) a cytokine with multiple biologic effects on human lymphocytes. *J Exp Med,* 170, 827–845.

Kobayashi, K, J Yamazaki, T Kasama et al., 1996. Interleukin (IL)-12 deficiency in susceptible mice infected with *Mycobacterium avium* and amelioration of established infection by IL-12 replacement therapy. *J Inf Dis,* 174, 564–573.

Laboratory Manual of tuberculosis methods. 1980. Tuberculosis Research Institute, Pretoria. Second Ed., revised by E E Nel, H H Kleeberg and E M S Gatner.

Laycock, C A, A F Mulcahy, J A Goodacre and A G Diamond. 1995. Cartilage proteoglycan peptides and fragments as autoantigens in rheumatoid arthritis. Proceedings of the IX-th International Congress of Immunology, San Francisco, 23–29 July, 4924.

Laemmli, E K. 1970. Cleavage of structural proteins during the assembly of the head of bacteriophage T4. *Nature.* 227, 680–685.

Lemonidis, A S, P Toivanen, E J Elson and S J Thompson. 1995. Pristane-induced arthritis associated with changes in bacterial bowel flora. *Proceedings of the IX-th International Congress of Immunology, San Francisco,* 23–29 July, 2337.

Leeson, T S and C R Leeson, 1981. The respiratory system. In: Histology, 4th edition, W B Saunders Co, Philadelphia, London, Toronto, Chpt. 12, pp: 410–427.

Lin, Y, M Zhang, F M Hofman et al., 1996. Absence of a prominent Th2 cytokine response in human tuberculosis. 64, 1351–1356.

Lowrie, D B, R T Tascon, M J Colston and C L Silva. 1994. Towards a DNA vaccine against tuberculosis. *Vaccine,* 12, 1537–1540.

Luna, L G. 1968. Manual of histologic staining methods of the Armed Forces Institute of Pathology. McGraw Hill Book Company, pp 218–219.

Ma, Y, K P Seiler, K F Tai et al., 1994. Outer surface lipoproteins of *Borrelia burgdorferi* stimulate nitric oxide production by the cytokine inducible pathway. *Infect Immun.,* 62, 3663–3671.

Maniatis, T. 1982. Molecular Cloning. A Laboratory Manual. Cold Spring Laboratory Publications, New York.

McDonough, K A, Y Kress B R and Bloom. 1993. Pathogenesis of tuberculosis: interaction of *Mycobacterium tuberculosis* with macrophages. *Infect Immun,* 61, 2763–1773.

Merck Manual. 1987. Autoimmune disorders. Edited by R Berkow, XV-th edition, pp 319–322.

Moudgil, K D, T Chang, H Eradat et al. 1995. Involvement of diversification of T cell response to mycobacterial HSP65 (HPSP65) in inducing remission of protection from adjuvant-induced arthritis. *Proceedings of the IX-th International Congress of Immunology, San Francisco,* 23–29 July, 2367.

Mullis, K B and F A Faloona. 1987. Specific Synthesis of DNA in vitro via a Polymerase Chain Reaction. *Meth Enzymol,* 155, 335–350.

Nardell, E. 1993. Pathogenesis of tuberculosis. In: Lung biology in health and disease. Edited by Reichman, L B and Hirschfield, E. Marcel Dekker, Inc. New York. p. 103–123.

Niehues, T, B Gulwani-Akolkar, P N Akolkar et al. 1994. Unique phenotype and distinct repertoire in human peripheral blood αβTCR⁺, and CD8⁻ double negative T cells. *J Immunol*, 173, 1072–1081.

Niehues, T, D Eichelbauer, W Tax et al. 1995a. Functional characteristics of human peripheral blood γδTCR+ CD4- and CD8-double negative (DN) T-cells. *Proceedings of the IX-th International Congress of Immunology, San Francisco*, 23–29 July, 2440.

Niehues, T, D Eichelbauer, W Tax et al. 1995b. Antigen presenting cell independent proliferation of human peripheral blood α/β TCR⁺ and CD4- and CD8-double negative T cells in response to PHA. *Proceedings of the 24th Annual Meeting of the International Society for Experimental Haematology, August 27–31, Dusseldorf, Germany*, 615.

Onwubalili, K, G M Scott and J A Robinson. 1985. Deficient immune interferon production in tuberculosis. *Clin Exp Immunol*, 59, 405–413.

Orme, I M. 1993. Immunity to mycobacteria. *Curr Opin Immunol*, 5, 497–502.

Porcelli, S, C T Morita and M B Brenner. 1992. CD1b restricts the response of human CD4⁻8⁻ T lymphocytes to a microbial antigen. *Nature*, 360, 593–597.

Ragno, S, V R Winrow, P Mascagni, P Lucietto, F Di Pierro, C J Morris and D R Blake. 1996. A synthetic 10-kD heat shock protein (hsp10) from *Mycobacterium tuberculosis* modulates adjuvant arthritis. *Clin Exp Immunol*, 103, 384–390.

Rastogi, N, M Bachelet and J Carvalho de Sousa. 1992. Intracellular growth of *Mycobacterium avium* in human macrophages is linked to the increased synthesis of prostaglandin E2 and inhibition of the phagosome-lysosome fusion. *FEMS Microbiol. Immunol*, 4, 273–279.

Reiner, S L, S Zheng, D B Corry and R M Locksley. 1993. Constructing polycompetitor cDNAs for quantitative PCR. *J Immunol Meth*, 165, 37–46.

Roitt, I. 1994. Autoimmune diseases. In: Essential Immunology. Blackwell Scientific Publications. Oxford, Chpt. 19, pp: 390–396.

Rook, G A W, J Taverne, C Leveton and J Steele. 1987. The role of gamma interferon, vitamin D3 metabolites and tumor necrosis factor in the pathogenesis of tuberculosis. *Immunology*, 67, 229–243.

Rosat, J-P, E M Beckman, S Porcelli and M B Brenner. 1995. CD-1 restricted γδ T-cell response to mycobacterial antigens. Proceedings of the IX-th International Congress of Immunology, San Francisco, 23–29 July, 1488.

Saiki, R K, D H Gelfand, S Stoffel, et al. 1988. Primer-directed Enzymatic Amplification of DNA with a Thermostable DNA Polymerase. *Science*, 239, 487–491.

Sakai, L Y. 1995. The extracellular matrix. *Scientific American, Science and Medicine*, 2, 58–67.

Sakamoto, A, T Sumida, T Maeda et al. 1992. T cell receptor Vβ repertoire of double negative α/β cells in patients with systemic sclerosis. *Arthr Rheumatol*, 35, 944–951.

Sander, B, U Skansen-Saphir, O Damm et al., 1995. Sequential production of Th1 and Th2 cytokines in response to live bacillus Calmette-Guerin. *Immunology*, 86, 512–518.

Savelkoul, H J F, E, Claassen and R Benner, 1997. Modulation of the humoral immune response and its measurements. In: Immunology Methods Manual. Section 13. Ed. I, Lefkovits. Academic Press Ltd, Great Britain.

Schild, H, N Mavaddat, C Litzenberger et al. 1994. The nature of major histocompatibility complex recognition by γδ T cells. *Cell*, 76, 29–37.

Schwartz, R H. 1993. T-cell anergy. *Scientific American*, 269, 48–54.

Shivakumar, S, G C Tsokos and S K Datta. 1989. T cell receptor α/β expressing double negative (CD4⁻/CD8⁻) and CD4⁺ T helper cells in humans augment the production of pathogenic anti-DNA auto-antibodies associated with lupus nephritis. *J Immunol*, 143, 103–112.

Sieling, P, D Chaterjee, T Pirgozy, et al. 1995. CD1 presentation of non-peptide ligands from microbial pathogens to αβ TCR T-cells. *Proceedings of the IX-th International Congress of Immunology, San Francisco*, 23–29 July, 2726.

Snider, D. E. 1994. Tuberculosis: the world situation. History of the disease and efforts to combat it. In: Tuberculosis, Back to the Future. London School of Hygiene & Tropical Medicine, Third Annual Public Health Forum. Editors: J. D. H. Porter and K. P. J. McAdam. John Wiley & Sons (Publishers), Chichester, UK, Chpt. 1, pp: 13–33.

Sucrel, H M, M, Tory-Blomberg, S Paulie et al. 1994. Th1/Th2 profiles in tuberculosis, based on the proliferation and cytokine response of blood lymphocytes to mycobacterial antigens. *Immunology*, 81, 171–176.

Tamarin, R. 1996. Principles of Genetics. Fifth Edition. W C Brown Publishers. Iowa.

Tangri, S. R Castano, J E W Miller et al. 1995. CD1 molecules present peptides distinct from other class 1 antigen presenting molecules. *Proceedings of the IX-th International Congress of Immunology, San Francisco*, 23–29 July, 2728.

Thomssen, H, M Kahan and M Londei. 1995. IL-10 has a differential effect on the expression of GM-CSF/IL4 induced MHC class II and CD1 molecules. *Proceedings of the IX-th International Congress of Immunology, San Francisco*, 23–29 July, 4652.

Tizard, I R. 1995a. In: Immunology: An introduction. 4th Ed., Saunders College Publishing, p 395.

Tizard, I R. 1995b. In: Immunology: An introduction. 4th Ed., Saunders College Publishing, p 491.

Toossi, Z. 1996. Cytokine circuits in tuberculosis. *Infectious Agents and Disease*, 5, 98–107.

Toossi, Z, M E Kleinhenz and J J Ellner. 1986. Defective interleukin-2 production and responsiveness in human pulmonary tuberculosis. *J Exp Med*, 163, 1162–1172.

Toossi, Z, K E Edmonds, W J Tomford and J J Ellner. 1989. Suppression of PPD-induced interleukin-2 production by interaction of CD 16 lymphocytes and adherent mononuclear cells in tuberculosis. *J Infect Dis*, 159, 352–356.

Tsunawki, S, M Sporn and C Nathan. 1988. Deactivation of macrophages by TGF-β. *Nature*, 334, 260–263.

Vanham, G, K E Edmonds, L, Qing et al. 1996. Generalized immune activation in pulmonary tuberculosis: co-activation with HIV infection. *Clin Exp Immunol*, (in press).

Vilcek, J, A Klion, D Henriksen-DeStefano et al. 1986. Defective gamma-interferon production in peripheral blood leukocytes of patients with acute tuberculosis. *J Clin Immunol*, 6, 146–151.

Voet, D and J G Voet. 1995. Three-dimensional structures of proteins. In: Biochemistry, John Wiley & Sons, Inv. New York, Chichester, Brisbane, Toronto, Singapore. pp: 156–162.

von Boehmer, H, J Kirberg and B Rocha. 1991. An unusual lineage of αβ T cells that contains autoreactive cells. *J Exp Med*, 174, 1001–1008.

Wallis, R S, R Paranjape and M Phillips. 1993. Identification by two-dimensional gel electrophoresis of a 58-kilodalton tumor necrosis factor-inducing protein of *Mycobacterium tuberculosis*. *Infect Immun*, 61, 627–632.

Wauben, M H M, J P A Wagenaar-Hilber and W van Eden. 1994. Adjuvant arthritis. In: Autoimmune Disease Models. A Guidebook. Chpt. 13, pp 210–216. Academic Press, Inc.

Yoshida, A, Y Koide and M Uchijima. 1995. Dissection of strain difference in acquired protective immunity against *Mycobacterium bovis* Calmette-Guerin bacillus (BCG). Macrophages regulate the susceptibility through cytokine network and the induction of nitric oxide synthase. *J Immunol*, 155, 2057–2066.

Zubay, G. 1993. Biochemistry. Third edition. W C Brown Publishers. Iowa.

What is claimed is:

1. A method for stimulating innate immunity in a subject to enhance resistance to, reduce susceptibility to or decrease pathogenic effects of a mycobacterial infection in the subject, said method comprising administering to the subject a purified mycobacterial mycolic acid or mixture of purified mycobacterial mycolic acids or ester form thereof or synthetic form thereof in an amount that stimulates the innate immunity sufficiently to cause said enhancement in resistance, reduction in susceptibility or decrease in pathogenic effects.

2. A method according to claim 1, wherein said purified mycobacterial mycolic acid, mixture of purified mycobacterial mycolic acids, ester form or synthetic form is administered to the subject before the subject contracts the mycobacterial infection.

3. A method according to claim 2, wherein the purified mycobacterial mycolic acid, mixture of purified mycobacterial mycolic acids, ester form or synthetic form is administered in a manner that promotes a pro-inflammatory response in a lung of the subject.

4. A method according to claim 2, wherein the purified mycobacterial mycolic acid, mixture of purified mycobacterial mycolic acids, ester form or synthetic form is administered in a manner that stimulates the expression of IL12IFN-γ in the lungs of the subject.

5. A method according to claim 1, wherein the purified mycobacterial mycolic acid, mixture of purified mycobacterial mycolic acids, ester form or synthetic form is administered to the subject intravenously.

6. A method according to claim 1, wherein the purified mycobacterial mycolic acid, mixture of purified mycobacterial mycolic acids, ester form or synthetic form is administered intranasally.

7. A method according to claim 1, wherein the purified mycobacterial mycolic acid, mixture of purified mycobacterial mycolic acids, ester form or synthetic form is administered in a manner that modulates or manipulates the humoral immune system or cellular immune system or both in the subject.

8. A method according to claim 1, wherein the purified mycobacterial mycolic acid, mixture of purified mycobacterial mycolic acids, ester form or synthetic form is administered to the subject after the subject has contracted said mycobacterial infection.

9. A method according to claim 8, wherein said purified mycobacterial mycolic acid, mixture of purified mycobacterial mycolic acids, ester form or synthetic form is administered to the subject in a manner that stimulates the expression of TGF-β in the lungs of the subject.

10. A method according to claim 1, wherein the mycobacterial infection is tuberculosis.

* * * * *

UNITED STATES PATENT AND TRADEMARK OFFICE
CERTIFICATE OF CORRECTION

PATENT NO.   : 6,433,013 B1
DATED        : August 13, 2002
INVENTOR(S)  : Jan Adrianus Verschoor et al.

It is certified that error appears in the above-identified patent and that said Letters Patent is hereby corrected as shown below:

<u>Title Page</u>,
Item [63], Related U.S. Application Data, "13" should read -- 3 --.

<u>Column 1</u>,
Line 8, "13" should read -- 3 --.

Signed and Sealed this

Twenty-sixth Day of November, 2002

Attest:

JAMES E. ROGAN
Attesting Officer  Director of the United States Patent and Trademark Office